(12) United States Patent
Woolley et al.

(10) Patent No.: US 12,029,453 B2
(45) Date of Patent: *Jul. 9, 2024

(54) METHOD AND APPARATUS FOR PERFORMING SPINAL SURGERY

(71) Applicant: NuVasive, Inc., San Diego, CA (US)

(72) Inventors: Troy B. Woolley, Erie, CO (US); Nathan Lovell, Oceanside, CA (US); Michael Serra, San Diego, CA (US); Mark Peterson, Central Point, CA (US)

(73) Assignee: Nuvasive Inc., San Diego, PA (US)

( * ) Notice: Subject to any disclaimer, the term of this patent is extended or adjusted under 35 U.S.C. 154(b) by 460 days.

This patent is subject to a terminal disclaimer.

(21) Appl. No.: 17/353,997

(22) Filed: Jun. 22, 2021

(65) Prior Publication Data
US 2021/0307790 A1    Oct. 7, 2021

Related U.S. Application Data

(60) Continuation of application No. 17/193,927, filed on Mar. 5, 2021, now Pat. No. 11,911,078, which is a continuation of application No. 16/243,060, filed on Jan. 8, 2019, now Pat. No. 10,980,576, which is a continuation of application No. 15/394,156, filed on Dec. 29, 2016, now Pat. No. 10,172,652, which is a
(Continued)

(51) Int. Cl.
*A61B 17/02* (2006.01)
*A61B 1/32* (2006.01)
*A61B 17/70* (2006.01)

(52) U.S. Cl.
CPC ............ *A61B 17/7077* (2013.01); *A61B 1/32* (2013.01); *A61B 17/0206* (2013.01); *A61B 17/7076* (2013.01); *A61B 2017/0256* (2013.01)

(58) Field of Classification Search
CPC ... A61B 17/02; A61B 17/0206; A61B 17/025; A61B 17/0218; A61B 2017/0256; A61B 17/7077; A61B 17/7079–7082
See application file for complete search history.

(56) References Cited

U.S. PATENT DOCUMENTS

| | | |
|---|---|---|
| 186,637 A | 1/1877 | Tanner |
| 1,157,202 A | 10/1915 | Bates et al. |

(Continued)

FOREIGN PATENT DOCUMENTS

| | | |
|---|---|---|
| CN | 201341901 | 11/2009 |
| CN | 201537102 | 8/2010 |

(Continued)

OTHER PUBLICATIONS

Authorized Officer Blaine R. Copenheaver, International Search Report and Written Opinion from PCT/US2010/002951, dated Mar. 23, 2011, 19 pages.
(Continued)

*Primary Examiner* — Eduardo C Robert
*Assistant Examiner* — Michelle C Eckman

(57) ABSTRACT

Implants, instruments, and methods for performing surgical procedures on the spine, including one or more of creating an operative corridor to the spine, delivering implants to the spine, fusing one or more segments of the spine, and fixing one or more segments of the spine.

17 Claims, 51 Drawing Sheets

Related U.S. Application Data division of application No. 14/029,724, filed on Sep. 17, 2013, now Pat. No. 9,554,833, which is a continuation of application No. 13/204,583, filed on Aug. 5, 2011, now Pat. No. 8,535,320, which is a continuation of application No. 12/927,415, filed on Nov. 10, 2010, now Pat. No. 8,357,184.

(60) Provisional application No. 61/259,825, filed on Nov. 10, 2009.

(56) References Cited

U.S. PATENT DOCUMENTS

| | | |
|---|---|---|
| 1,223,812 A | 4/1917 | Listlak |
| 1,456,116 A | 5/1923 | Bessesen |
| 2,807,259 A | 9/1957 | Guerriero |
| 3,030,948 A | 4/1962 | Loeffler |
| 3,364,919 A | 1/1968 | Hunnicutt |
| 3,383,769 A | 5/1968 | Davis |
| 3,384,077 A | 5/1968 | Gauthier |
| 3,509,873 A | 5/1970 | Karlin et al. |
| 3,522,799 A | 8/1970 | Gauthier |
| 3,724,449 A | 4/1973 | Gauthier |
| 3,749,088 A | 7/1973 | Kohlmann |
| 3,795,981 A | 3/1974 | Franklin |
| 3,965,890 A | 6/1976 | Gauthier |
| 4,116,232 A | 9/1978 | Rabban |
| 4,156,424 A | 5/1979 | Burgin |
| 4,165,746 A | 8/1979 | Burgin |
| 4,421,107 A | 12/1983 | Estes et al. |
| 4,566,466 A | 1/1986 | Ripple |
| 4,616,635 A | 10/1986 | Caspar et al. |
| 4,686,972 A | 8/1987 | Kurland |
| 4,702,230 A | 10/1987 | Pelta |
| 4,733,657 A | 3/1988 | Kluger |
| 4,747,394 A | 5/1988 | Watanabe |
| 4,747,395 A | 5/1988 | Brief |
| 4,817,587 A | 4/1989 | Janese |
| 4,829,985 A | 5/1989 | Couetil |
| 4,852,552 A | 8/1989 | Chaux |
| 4,877,020 A | 10/1989 | Vich |
| 4,881,525 A | 11/1989 | Williams |
| 4,934,352 A | 6/1990 | Sullivan |
| 4,957,495 A | 9/1990 | Kluger |
| 5,052,373 A | 10/1991 | Michelson |
| 5,297,538 A | 3/1994 | Daniel |
| 5,339,801 A | 8/1994 | Poloyko et al. |
| 5,400,774 A | 3/1995 | Villalta et al. |
| 5,417,230 A | 5/1995 | Wood |
| 5,431,658 A | 7/1995 | Moskovich |
| 5,503,617 A | 4/1996 | Jako |
| 5,512,038 A | 4/1996 | O'Neal |
| 5,609,593 A | 3/1997 | Errico |
| 5,649,931 A | 7/1997 | Bryant |
| 5,728,046 A | 3/1998 | Mayer et al. |
| 5,733,290 A | 3/1998 | McCue |
| 5,746,743 A | 5/1998 | Greenberg |
| 5,755,660 A | 5/1998 | Tyagi |
| 5,755,732 A | 5/1998 | Green |
| 5,772,583 A | 6/1998 | Wright et al. |
| 5,782,830 A | 7/1998 | Farris |
| 5,795,291 A | 8/1998 | Koros |
| 5,797,909 A | 8/1998 | Michelson |
| 5,813,978 A | 9/1998 | Jako |
| 5,846,192 A | 12/1998 | Teixido |
| 5,846,193 A | 12/1998 | Wright |
| 5,882,298 A | 3/1999 | Sharratt |
| 5,890,271 A | 4/1999 | Bromley |
| 5,893,831 A | 4/1999 | Koros |
| 5,902,233 A | 5/1999 | Farley et al. |
| 5,928,139 A | 7/1999 | Koros et al. |
| 5,931,777 A | 8/1999 | Sava |
| 5,944,658 A | 8/1999 | Koros et al. |
| 5,944,736 A | 8/1999 | Taylor |
| 5,967,972 A | 10/1999 | Santilli |
| 5,976,171 A | 11/1999 | Taylor |
| 5,984,865 A | 11/1999 | Farley et al. |
| 5,993,385 A | 11/1999 | Johnston |
| 6,042,540 A | 3/2000 | Johnston |
| 6,042,542 A | 3/2000 | Koros |
| 6,096,038 A | 8/2000 | Michelson |
| 6,132,370 A | 10/2000 | Furnish et al. |
| 6,139,493 A | 10/2000 | Koros et al. |
| 6,159,215 A | 12/2000 | Urbahns et al. |
| 6,189,422 B1 | 2/2001 | Stihl |
| 6,206,826 B1 | 3/2001 | Mathews et al. |
| 6,224,545 B1 | 5/2001 | Cocchia et al. |
| 6,241,729 B1 | 6/2001 | Estes |
| 6,244,141 B1 | 6/2001 | Han |
| 6,254,532 B1 | 7/2001 | Paolitto et al. |
| 6,280,442 B1 | 8/2001 | Barker |
| 6,296,609 B1 | 10/2001 | Brau |
| 6,319,257 B1 | 11/2001 | Carignan et al. |
| 6,322,500 B1 | 11/2001 | Sikora et al. |
| 6,340,345 B1 | 1/2002 | Lees et al. |
| 6,416,405 B1 | 7/2002 | Brau |
| 6,416,465 B2 | 7/2002 | Brau |
| 6,447,443 B1 | 9/2002 | Keogh et al. |
| 6,454,773 B1 | 9/2002 | Sherman et al. |
| 6,464,634 B1 | 10/2002 | Fraser |
| 6,478,734 B1 | 11/2002 | Taylor |
| 6,478,800 B1 | 11/2002 | Fraser et al. |
| 6,506,151 B2 | 1/2003 | Estes |
| 6,524,238 B2 | 2/2003 | Velikaris |
| 6,551,242 B1 | 4/2003 | Furnish |
| 6,559,240 B2 | 5/2003 | Hsu |
| 6,599,240 B2 | 7/2003 | Puchovsky et al. |
| 6,599,292 B1 | 7/2003 | Ray |
| 6,602,189 B1 | 8/2003 | Bennetti |
| 6,623,485 B2 | 9/2003 | Doubler et al. |
| 6,632,238 B2 | 10/2003 | Ginn |
| 6,660,004 B2 | 12/2003 | Barker et al. |
| 6,675,805 B1 | 1/2004 | Graether |
| 6,689,054 B2 | 2/2004 | Furnish |
| 6,692,434 B2 | 2/2004 | Ritland |
| 6,698,054 B2 | 3/2004 | Furnish |
| 6,733,444 B2 | 5/2004 | Phillips |
| 6,746,467 B1 | 6/2004 | Taylor |
| 6,749,613 B1 | 6/2004 | Conchy et al. |
| 6,802,844 B2 | 10/2004 | Ferree |
| 6,835,196 B2 | 12/2004 | Biedermann et al. |
| 6,857,343 B1 | 2/2005 | Easterbrooks et al. |
| 6,860,850 B2 | 3/2005 | Phillips |
| 6,869,398 B2 | 3/2005 | Obenchain |
| 6,887,197 B2 | 5/2005 | Phillips |
| 6,887,198 B2 | 5/2005 | Phillips |
| 6,918,911 B2 | 7/2005 | Biedermann |
| 6,929,606 B2 | 8/2005 | Ritland |
| 6,945,933 B2 | 9/2005 | Branch et al. |
| 6,951,538 B2 | 10/2005 | Ritland |
| 6,964,666 B2 | 11/2005 | Jackson |
| 6,997,086 B1 | 2/2006 | Graham |
| 7,001,333 B2 | 2/2006 | Hamel |
| 7,011,658 B2 | 3/2006 | Young |
| 7,014,608 B2 | 3/2006 | Larson et al. |
| 7,029,472 B1 | 4/2006 | Fortin |
| 7,108,698 B2 | 9/2006 | Robbins |
| 7,147,599 B2 | 12/2006 | Phillips |
| 7,150,714 B2 | 12/2006 | Myles |
| 7,166,073 B2 | 1/2007 | Ritland |
| 7,182,729 B2 | 2/2007 | Abdelgany et al. |
| 7,207,949 B2 | 4/2007 | Miles et al. |
| 7,214,186 B2 | 5/2007 | Ritland |
| 7,235,048 B2 | 6/2007 | Rein |
| 7,250,052 B2 | 7/2007 | Landry et al. |
| 7,288,065 B1 | 10/2007 | Taylor |
| 7,318,817 B2 | 1/2008 | Hamada |
| 7,374,534 B2 | 5/2008 | Dalton |
| 7,396,328 B2 | 7/2008 | Penenberg |
| 7,455,639 B2 | 11/2008 | Ritland |
| 7,473,222 B2 | 1/2009 | Dewey et al. |
| 7,473,223 B2 | 1/2009 | Fetzer |
| 7,481,766 B2 | 1/2009 | Lee |

(56) References Cited

U.S. PATENT DOCUMENTS

| | | |
|---|---|---|
| 7,494,463 B2 * | 2/2009 | Nehls ............... A61B 17/0206 606/105 |
| 7,513,869 B2 | 4/2009 | Branch |
| 7,537,565 B2 | 5/2009 | Bass |
| 7,569,014 B2 | 8/2009 | Bass |
| 7,582,058 B1 | 9/2009 | Miles et al. |
| 7,588,537 B2 | 9/2009 | Bass |
| 7,588,593 B2 | 9/2009 | Aferzon |
| 7,594,888 B2 | 9/2009 | Raymond et al. |
| 7,618,424 B2 * | 11/2009 | Wilcox ............. A61B 17/7077 606/86 R |
| 7,654,954 B1 | 2/2010 | Phillips |
| 7,664,544 B2 | 2/2010 | Miles et al. |
| 7,686,809 B2 | 3/2010 | Triplett |
| 7,691,057 B2 | 4/2010 | Miles et al. |
| 7,699,774 B1 | 4/2010 | Taylor |
| 7,722,618 B2 | 5/2010 | Estes |
| 7,753,844 B2 | 7/2010 | Sharratt |
| 7,758,501 B2 | 7/2010 | Frasier |
| 7,819,801 B2 | 10/2010 | Miles et al. |
| 7,846,093 B2 | 12/2010 | Gorek et al. |
| 7,846,167 B2 | 12/2010 | Garcia et al. |
| 7,850,608 B2 | 12/2010 | Hamada |
| 7,892,173 B2 | 2/2011 | Miles |
| 7,905,840 B2 | 3/2011 | Pimenta et al. |
| 7,909,829 B2 | 3/2011 | Patel |
| 7,909,846 B1 | 3/2011 | Taylor |
| 7,909,848 B2 | 3/2011 | Patel |
| 7,918,792 B2 | 4/2011 | Drzyzga et al. |
| 7,922,658 B2 | 4/2011 | Cohen et al. |
| 7,927,337 B2 | 4/2011 | Keller |
| 7,931,589 B2 | 4/2011 | Cohen et al. |
| 7,935,051 B2 | 5/2011 | Miles |
| 7,935,053 B2 | 5/2011 | Karpowicz |
| 7,946,982 B2 | 5/2011 | Hamada |
| 7,959,564 B2 | 6/2011 | Ritland |
| 7,976,463 B2 | 7/2011 | Dewey et al. |
| 7,976,464 B2 | 7/2011 | Shluzas |
| 7,981,031 B2 | 7/2011 | Frasier et al. |
| 8,043,343 B2 | 10/2011 | Miller et al. |
| 8,062,217 B2 | 11/2011 | Boucher |
| 8,066,710 B2 | 11/2011 | Estes |
| 8,100,828 B2 | 1/2012 | Frey et al. |
| 8,137,284 B2 | 3/2012 | Miles et al. |
| 8,167,887 B2 | 5/2012 | Mclean |
| 8,182,423 B2 | 5/2012 | Miles |
| 8,182,519 B2 | 5/2012 | Loftus et al. |
| 8,187,179 B2 | 5/2012 | Miles |
| 8,192,356 B2 | 6/2012 | Miles |
| 8,192,357 B2 | 6/2012 | Miles |
| 8,357,184 B2 | 1/2013 | Woolley |
| 8,372,081 B1 | 2/2013 | Schafer et al. |
| 8,409,087 B2 | 4/2013 | Ames et al. |
| 8,435,269 B2 | 5/2013 | Woolley |
| 8,460,306 B2 | 6/2013 | Schaffran et al. |
| 8,535,320 B2 | 9/2013 | Woolley |
| 8,603,094 B2 | 12/2013 | Walker et al. |
| 8,636,655 B1 | 1/2014 | Childs |
| 8,764,806 B2 | 7/2014 | Abdou |
| 8,974,381 B1 | 3/2015 | Lovell et al. |
| 9,044,280 B1 | 6/2015 | Arambula |
| 9,050,146 B2 | 6/2015 | Woolley |
| 9,393,044 B2 | 7/2016 | Masson |
| 9,414,828 B2 | 8/2016 | Abidin |
| 9,554,833 B2 | 1/2017 | Woolley |
| 9,700,293 B2 | 7/2017 | Cryder |
| 9,795,370 B2 | 10/2017 | O'Connell |
| 9,820,778 B2 | 11/2017 | Masson |
| 10,172,652 B2 | 1/2019 | Woolley |
| 2002/0123754 A1 | 9/2002 | Holmes |
| 2002/0161368 A1 | 10/2002 | Foley et al. |
| 2003/0055430 A1 | 3/2003 | Kim |
| 2003/0060686 A1 | 3/2003 | Taylor |
| 2003/0149341 A1 | 8/2003 | Clifton |
| 2003/0236447 A1 | 12/2003 | Ritland |
| 2004/0068269 A1 | 4/2004 | Bonati |
| 2004/0147928 A1 | 7/2004 | Landry et al. |
| 2004/0147936 A1 | 7/2004 | Rosenberg |
| 2004/0215199 A1 | 10/2004 | Zinkel |
| 2004/0230191 A1 * | 11/2004 | Frey ................. A61B 17/7082 606/57 |
| 2005/0010220 A1 | 1/2005 | Casutt |
| 2005/0021031 A1 | 1/2005 | Foley et al. |
| 2005/0080320 A1 | 4/2005 | Lee et al. |
| 2005/0090824 A1 | 4/2005 | Shluzas et al. |
| 2005/0131422 A1 | 6/2005 | Anderson |
| 2005/0148826 A1 | 7/2005 | Paolitto et al. |
| 2005/0149053 A1 | 7/2005 | Varieur et al. |
| 2005/0159650 A1 | 7/2005 | Raymond et al. |
| 2005/0165408 A1 | 7/2005 | Puno et al. |
| 2005/0171542 A1 | 8/2005 | Biedermann et al. |
| 2005/0192486 A1 | 9/2005 | Hamel |
| 2005/0192570 A1 | 9/2005 | Jackson |
| 2005/0203533 A1 * | 9/2005 | Ferguson ........... A61B 17/1757 606/90 |
| 2005/0234304 A1 | 10/2005 | Dewey et al. |
| 2005/0240081 A1 | 10/2005 | Ellachar |
| 2005/0245928 A1 | 11/2005 | Colleran et al. |
| 2005/0277812 A1 | 12/2005 | Myles |
| 2005/0277928 A1 * | 12/2005 | Boschert ........... A61B 17/7037 606/328 |
| 2006/0025771 A1 | 2/2006 | Jackson |
| 2006/0036244 A1 | 2/2006 | Spitler et al. |
| 2006/0075856 A1 | 4/2006 | Tilton |
| 2006/0084844 A1 | 4/2006 | Nehls |
| 2006/0100622 A1 | 5/2006 | Jackson |
| 2006/0100637 A1 | 5/2006 | Rathbun |
| 2006/0106416 A1 | 5/2006 | Raymond et al. |
| 2006/0111712 A1 | 5/2006 | Jackson |
| 2006/0111715 A1 | 5/2006 | Jackson |
| 2006/0142761 A1 | 6/2006 | Landry et al. |
| 2006/0149232 A1 | 7/2006 | Sasing |
| 2006/0149240 A1 | 7/2006 | Jackson |
| 2006/0183978 A1 | 8/2006 | Howard |
| 2006/0189848 A1 | 8/2006 | Penenberg |
| 2006/0200133 A1 | 9/2006 | Jackson |
| 2006/0206009 A1 | 9/2006 | Von Wald |
| 2006/0241603 A1 | 10/2006 | Jackson |
| 2006/0241618 A1 | 10/2006 | Gasser et al. |
| 2006/0247637 A1 | 11/2006 | Colleran et al. |
| 2006/0247658 A1 | 11/2006 | Pond, Jr. et al. |
| 2006/0264962 A1 | 11/2006 | Chin |
| 2006/0271047 A1 | 11/2006 | Jackson |
| 2006/0271050 A1 | 11/2006 | Piza Vallespir |
| 2006/0276789 A1 | 12/2006 | Jackson |
| 2006/0276792 A1 | 12/2006 | Ensign et al. |
| 2006/0278050 A1 | 12/2006 | Hsiao |
| 2006/0287674 A1 | 12/2006 | Ginn et al. |
| 2007/0016200 A1 | 1/2007 | Jackson |
| 2007/0032162 A1 | 2/2007 | Jackson |
| 2007/0038033 A1 | 2/2007 | Jones et al. |
| 2007/0049931 A1 | 3/2007 | Justis et al. |
| 2007/0049933 A1 | 3/2007 | Ahn et al. |
| 2007/0055109 A1 | 3/2007 | Bass |
| 2007/0055240 A1 | 3/2007 | Matthis |
| 2007/0055241 A1 | 3/2007 | Matthis et al. |
| 2007/0055244 A1 | 3/2007 | Jackson |
| 2007/0073111 A1 | 3/2007 | Bass |
| 2007/0073112 A1 | 3/2007 | Holmes |
| 2007/0083086 A1 | 4/2007 | LeVahn |
| 2007/0088357 A1 | 4/2007 | Johnson et al. |
| 2007/0090238 A1 | 4/2007 | Justis |
| 2007/0093818 A1 | 4/2007 | Biedermann et al. |
| 2007/0093828 A1 | 4/2007 | Abdou |
| 2007/0100212 A1 | 5/2007 | Pimenta et al. |
| 2007/0106123 A1 | 5/2007 | Gorek et al. |
| 2007/0123862 A1 | 5/2007 | Warnick |
| 2007/0123870 A1 | 5/2007 | Jeon et al. |
| 2007/0129608 A1 | 6/2007 | Sandhu |
| 2007/0135817 A1 | 6/2007 | Ensign |
| 2007/0156024 A1 | 7/2007 | Frasier et al. |
| 2007/0167949 A1 | 7/2007 | Altarac et al. |
| 2007/0173819 A1 | 7/2007 | Sandlin |
| 2007/0179343 A1 | 8/2007 | Shelokov |

(56) References Cited

U.S. PATENT DOCUMENTS

| | | |
|---|---|---|
| 2007/0191955 A1 | 8/2007 | Zucherman et al. |
| 2007/0198062 A1 | 8/2007 | Miles et al. |
| 2007/0208227 A1 | 9/2007 | Smith et al. |
| 2007/0208228 A1 | 9/2007 | Pavento et al. |
| 2007/0225568 A1 | 9/2007 | Colleran |
| 2007/0233079 A1 | 10/2007 | Fallin et al. |
| 2007/0233097 A1 | 10/2007 | Anderson et al. |
| 2007/0238932 A1 | 10/2007 | Jones |
| 2007/0270842 A1 | 11/2007 | Bankoski et al. |
| 2008/0021285 A1 | 1/2008 | Drzyzga et al. |
| 2008/0045957 A1 | 2/2008 | Landry |
| 2008/0058606 A1 | 3/2008 | Miles et al. |
| 2008/0077136 A1 | 3/2008 | Triplett et al. |
| 2008/0077138 A1 | 3/2008 | Cohen et al. |
| 2008/0077139 A1 | 3/2008 | Landry et al. |
| 2008/0114208 A1 | 5/2008 | Hutton |
| 2008/0146881 A1 | 6/2008 | Alimi |
| 2008/0154277 A1 | 6/2008 | Machalk et al. |
| 2008/0154281 A1 | 6/2008 | Schaffran et al. |
| 2008/0177274 A1 | 7/2008 | Gil et al. |
| 2008/0177322 A1 | 7/2008 | Davis |
| 2008/0183044 A1 | 7/2008 | Colleran et al. |
| 2008/0183045 A1* | 7/2008 | Perez-Cruet ......... A61B 17/025 600/210 |
| 2008/0183046 A1 | 7/2008 | Boucher et al. |
| 2008/0183214 A1 | 7/2008 | Copp et al. |
| 2008/0188718 A1 | 8/2008 | Spitler et al. |
| 2008/0200918 A1 | 8/2008 | Spitler et al. |
| 2008/0249372 A1 | 10/2008 | Reglos |
| 2008/0255567 A1* | 10/2008 | Accordino ......... A61B 17/7077 606/90 |
| 2008/0262318 A1 | 10/2008 | Gorek et al. |
| 2008/0294205 A1 | 11/2008 | Greenhalgh et al. |
| 2009/0012370 A1 | 1/2009 | Gutierrez |
| 2009/0018399 A1 | 1/2009 | Martinelli et al. |
| 2009/0036746 A1 | 2/2009 | Blackwell et al. |
| 2009/0076333 A1 | 3/2009 | Bjork |
| 2009/0076516 A1 | 3/2009 | Lowry et al. |
| 2009/0105547 A1 | 4/2009 | Vayser et al. |
| 2009/0124860 A1 | 5/2009 | Miles et al. |
| 2009/0124861 A1 | 5/2009 | Fetzer |
| 2009/0143828 A1 | 6/2009 | Stad et al. |
| 2009/0222046 A1 | 9/2009 | Gorek |
| 2009/0227845 A1 | 9/2009 | Lo |
| 2009/0270916 A1 | 10/2009 | Ramsay et al. |
| 2010/0030224 A1 | 2/2010 | Winslow et al. |
| 2010/0081885 A1 | 4/2010 | Wing |
| 2010/0114182 A1 | 5/2010 | Wilcox et al. |
| 2010/0137915 A1 | 6/2010 | Anderson et al. |
| 2010/0217089 A1 | 8/2010 | Farley |
| 2010/0249856 A1 | 9/2010 | Iott et al. |
| 2010/0262198 A1 | 10/2010 | Braunschweiler et al. |
| 2010/0268284 A1 | 10/2010 | Bankoski |
| 2010/0298647 A1 | 11/2010 | Black |
| 2010/0298654 A1 | 11/2010 | Gray |
| 2010/0312068 A1 | 12/2010 | Dalton |
| 2010/0331849 A1* | 12/2010 | Riesinger ......... A61B 17/7077 606/90 |
| 2010/0331901 A1 | 12/2010 | Iott |
| 2011/0004067 A1 | 1/2011 | Marchek |
| 2011/0022088 A1 | 1/2011 | Forton |
| 2011/0034780 A1 | 2/2011 | Loftus |
| 2011/0034781 A1 | 2/2011 | Loftus |
| 2011/0130634 A1* | 6/2011 | Solitario, Jr. ...... A61B 17/3421 600/231 |
| 2011/0130793 A1 | 6/2011 | Woolley |
| 2011/0137130 A1 | 6/2011 | Thalgott et al. |
| 2011/0172494 A1 | 7/2011 | Bass et al. |
| 2011/0201897 A1 | 8/2011 | Bertagnoll |
| 2011/0208008 A1 | 8/2011 | Michaeli |
| 2011/0224496 A1 | 9/2011 | Weiran |
| 2011/0224497 A1 | 9/2011 | Weiman et al. |
| 2011/0245836 A1 | 10/2011 | Hamada |
| 2011/0257487 A1 | 10/2011 | Thalgott |
| 2011/0301422 A1 | 12/2011 | Woolley et al. |
| 2011/0301423 A1 | 12/2011 | Koros et al. |
| 2012/0065693 A1 | 3/2012 | Lim et al. |
| 2012/0245431 A1 | 9/2012 | Baudouin et al. |
| 2012/0271364 A1 | 10/2012 | Sharifi-Mehr et al. |
| 2012/0283521 A1 | 11/2012 | Smith |
| 2012/0303034 A1 | 11/2012 | Woolley et al. |
| 2013/0245383 A1 | 9/2013 | Friedrich |
| 2014/0066718 A1 | 3/2014 | Fiechter et al. |
| 2014/0107656 A1 | 4/2014 | Masson et al. |
| 2014/0135584 A1 | 5/2014 | Lee et al. |
| 2015/0313585 A1 | 11/2015 | Abidin et al. |
| 2016/0106408 A1 | 4/2016 | Ponmudi et al. |
| 2016/0331361 A1 | 11/2016 | Masson et al. |
| 2017/0035406 A1 | 2/2017 | Abidin et al. |
| 2017/0143323 A1 | 5/2017 | Cryder et al. |
| 2017/0196597 A1 | 7/2017 | Corbin |
| 2017/0265850 A1 | 9/2017 | Cryder et al. |
| 2017/0273677 A1 | 9/2017 | Gorek et al. |

FOREIGN PATENT DOCUMENTS

| | | |
|---|---|---|
| EP | 2272437 | 1/2011 |
| FR | 2788958 | 8/2000 |
| GB | 1520832 | 8/1978 |
| JP | 10277043 A | 10/1998 |
| JP | 2007502175 A | 2/2007 |
| WO | 9838921 | 9/1998 |
| WO | 1998038921 | 9/1998 |
| WO | 2001006940 A1 | 2/2001 |
| WO | 2007121271 | 10/2007 |
| WO | 2008082836 | 7/2008 |
| WO | 2008130548 | 10/2008 |
| WO | 2008131084 | 10/2008 |
| WO | 2010057980 | 5/2010 |
| WO | 2011112878 | 9/2011 |
| WO | 2012026981 A1 | 3/2012 |

OTHER PUBLICATIONS

Deutsch and Musacchio, "Minimally invasive transforaminal lumbar interbody fusion with unilateral pedicle screw fixation," Neurosurg Focus, 2006 20(3): E10, 5 pages.

Dhall et al., "Clinical and Radiographic comparison of Mini-open Transforaminal Lumbar Interbody Fusion With Open Transforaminal Lumbar Interbody Fusion in 42 Patients with Long Term Follow-up," J. Neurosurg Spine, 2008, 9: 560-565.

Holly et al., "Minimally Invasive Transformainal Lumbar Interbody Fusion: indications, technique, and Complications," Neurosurg Focus, 2006, 20:E6, 5 pages.

International Search Report and Written Opinion from PCT/US2010/002951, dated Mar. 23, 2011, 19 pages.

Mummaneni and Rodts, "The mini-open transforminal Lumbar Interbody Fusion" Neurosurgery, 2005, S7:256-261.

Ozgur et al., "Minimally Disruptive Decompression and Transforaminal Lumbar Interbody Fusion," The Spine Journal, 2006, 6: 27-33.

Ozgur et al., "Minimally-invasive Technique for Transforaminal Lumbar Interbody Fusion (TLIF)," Eur Spine J, 2005, 14: 887-894.

Schwender et al., "Minimally invasive transforaminal lumbar interbody fusion (TLIF): technical feasibility and initial results," J Spinal Disord Tech. 2005, 18(1):S1-S6.

* cited by examiner

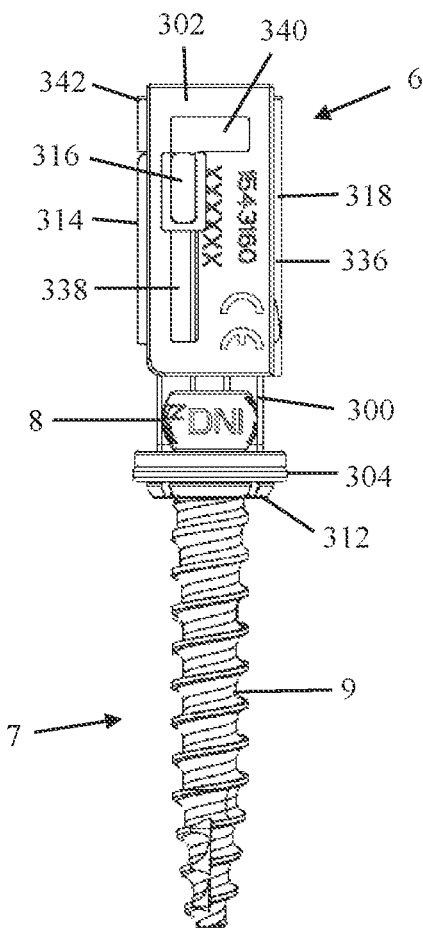 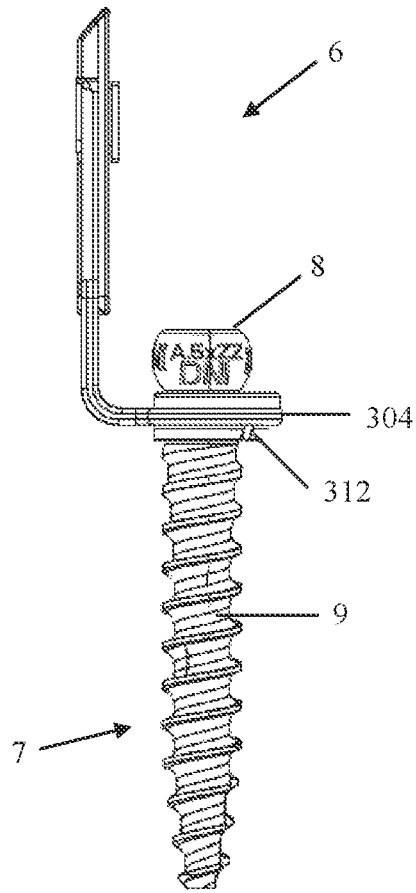
Fig. 35                    Fig. 36
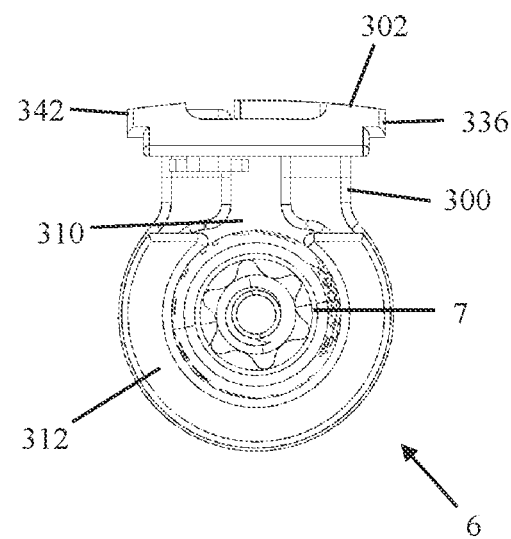
Fig. 37

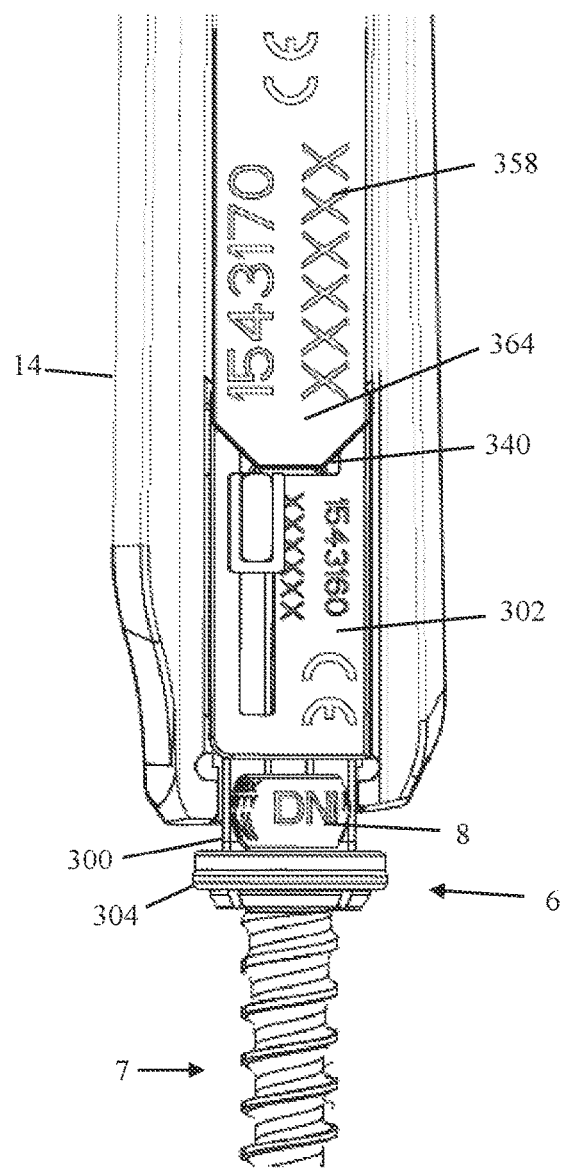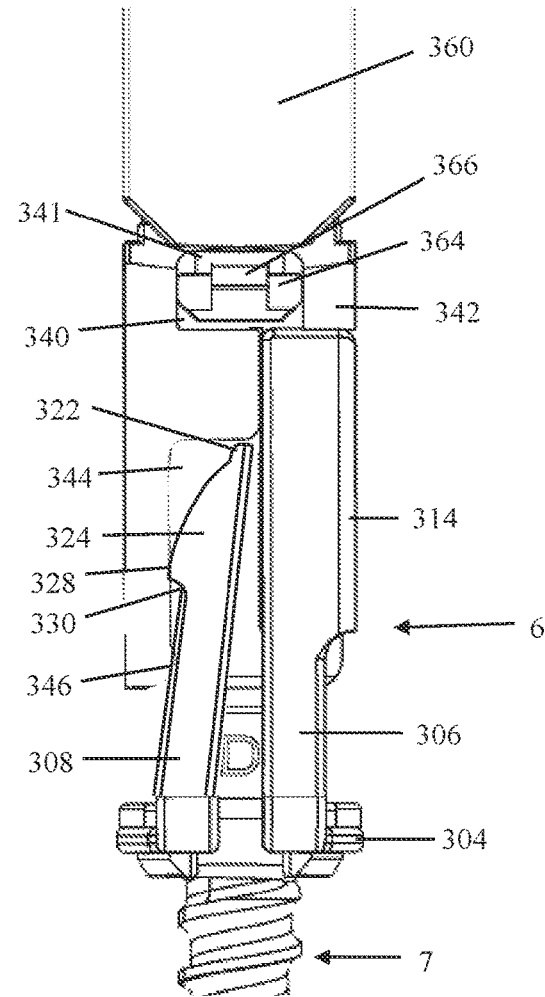
Fig. 43
Fig. 44

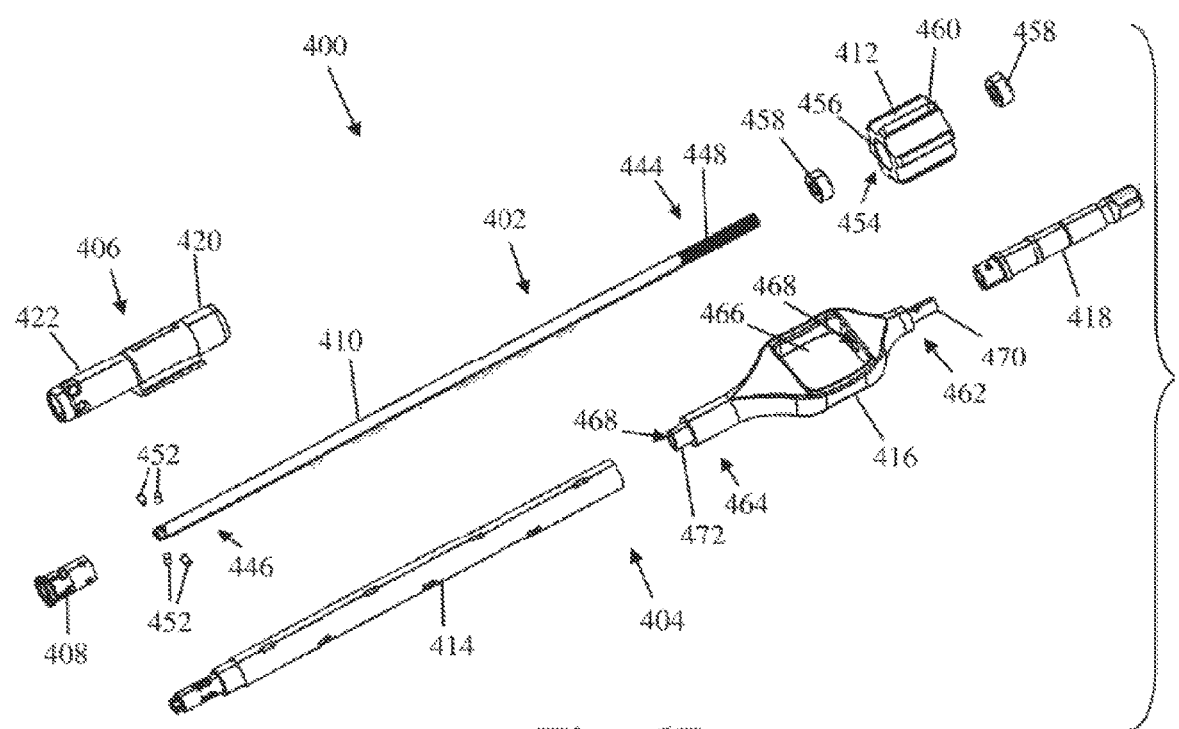
Fig. 67
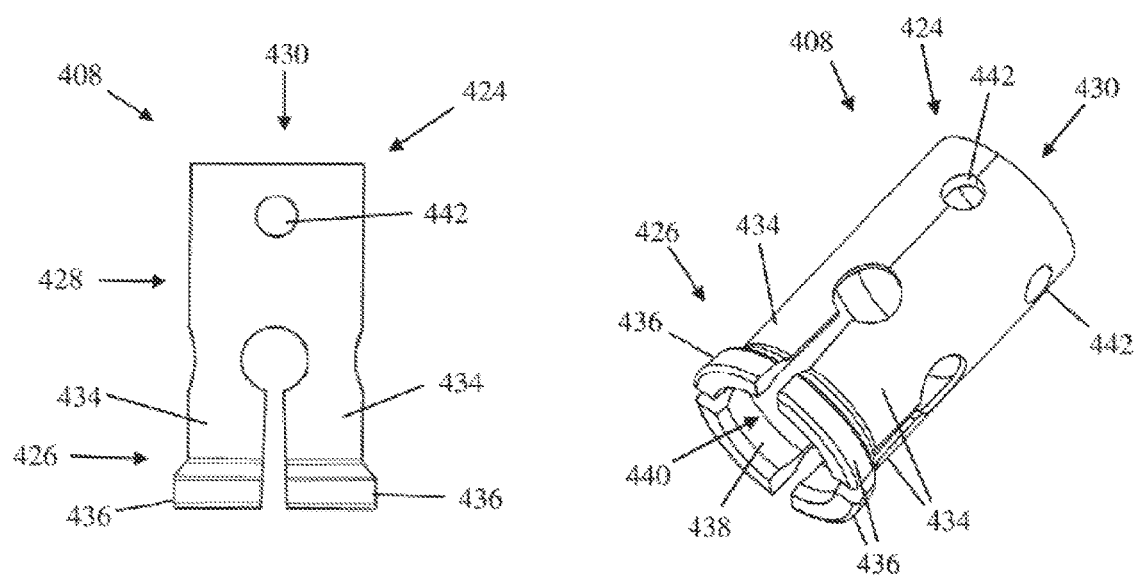
Fig. 68
Fig. 69

METHOD AND APPARATUS FOR PERFORMING SPINAL SURGERY

CROSS-REFERENCE TO RELATED APPLICATIONS

This application is a continuation of U.S. Ser. No. 17/193,927, filed Mar. 5, 2021, which is a continuation of U.S. Ser. No. 16/243,060, filed Jan. 8, 2019, which is a continuation of U.S. Ser. No. 15/394,156, filed Dec. 29, 2016, which is a division of U.S. Ser. No. 14/029,724, filed Sep. 17, 2013; which is a continuation of U.S. Ser. No. 13/204,583, filed Aug. 5, 2011 (now U.S. Pat. No. 8,535,320), which is a continuation of U.S. Ser. No. 12/927,415, filed on Nov. 10, 2010 (now U.S. Pat. No. 8,357,184), which claims the benefit of priority from U.S. provisional 61/259,825, filed Nov. 10, 2009. The contents of all of the foregoing are each incorporated herein by reference.

FIELD

This application relates to implants, instruments, and methods for performing surgical procedures on the spine, including one or more of creating an operative corridor to the spine, delivering implants to the spine, fusing one or more segments of the spine, and fixing one or more segments of the spine.

BACKGROUND

Spinal discs serve to cushion and stabilize the spine in addition to distributing stress and damping cyclic loads. The discs may become damaged due to injury or age and symptoms of a damaged disc may include severe pain, numbness or muscle weakness. Fusion is one method of reducing the magnitude of the symptoms of damaged spinal discs, or for any pathology that would suggest direct spinal decompression as a treatment. The primary goals of fusion procedures are to provide stability between the vertebrae on either side of the damaged disc and to promote natural fusion of those adjacent vertebrae. One of the most common fusion techniques utilized is the transforaminal lumbar interbody fusion (TLIF) in which the intervertebral disc space is accessed and operated on through a posterolateral approach. Generally, the TLIF procedure is performed through an "open" approach requiring a large incision and the separation and/or cutting of muscle and tissue, resulting in long recovery times and post-operative pain related to the procedure. To reduce the drawbacks associated with open procedures, minimally invasive techniques that reduce incision size and muscle cutting are becoming more popular. However, working through the smaller exposures brings other challenges, for example, decreased visualization and decreased flexibility in manipulating surgical instruments, among others, and thus the skill, training, and experience required for performing minimally invasive TLIF procedures is significantly higher than for open surgeries. A need therefore exists for improvements relating to the performance of minimally invasive TLIF procedures. The instruments and methods described herein are directed to addressing these needs.

SUMMARY

The present application describes implants, instruments, and methods for performing surgical procedures on the spine, including one or more of creating an operative corridor to the spine, delivering implants to the spine, fusing one or more segments of the spine, and fixing one or more segments of the spine.

According to one example, there is described a first method for attaching a fixation system to the spine of a patient. The fixation system includes at least two bone anchors and a spinal rod linking the at least two bone anchors. The method includes connecting a first bone anchor to a first retractor blade, advancing the first bone anchor and first retractor blade together to a first spinal bone, and anchoring the first bone anchor to the first spinal bone. The method also includes connecting a second bone anchor to a second retractor blade, advancing the second bone anchor and second retractor blade together to a second spinal bone, and anchoring the second bone anchor to the second spinal bone. The method also includes connecting a retractor body to the first retractor blade and the second retractor blade and operating the retractor body to expand an operative corridor formed between the first retractor blade and second retractor blade from the skin level of the patient to the spine. The method also includes linking the first bone anchor and the second bone anchor with a spinal rod.

According to another aspect of the first method the spinal bone is a first vertebra and the second spinal bone is a second vertebra separated from the first vertebra by an intervertebral disc space, and wherein the first spinal bone, second spinal bone, and intervertebral disc space comprise a first spinal level.

According to another aspect of the first method the first bone anchored is anchored through a pedicle of the first vertebra and the second bone anchor is anchored through a pedicle of the second vertebra.

According to another aspect of the first method, the method may further include adjusting the angle of the operative corridor.

According to another aspect of the first method, the first method may be performed wherein the angle of the operative corridor is adjusted until the operative corridor is parallel to the intervertebral disc space.

According to another aspect of the first method, adjusting the angle of the operative corridor is accomplished by moving a proximal end of the first retractor blade and a proximal end of the second retractor blade in the same direction while a distal end of the first retractor blade remains in the same general position adjacent the first pedicle and a distal end of the second retractor blade remains in the same general position adjacent the second pedicle.

According to another aspect of the first method the angle of the operative corridor is adjusted in one of a cephalad or caudal direction.

According to another aspect of the first method the angle of the operative corridor is adjusted in one of an anterior and posterior direction.

According to another aspect of the first method the angle of the operative corridor is adjusted in both one of a cephalad and caudal direction and in one of an anterior and posterior direction.

According to another aspect of the first method the first retractor blade is connected to the first bone anchor in a polyaxial engagement and the second retractor blade is connected to the second bone anchor in a polyaxial engagement.

According to another aspect of the first method the first bone anchor is connected to the first retractor blade via a first hoop shim slidably engaged to an interior surface of said first retractor blade and the second anchor is connected to the second retractor blade by a second hoop shim slidably engaged to an interior surface of said second retractor blade.

According to another aspect of the first method each of the first hoop shim and the second hoop shim include a shim portion that slidably engage the respective retractor blade and a hoop portion that receives a head a respective bone anchor therethrough.

According to another aspect of the first method each of the first hoop shim and the second hoop shim have an unlocked configuration that allows the head of the respective bone screw to pass therethrough and a locked configuration wherein the head of the respective bone screw is secured to the hoop shim.

According to another aspect of the first method the retractor body is further operated to distract the intervertebral disc space.

According to another aspect of the first method, the method may include advancing a third retractor blade towards the spine, connecting the third retractor blade to the retractor body, and operating the retractor body to expand the size of the operative corridor.

According to another aspect of the first method, the method may include advancing a third retractor blade towards the spine, connecting the third retractor blade to the retractor body, and operating the retractor body to further expand the size of the operative corridor.

According to another aspect of the first method the first and second retractor blades expand the operative corridor in cranially and caudally and the third retractor blade expands the operative corridor medially.

According to another aspect of the first method the third retractor blade clears tissue from the facet, lamina, and base of the spinous process as the third retractor blade retracted medially.

According to another aspect of the first method the third blade follows the topography of the facet, lamina, and base of the spinous process as the third retractor blade is retracted medially.

According to another aspect of the first method the third retractor blade includes a floating blade extension with a serrated distal end that curves to form a concave backward facing lip.

According to another aspect of the first method, the method may include applying downward pressure to the floating blade extension of the third retractor blade as the third retractor blade is retracted medially to facilitate clearing of the tissue from the facet, lamina, and base of the spinous process.

According to another aspect of the first method anchoring the first bone anchor to the first spinal bone comprises advancing a first anchor portion into said first spinal bone and subsequently attaching a first receiver portion to the first anchor portion and anchoring the second bone anchor to the second spinal bone comprises anchoring a second anchor portion to the second spinal bone and subsequently attaching a second receiver portion to the second anchor portion.

According to another aspect of the first method the first anchor portion is connected to the first retractor blade via a first hoop shim having a shim element that slidably engages the first retractor blade and a hoop element the secures the first anchor element, and wherein the second anchor portion is connected to the second retractor blade via a second hoop shim having a shim element that slidably engages the second retractor blade and a hoop element the secures the second anchor portion.

According to another aspect of the first method, the method may include removing the first hoop shim from the first anchor portion prior to attaching the first receiver to the first anchor portion and removing the second hoop shim from the second anchor portion prior to attaching the second receiver to the second anchor portion.

According to another aspect of the first method, the method may include operating on the first spinal level through the operating corridor prior to linking the first bone anchor and the second bone anchor with the spinal rod.

According to another aspect of the first method operating on the first spinal level includes one or more of a facetectomy, decompression, annulotomy, and discectomy.

According to another aspect of the first method at least a discectomy is performed and an implant is inserted into the intervertebral space after the discectomy.

According to another aspect of the first method the implant is positioned obliquely within the intervertebral space.

According to another aspect of the first method, the method may include operating the retractor body to distract the intervertebral disc space prior to performing the discectomy.

According to another aspect of the first method operating the retractor body to distract the intervertebral space includes advancing a first bolt disposed through a portion of the first retractor blade into contact with the retractor body to prevent inward tilting of the first retractor blade, advancing a second bolt disposed through a portion of the second retractor blade into contact with the retractor body to prevent inward tilting of the second retractor blade, and rotating a knob to increase the distance between a first arm of the retractor body engaged to the first retractor blade and a second arm of the retractor blade engaged to the second retractor blade.

According to another aspect of the first method the first retractor blade and the second retractor blade may be different lengths.

According to another aspect of the first method, the method may include connecting a third bone anchor to a fourth retractor blade, advancing the third bone anchor and fourth retractor blade together to a third pedicle adjacent the second pedicle, anchoring the third bone anchor to the third pedicle, and linking the third bone anchor together with the first bone anchor and second bone anchor with the spinal rod, wherein the third pedicle is part of a third spinal bone separated from the second spinal bone by a second intervertebral disc space, and wherein the second spinal bone, third spinal bone, and second intervertebral disc space comprise a second spinal level.

According to another aspect of the first method the steps of connecting a third bone anchor to a fourth retractor blade, advancing the third bone anchor and fourth retractor blade together to a third pedicle adjacent the second pedicle, and anchoring the third bone anchor to the third pedicle are performed after positioning the implant in the intervertebral disc space and before linking the first bone anchor, second bone anchor and third bone anchors with the spinal rod.

According to another aspect of the first method the first bone anchor includes a first anchor portion and a first receiver that is attached to the first anchor portion after the first anchor portion is anchored in the first pedicle, the second bone anchor includes a second anchor portion and a second receiver that is attached to the second anchor portion after the second anchor portion is anchored in the second pedicle, and the third bone anchor includes a third anchor portion and a third receiver that is attached to the third anchor portion after the third anchor portion is anchored in the third pedicle.

According to another aspect of the first method the first anchor portion is connected to the first retractor blade via a first hoop shim having a shim element that slidably engages the first retractor blade and a hoop element that secures the first anchor element, wherein the second anchor portion is connected to the second retractor blade via a second hoop shim having a shim element that slidably engages the second retractor blade and a hoop element that secures the second anchor portion, and wherein the third anchor portion is connected to the fourth retractor blade via a third hoop shim having a shim element that slidably engages the fourth retractor blade and a hoop element that secures the third anchor portion.

According to another aspect of the first method, the method may include disconnecting the first retractor blade and the second retractor blade from the retractor body and reconnecting the retractor body to the second retractor blade and the fourth retractor blade and operating the retractor body to expand an operative corridor formed between the second retractor blade and the fourth retractor blade from the skin level of the patient to the spine.

According to another aspect of the first method the second retractor blade includes multiple connector elements such that the second retractor blade can be connected to the retractor body in both right-facing and left-facing directions.

According to another aspect of the first method, the method may include disconnecting the first retractor blade and the second retractor blade from the retractor body, replacing the second retractor blade with a fifth retractor blade, and reconnecting the retractor body to the fifth retractor blade and the fourth retractor blade and operating the retractor body to expand an operative corridor formed between the fifth retractor blade and the fourth retractor blade from the skin level of the patient to the spine.

According to another aspect of the first method replacing the second retractor blade with a fifth retractor blade includes the steps of removing the second retractor blade from a track insert connected to the second hoop shim and inserting the fourth retractor blade over the track insert.

According to another aspect of the first method, the method may include engaging a track guide to the track insert before removing the second retractor blade and inserting the fifth retractor blade along the track guide to facilitate engagement of the fifth retractor blade with the track insert.

According to another aspect of the first method, the method may include operating on the second spinal level through the operating corridor prior to linking the first bone anchor, second bone anchor, and third bone anchor with the spinal rod.

According to another aspect of the first method operating on the second spinal level includes performing one or more of a facetectomy, decompression, annulotomy, and discectomy.

According to another aspect of the first method at least a discectomy is performed and a second implant is inserted into the second intervertebral space after the discectomy.

According to another aspect of the first method a second implant is positioned obliquely within a second intervertebral space.

According to another aspect of the first method, the method may include operating the retractor body expand the operating corridor to reexpose the first bone anchor, disconnecting the second anchor portion and fifth blade, disconnecting the third anchor portion and fourth blade, and attaching the first receiver to the first anchor portion, attaching the second receiver to the second anchor portion, and attaching the third receiver to the third anchor portion, prior to linking the first bone anchor, second bone anchor, and third bone anchor with the spinal rod.

According to another example, there is described a second method for performing a spinal fusion procedure on a spinal segment of a human spine, the spinal segment including at least a first vertebra and a second vertebra separated from the first vertebra by an intervertebral disc space, including the steps of (a) anchoring a first anchor portion to a first pedicle, the first anchor portion being connected to a first retractor blade of a retractor assembly; (b) anchoring a second anchor portion to a second pedicle, the second anchor portion being connected to a second retractor blade of the retractor assembly; (c) connecting the first retractor blade to a first arm of a retractor body of the retractor assembly and connecting the second retractor blade to a second arm of the retractor body; (d) operating the retractor body to increase the distance between the first arm and the second arm to expand an operating corridor between the first retractor blade and the second retractor blade; (e) advancing a third retractor blade through the operative corridor to the spinal segment; connecting the third retractor blade to a translating arm of the retractor body, and operating the retractor body to translate the translating arm and further expand the size of the operating corridor; (f) preparing the intervertebral disc space to receive an implant; (g) implanting a fusion implant in the intervertebral disc space; (h) disconnecting the first retractor blade from the first anchor portion and attaching a first receiver portion to the first anchor portion; (i) disconnecting the second retractor blade from the second anchor portion and attaching a second receiver portion to the second anchor portion; (j) inserting and locking a rod into the first receiver portion and second receiver portion; and (k) removing the first and second retractor blades from the operative corridor and closing the operative corridor.

According to another aspect of the second method the first anchor portion is connected to the first retractor blade via a hoop shim slidably engaged with the first retractor blade.

According to another aspect of the second method the second anchor portion is connected to the second retractor blade via a hoop shim slidably engaged with the second retractor blade.

According to another aspect of the second method, the method may include connecting the first anchor portion to the first retractor blade by inserting a head of the first anchor portion into a hoop member of the hoop shim and engaging a shim element of the hoop shim to the first retractor blade and connecting the second anchor portion to the second retractor blade by inserting a head of the second anchor portion into a hoop element of a hoop shim and engaging a shim element of the hoop shim to the second retractor blade.

According to another aspect of the second method engaging a shim element of a hoop shim to one of the first and second retractor blades includes inserting the shim element into a track formed along an interior face of the retractor blade and sliding the shim element down the track until the shim element sits in a distal most position along the track.

According to another aspect of the second method stops at the distal end of the track prevent the hoop shim from disengaging the retractor blade from the distal end of the blade.

According to another aspect of the second method, may include manipulating the hoop shim connected to one of the first and second anchor portions into a locked configuration that prevents disassociation of the anchor portion and the hoop shim.

According to another aspect of the second method manipulating the hoop shim into a locked position includes slidably advancing a hoop portion of the hoop shim towards the shim element.

According to another aspect of the second method slidably advancing the hoop portion towards the shim element causes a flange of the hoop portion to deflect inwards which causes a dimension of an anchor head receiving aperture in the hoop member to decrease.

According to another aspect of the second method the hoop shim is manipulated into the locked position after the hoop shim is inserted into a track formed along an interior face of one of the first and second retractor blades and advanced down the track to a distal end of the retractor blade.

According to another aspect of the second method may include connecting an inserter to the one of the first bone anchor first retractor blade and second bone anchor second retractor blade combinations According to another aspect of the second method the shim elements slidably engage.

According to another example, a first system includes a retractor for performing and creating an operative corridor to a surgical target site is described. The system includes a retractor body which includes a first arm; a second arm, the first arm and the second arm being movable relative to each other in a first direction; and a center arm movable relative to the first arm and the second arm in a second direction orthogonal to the first direction; a first retractor blade attachable to first arm; a second retractor blade attachable to the second arm; and a third retractor blade attachable to the center arm, wherein the third retractor blade is pivotable relative to the center arm in the first direction.

According to another aspect of the first system the first and second retractor blades are registerable to first and second pedicle of the spine.

According to another aspect of the first system the first and second retractor blades are registerable to the spine via a poly axial engagement.

According to another aspect of the first system the poly axial engagement is with a hoop shim.

According to another example, a second system for creating an operative corridor to a surgical target site is described. The second system includes a retractor body, the retractor body including a first arm; a second arm, the first arm and the second arm being movable relative to each other in a first direction; and a center arm movable relative to the first arm and the second arm in a second direction orthogonal to the first direction. The second system also includes a first retractor blade attachable to first arm; a second retractor blade attachable to the second arm; and a third retractor blade attachable to the center arm, wherein a distal end of the first retractor blade is configured to be temporarily anchored in position relative to a first spinal bone and a proximal end of the first retractor blade is pivotable relative to the first arm, and wherein a distal end of the first retractor blade is configured to be temporarily anchored in position relative to a second spinal bone and a proximal end of the second retractor blade is pivotable relative to the second arm.

According to another example, a third system is described including a hoop shim for use with a surgical tissue retractor system. The hoop shim includes a shim portion having at least one feature that releasably associates with a retractor blade of the surgical retractor system; and a hoop portion having a hoop member that releasably associates with the head of a bone anchor.

According to another aspect of the third system the hoop portion and the shim portion are slidably engaged.

According to another aspect of the third system the hoop member extends orthogonally to the shim portion.

According to another aspect of the third system the hoop member has an unlocked position which allows passage of the bone anchor head and a locked position which prevents passage of the bone anchor head.

According to another aspect of the third system the shim portion and the hoop portion are slidably engaged and the locked position is entered by sliding the hoop portion towards a proximal end of the shim portion.

According to another aspect of the third system sliding the hoop portion towards the proximal end of the shim portion causes a dimension of an aperture formed through the hoop member to decrease in size.

According to another aspect of the third system the hoop portion includes a first flange and a second flange extending from the hoop member.

According to another aspect of the third system the first flange slides within a recess formed in the back of the shim element.

According to another aspect of the third system the first flange has a wing extension along at least portion of the first flange extending beyond a perimeter of the recess in the back of the shim element, the wing extension being receivable within a track groove of the retractor blade.

According to another aspect of the third system the second flange also slides within the recess formed in the back of the shim element.

According to another aspect of the third system the second flange includes a proximal portion having a first width and an intermediate portion having a width greater than the first width of the proximal portion.

According to another aspect of the third system the proximal portion always resides within the recess in the back of the shim element.

According to another aspect of the third system the intermediate portion resides outside the recess when the hoop portion is in the unlocked position and resides in the recess when the hoop portion is in the locked position.

According to another aspect of the third system the intermediate portion has a sloped upper surface that engages a knob situated at the entrance such that second flange deflects toward the first flange when the hoop portion slides into the recess.

According to another aspect of the third system deflection of the second flange causes a dimension of an aperture formed through the hoop member to decrease in size.

According to another aspect of the third system deflection of the second flange causes a slight rotation of the shim element relative to the first flange such that a distal end of the shim element flares out to the side opposite the first flange and such that a width between the distal end of a wing extension on the first flange and distal end of a wing extension on the shim element is greater than the width at an entrance between a first track groove and a second track groove of the retractor blade thereby preventing the hoop shim from being slidably engaged to the retractor blade when the hoop shim is locked.

According to another aspect of the third system the intermediate portion has bottom portion sloped in the opposite direction of the slopped top portion that permits the intermediate portion to slide out of the recess.

According to another aspect of the third system the bottom surface is steeper than the slope of the top surface.

According to another aspect of the third system the sloped top surface of the intermediate element is also concave.

According to another aspect of the third system the sloped bottom surface of the intermediate element is also convex.

According to another aspect of the third system the first flange includes a tab disposed through a slot formed in the shim portion.

According to another aspect of the third system a retaining plate on the tab fixes the hoop portion and the shim portion together.

According to another aspect of the third system the hoop member includes an insert.

According to another aspect of the third system the insert comprises a polymer material.

According to another aspect of the third system the polymer is polyetheretherkeytone.

According to another aspect of the third system when the hoop portion is releasably associated with the bone anchor, the association permits the bone anchor to angularly move relative to the hoop portion.

According to another aspect of the third system the association permits polyaxial angulation.

According to another aspect of the third system the polyaxial angulation encompasses 360 degrees.

According to another aspect of the third system the shim portion and the hoop portion are provided preassembled.

According to another aspect of the third system the shim portion has a horizontal slot formed near a proximal end.

According to another aspect of the third system the horizontal slot has a ramped back-facing surface.

According to another example, a fourth system is described including a retractor blade for use with a surgical tissue retractor system. The retractor blade includes an attachment portion, an upper blade portion that extends generally orthogonally from the attachment portion, and a lower blade portion that extends at an obtuse angle from the upper portion such that a distal end of the lower blade portion is offset from the plane of the upper portion.

According to another aspect of the fourth system the distal end of the lower portion is offset from the plane of the upper portion by approximately one-quarter inch.

According to another aspect of the fourth system the retractor blade is provided in multiple lengths and the angle at which the lower blade portion extends from the upper blade portion is varied to achieve a generally uniform offset.

According to another aspect of the fourth system the lower blade portion has a greater width than the upper blade portion.

According to another aspect of the fourth system the lower blade portion includes a free sliding blade extension.

According to another aspect of the fourth system the lower blade portion has a recess in which the free sliding blade extension slides.

According to another aspect of the fourth system the recess has an elongated central slot in which a guide extension of the blade extension is disposed.

According to another aspect of the fourth system the recess also includes side grooves in which the edges of the blade extension are received.

According to another aspect of the fourth system the length of the central slot determines the sliding distance of the blade extension.

According to another aspect of the fourth system the distal end of the blade extension is curved toward the exterior side of the retractor blade.

According to another aspect of the fourth system the distal end of the blade extension is also has a concave curve.

According to another aspect of the fourth system the edge of the distal end is serrated.

According to another aspect of the fourth system the attachment portion includes an engagement feature that pivotally engages a retractor body.

According to another aspect of the fourth system the engagement feature is a cylindrical aperture dimensioned to receive a cylindrical post of the retractor body.

According to another aspect of the fourth system the attachment portion includes a set screw extending into the cylindrical aperture to secure the retractor blade to the retractor body.

According to another aspect of the fourth system the attachment portion includes a second engagement feature that connects to an insertion handle.

According to another aspect of the fourth system the second engagement feature is a post with a tapered proximal end and a cylindrical groove that is configured to receive a coil spring that extends into in a cylinder dimensioned to receive the post.

According to still another example there is described a fifth system, the fifth system including an inserter for anchoring a bone anchor. The inserter includes a driver assembly having a driver shaft and a distal engagement feature that engages a drive feature of the bone anchor; and a blade engagement member that releasably engages a retractor blade of a retractor assembly.

According to another aspect of the fifth system the driver shaft freely rotates relative to the engagement member such that a retractor blade attached to the engagement member doesn't rotate with the bone anchor as the bone anchor is driven into bone.

According to another aspect of the fifth system the blade engagement member comprises a body with a pair of wing extensions that slidably engage a pair of track grooves along the interior face of the retractor blade.

According to another aspect of the fifth system the engagement member further comprises a deflectable tab configured to be received within notches in the retractor blade.

According to another aspect of the fifth system the system further comprises a receiver member that captures a head of the bone anchor.

According to another aspect of the fifth system the receiver member comprises a receptacle having deflectable flanges that deflect inward around the head of the bone anchor to secure the bone anchor to the receiver member.

According to another aspect of the fifth system a thumb wheel linked to the receiver member draws the deflectable fingers into a cylinder causing the fingers to deflect.

According to another aspect of the fifth system the distal engagement feature of the driver shaft is housed within the receptacle such that the distal engagement feature engages with the drive feature of the bone anchor head when the bone anchor head is secured in the receptacle.

According to another aspect of the fifth system the receptacle rotates with the driver shaft.

According to another aspect of the fifth system the driver shaft is cannulated.

According to another example there is described a sixth system including a bone anchor, a retractor blade, and a shim that can be assembled into an anchor-blade-shim assembly. The sixth system includes a bone anchor having an anchor portion that includes a partially spherical head; a retractor blade that is attachable to a retractor assembly, the retractor blade having a track including first and second track grooves formed in an interior face; and a shim that slidably engages the first and second track grooves such that it is advanceable down the track towards a distal end of the retractor blade and securely engages the partially spherical head of the bone anchor in a polyaxial engagement.

BRIEF DESCRIPTION OF THE DRAWINGS

Many advantages of the present invention will be apparent to those skilled in the art with a reading of this specification in conjunction with the attached drawings, wherein like reference numerals are applied to like elements and wherein:

FIGS. 35-37 are front plan, side plan and top plan views, respectively, of the hoop shim assembly of FIG. 31 in a locked position and engaged to a bone anchor forming part of the surgical fixation system of FIG. 1;

FIGS. 43-45 are font plan, back plan, and side plan views, respectively, of the hoop shim assembly locked and engaged with the bone anchor of FIG. 35 coupled to a retractor blade assembly of FIG. 22, and also coupled to the hoop shim removal tool of FIG. 40 prior to disengagement of the hoop shim assembly from the bone anchor;

FIG. 67 is an exploded perspective view of the inserter of FIG. 64;

FIGS. 68-70 are plan, perspective, and sectional views, respectively, of a receiver member forming part of the inserter of FIG. 64;

DESCRIPTION OF THE PREFERRED EMBODIMENT

Figure 1:
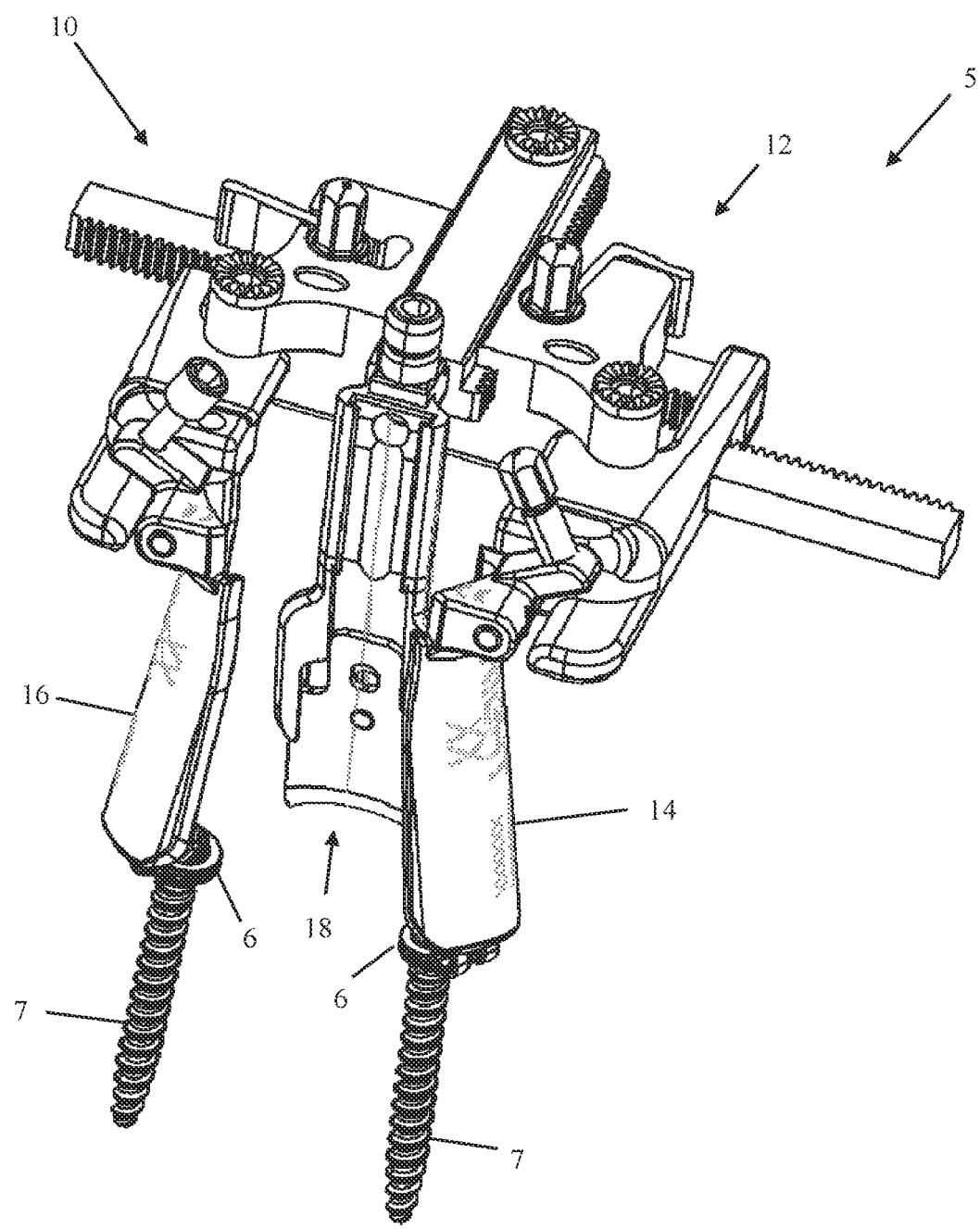
FIG. 1 is a perspective view of an example of a surgical fixation system according to one embodiment of the present invention.
Figure 2:
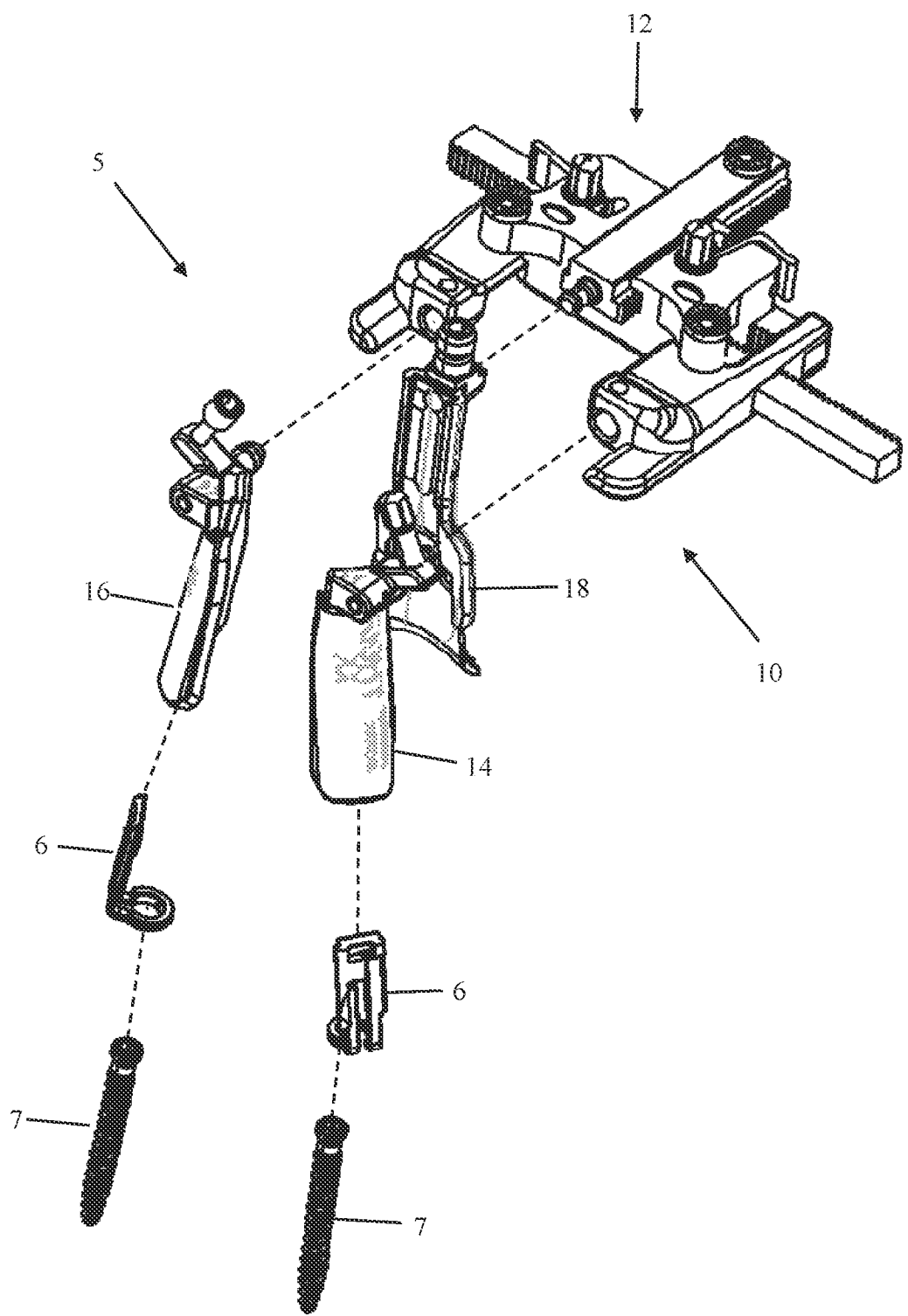
FIG. 2 is an exploded perspective view of the surgical fixation system of FIG. 1.
Figure 3:
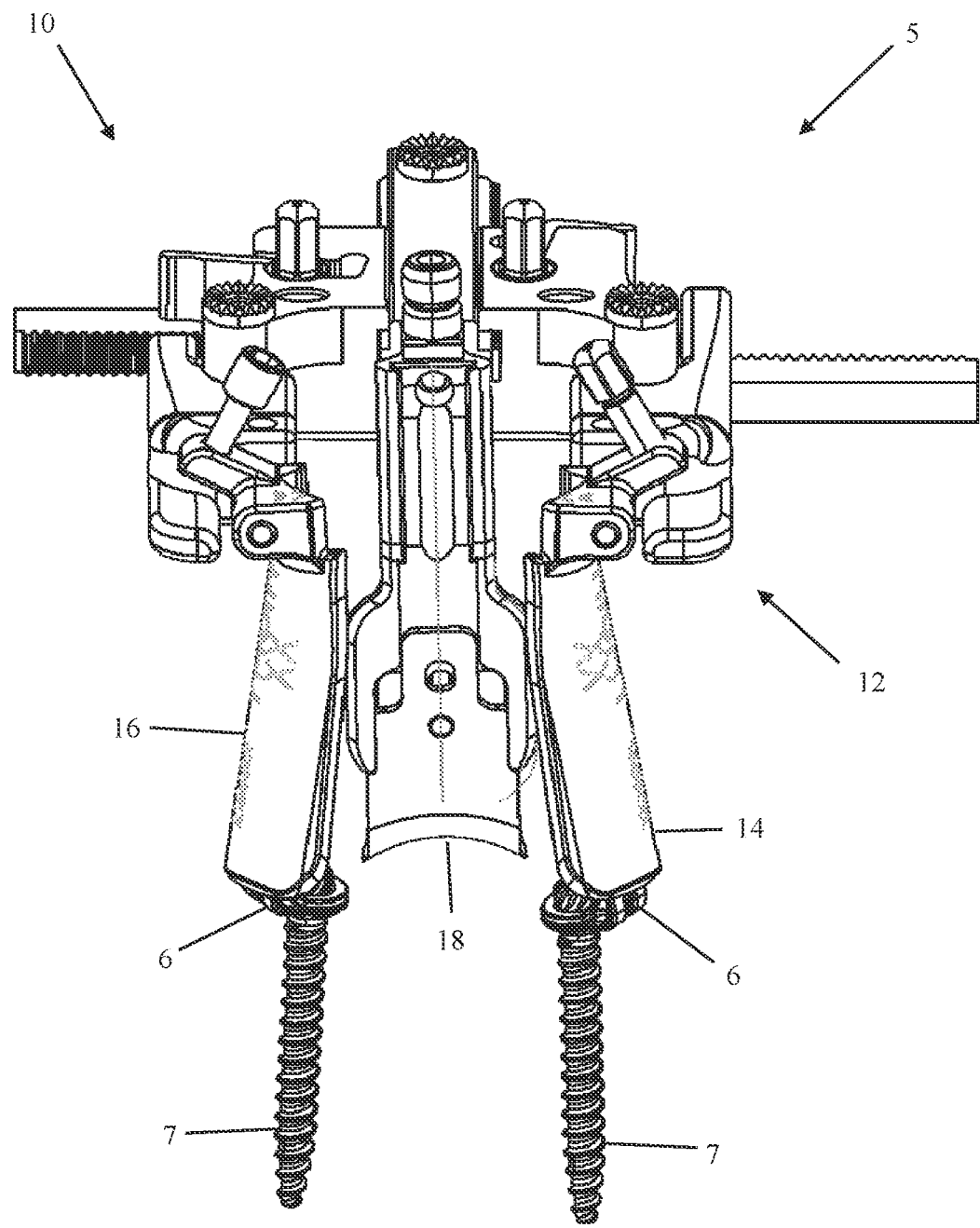
FIGS. 3-5 are front, perspective, and side views of the surgical fixation system of FIG. 1.
Figure 4:
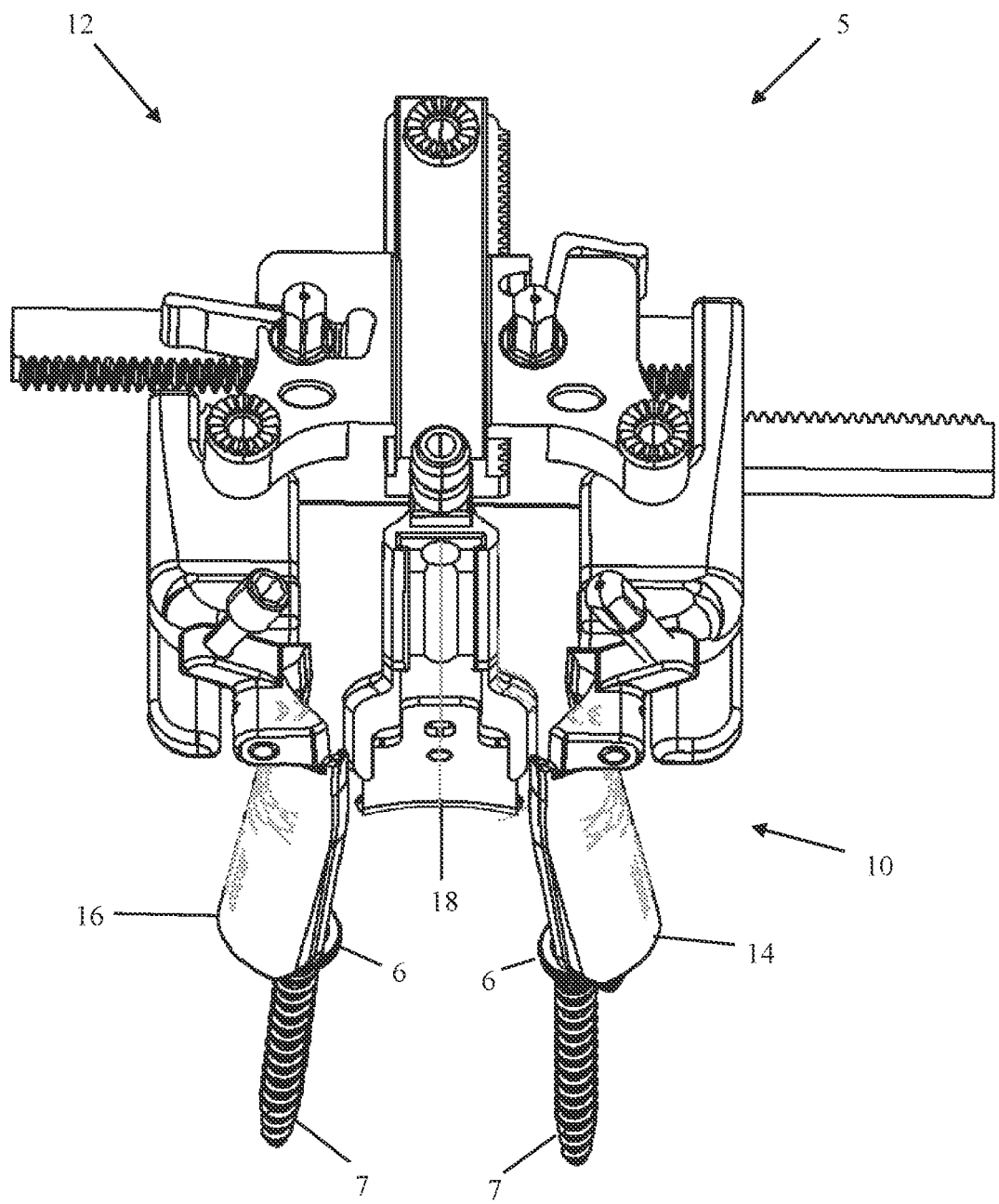
Figure 5:
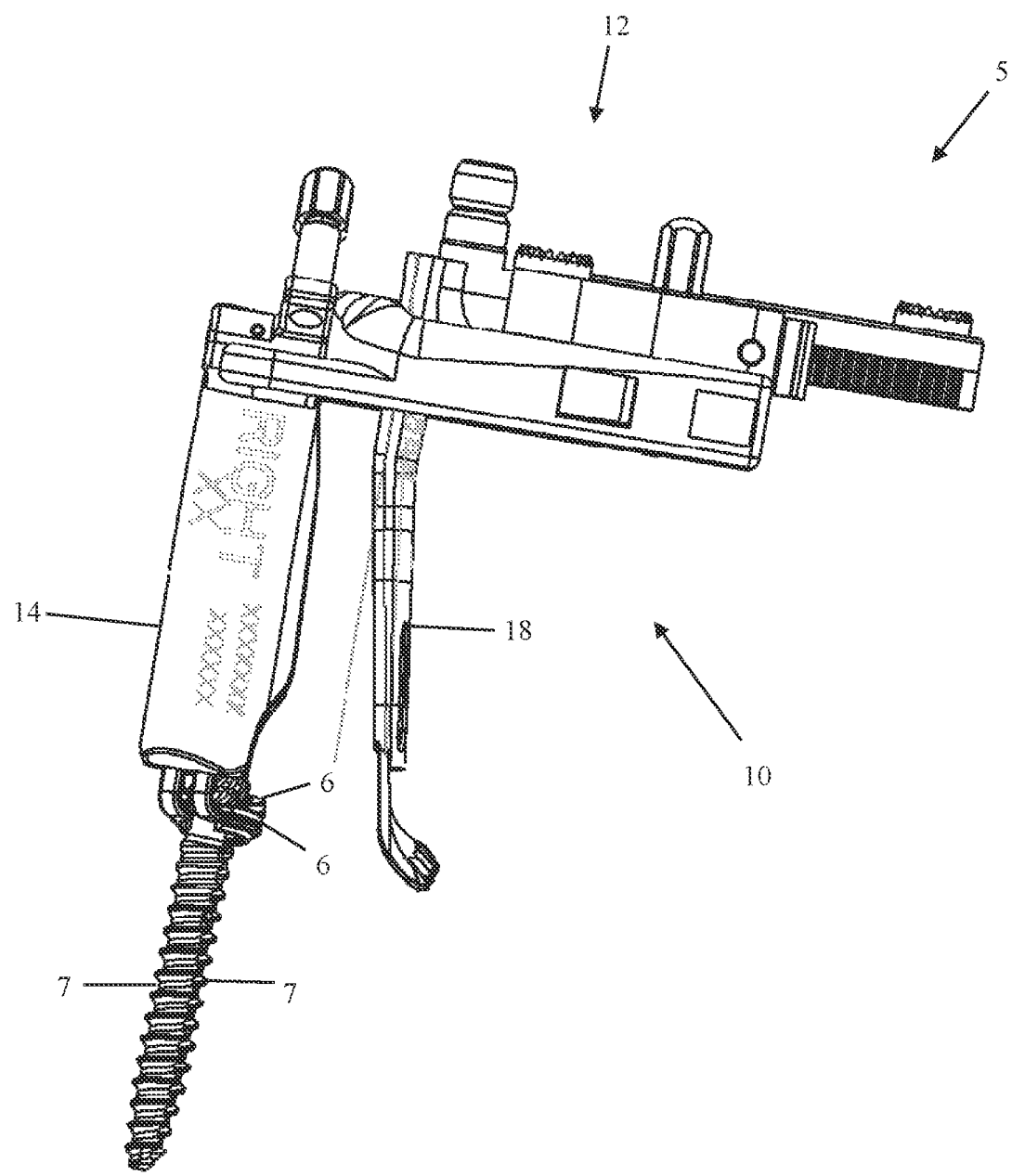

Illustrative embodiments of the invention are described below. In the interest of clarity, not all features of an actual implementation are described in this specification. It will of course be appreciated that in the development of any such actual embodiment, numerous implementation-specific decisions must be made to achieve the developers' specific goals, such as compliance with system-related and business-related constraints, which will vary from one implementation to another. Moreover, it will be appreciated that such a development effort might be complex and time-consuming, but would nevertheless be a routine undertaking for those of ordinary skill in the art having the benefit of this disclosure. The systems and methods for performing transforaminal lumbar interbody fusion disclosed herein boast a variety of inventive features and components that warrant patent protection, both individually and in combination.

FIGS. 1-5 illustrate an example of a surgical fixation system 5 according to one embodiment of the present invention. The surgical fixation system 5 includes a variety of sub-components dimensioned to allow for retraction of a soft tissue in order to establish an operative corridor through a patient's skin to a surgical target site. By way of example only, the surgical target site referred to herein throughout is an intervertebral disc space situated between two adjacent vertebrae. Although particularly suited for use in lumbar spine fixation, it will be readily appreciated by those skilled in the art that the surgical fixation system of the present invention may be employed in any number of suitable orthopedic fixation approaches and procedures, including but not limited to anterior, posterior, lateral, anterolateral, posterolateral, cervical spine fixation, thoracic spine fixation, as well as any non-spine fixation application such as bone fracture treatment.

By way of example only, the surgical fixation system 5 includes a tissue retraction assembly 10, a plurality of hoop shims 6, and a plurality of bone anchors 7. According to one broad aspect of the present invention, the tissue retraction system 10 includes retractor body 12, a first retractor blade 14, a second retractor blade 16, and a third retractor blade 18 (also referred to herein throughout as the medial blade 18). The retractor blades 14, 16, 18 may be provided in any size and shape suitable to establish and maintain an operative corridor to the surgical target site, however, certain benefits may be achieved utilizing one or more aspects of the various shaped retractor blades described, which features should be apparent from the discussion herein. The bone anchor 7 may be one of the type shown and described in U.S. patent application Ser. No. 12/820,136, filed Jun. 21, 2010 and entitled "Polyaxial Bone Screw Assembly," the entire contents are hereby incorporated by reference into this disclosure as if set forth fully herein.

The tissue retraction assembly 10 may be configured such that the retractor blades 14, 16, 18 may be advanced to the surgical target site individually (e.g. sequentially) or together (e.g. simultaneously). For example, for simultaneous advancement, two or more of the retractor blades 14, 16, 18 may be attached to the retractor body prior to advancement to a surgical target site. As will be explained by way of example in further detail below, the tissue retraction assembly 10 is particularly suitable for individual advancement of each blade 14, 16, 18 to a surgical target site. For instance, the first retractor blade 14 may be advanced through an incision and securely attached to a first bone segment within the surgical target site. The second retractor blade 16 may then be advanced through an incision and securely attached to a second bone segment within the surgical target site. Once the first and second retractor blades 14, 16 are secured to the first and second bone segments, the retractor blades 14, 16 may then be attached to the retractor body 12. Thereafter, the first and second retractor blades 14, 16 may be further moved by the retractor assembly to a second "open" position to establish and maintain a second operative corridor (or working channel). This operative corridor may be variable in size and approach angle to the surgical target site, providing the ability to establish numerous custom working channels. The medial retractor blade 18 may then be attached to the retractor body 12 and used as desired.

Figure 6:
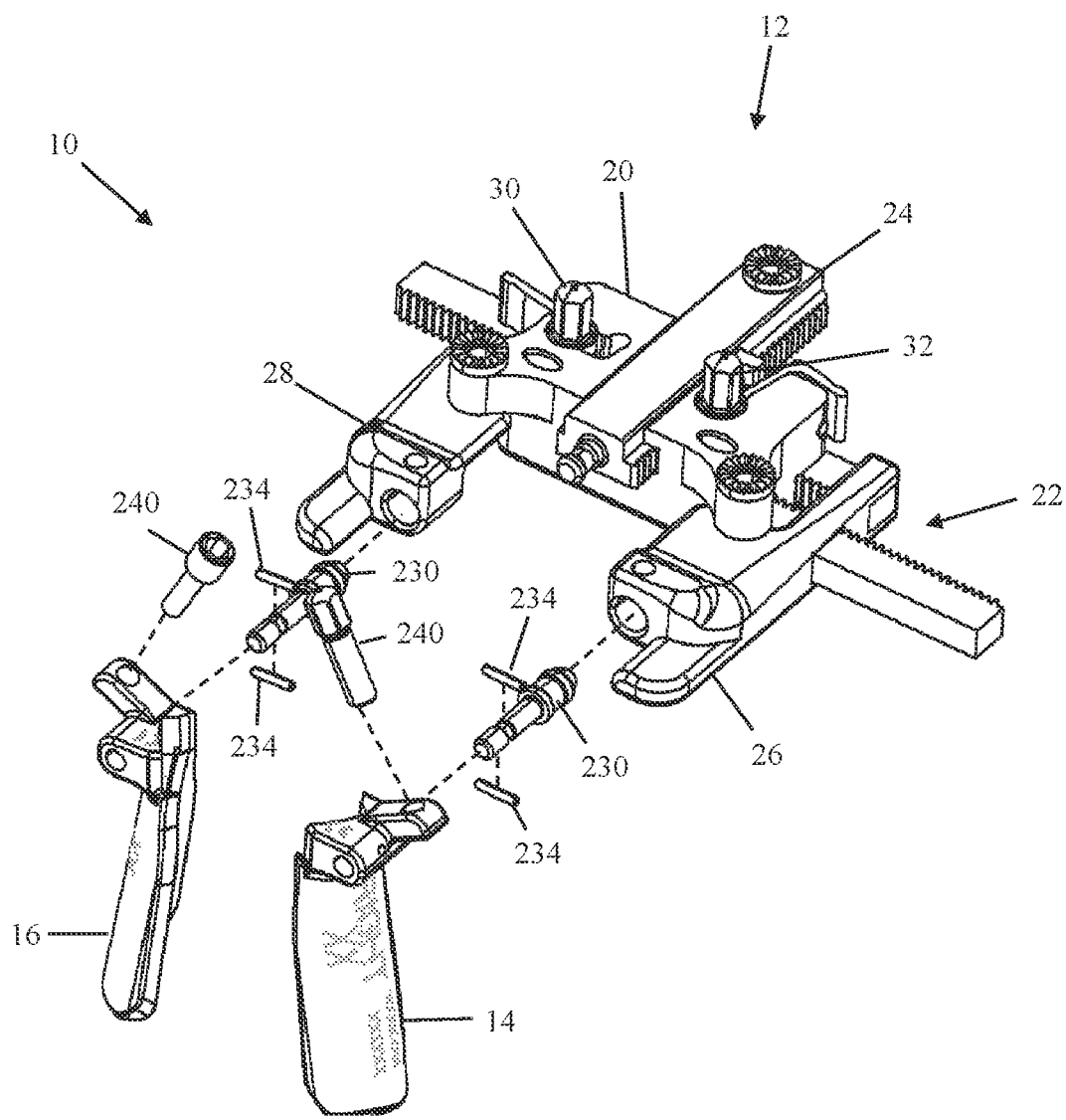
FIG. 6 is a partially exploded perspective view of an example of a tissue retraction system forming part of the surgical fixation system of FIG. 1.
Figure 7:
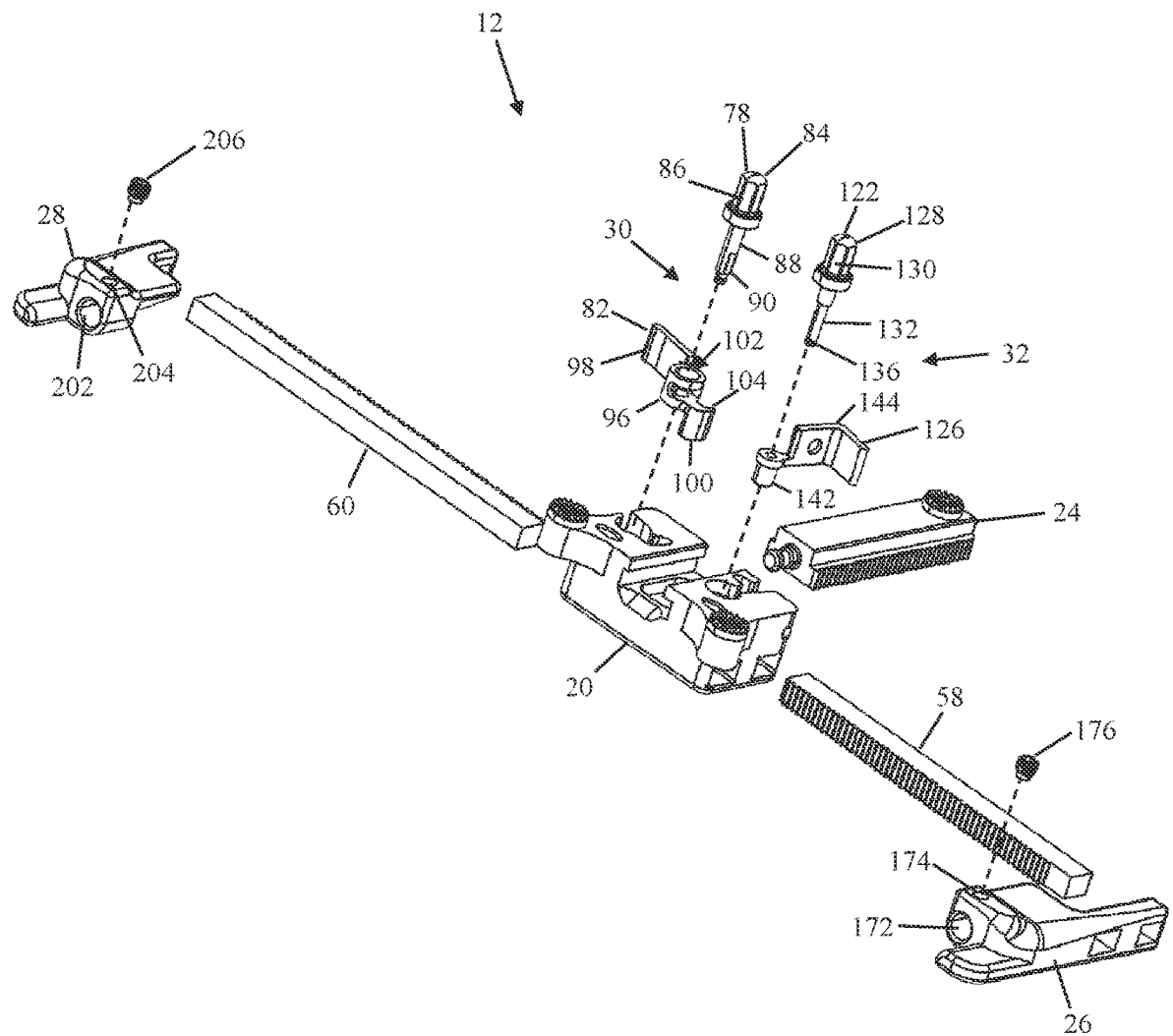
FIG. 7 is an exploded perspective view of an example of a retractor body forming part of the tissue retraction system of FIG. 6.
Figure 8:
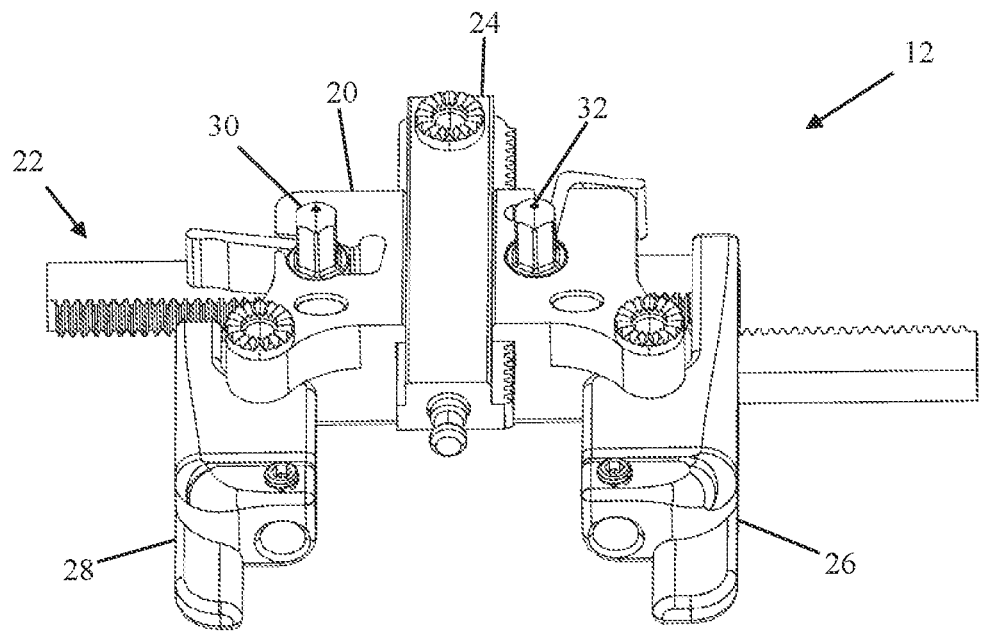
FIG. 8 is a front perspective view of the retractor body of FIG. 7.

Referring to FIGS. 6-8, the retractor body portion 12 includes a housing member 20, a rack member 22, a medial retraction member 24, a first retractor arm 26, a second retractor arm 28, a first toggle 30, and a second toggle 32. Broadly, the housing member 20 provides a scaffold to hold the various components together. The rack member 22 provides a mechanism to expand the operative corridor in a caudal-cranial direction by moving the retractor blades 14, 16 toward or away from one another. The medial retraction member 24 provides a mechanism to expand the operative corridor in a medial direction by moving the medial retractor blade 18 away from the first and second retractor blades 14, 16. The first retractor arm 26 couples to the first retractor blade 14, and as will be explained in detail below, is configured to enable the first retractor blade 14 to retract nearby soft tissue and/or distract the first bone segment. The second retractor arm 28 couples to the second retractor blade 16, and is configured to enable the second retractor blade 16 to retract nearby soft tissue and/or distract the second bone segment. The first toggle 30 controls the caudal-cranial movement of the first and second retractor arms 26, 28, and therefore the first and second retractor blades 14, 16. The second toggle 32 controls the medial movement of the medial retraction member 24, and therefore the medial blade 18.

Figure 9:
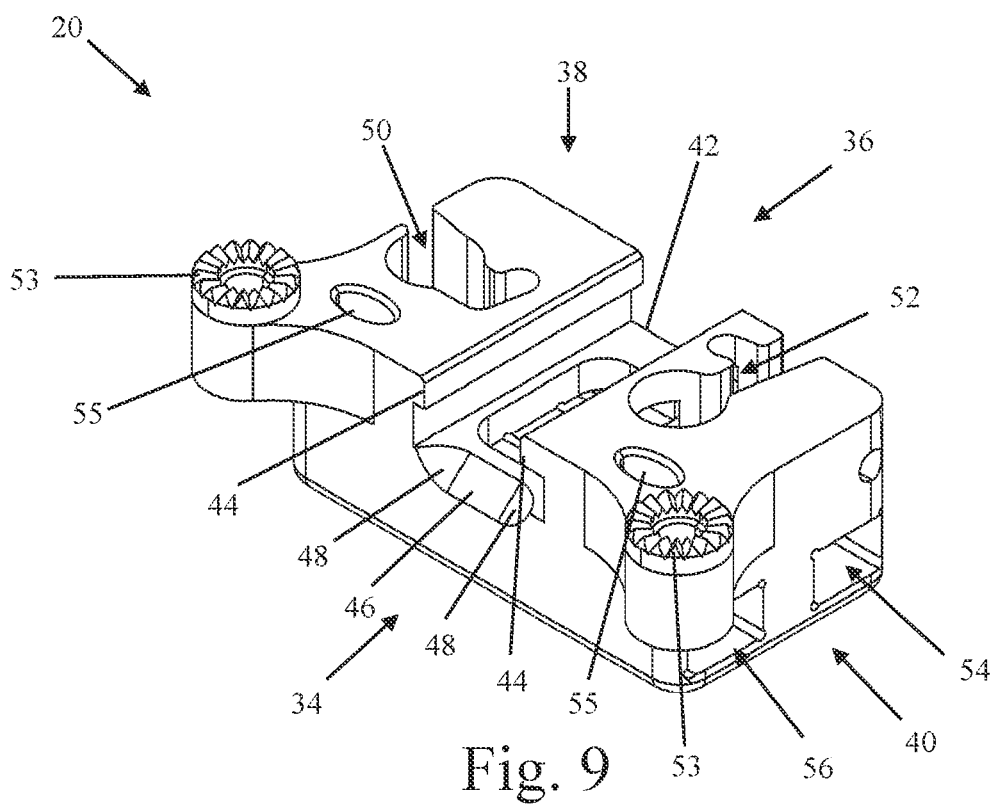
FIGS. 9-10 are front perspective and rear perspective views, respectively, of an example of a housing member forming part of the retractor body of FIG. 7.
Figure 10:
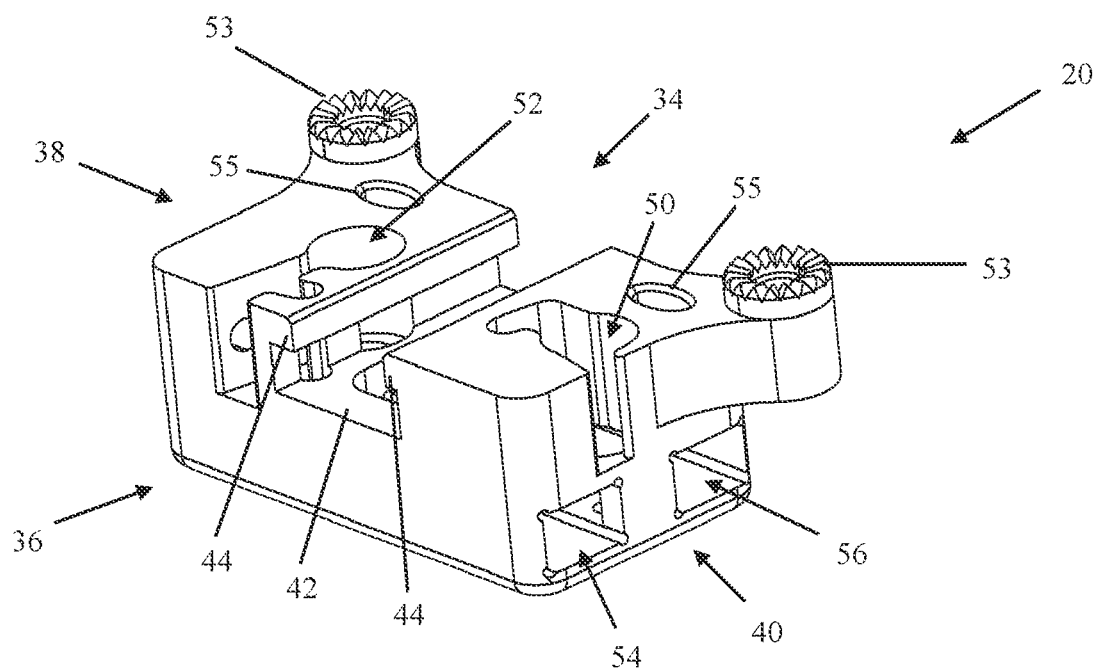

Referring now to FIGS. 9-10, the housing member 20 has a front side 34, a back side 36, an upper portion 38, and a lower portion 40. The housing member 20 further includes a first recess 42 extending axially through the upper portion 38 from the front side 34 to the back side 36. The first recess 42 is configured to receive the medial retraction member 24 therein. The first recess 42 include a pair of track grooves 44 that are configured to engage with flanges 110, 112 on the medial retraction member 24 to secure the medial retraction member to the housing 20. The first recess 42 further includes a tapered surface 46 extending from the front side of the first recess 42 toward the front side 34 of the housing member 20. This tapered surface 46 enables medial-lateral angulation of the medial retraction member 24 while in a retracted position. The tapered surface 46 is flanked by a pair of curved surfaces 48 that enable caudal-cranial pivoting of the medial retraction member 24 while in a retracted position. The upper portion 38 further includes a second recess 50 and a third recess 52, formed within the housing member 20 on either side of the first recess 42. The second recess 50 is configured to receive the first toggle 30 therein. The second recess 50 is dimensioned to allow for movement of the toggle therein to enable the toggle 30 to perform its function, which is explained in further detail below. The third recess 52 is configured to receive the second toggle 32 therein. The third recess 52 is dimensioned to allow for movement of the toggle 32 therein to enable the toggle 32 to perform its function, which is explained in further detail below. The upper portion 38 further includes at least one attachment member 53 dimensioned to enable attachment of the retractor body 12 to an articulating arm (not shown) within the operative field. This attachment to the articulating arm ensures that the surgical retraction system 10 is securely registered to the operating table. The upper portion may also be provided with at least one aperture 55 dimensioned to receive a tool (not shown) configured to allow the operator to alter the position of the retractor body 12 in order to adjust the angle of the operative corridor.

The lower portion 40 includes a first lumen 54 extending axially through the housing member 20 transverse to the first recess 42. By way of example only, the first lumen has a generally rectangular cross-section and is configured to slideably receive the first rack member 58 therethrough. The lower portion 40 further includes a second lumen 56 extending axially through the housing member 20 transverse to the first recess 42 and parallel to the first lumen 54. By way of example only, the second lumen 56 has a generally rectangular cross section and is configured to slideably receive the second rack member 60 therethrough.

Figure 11:
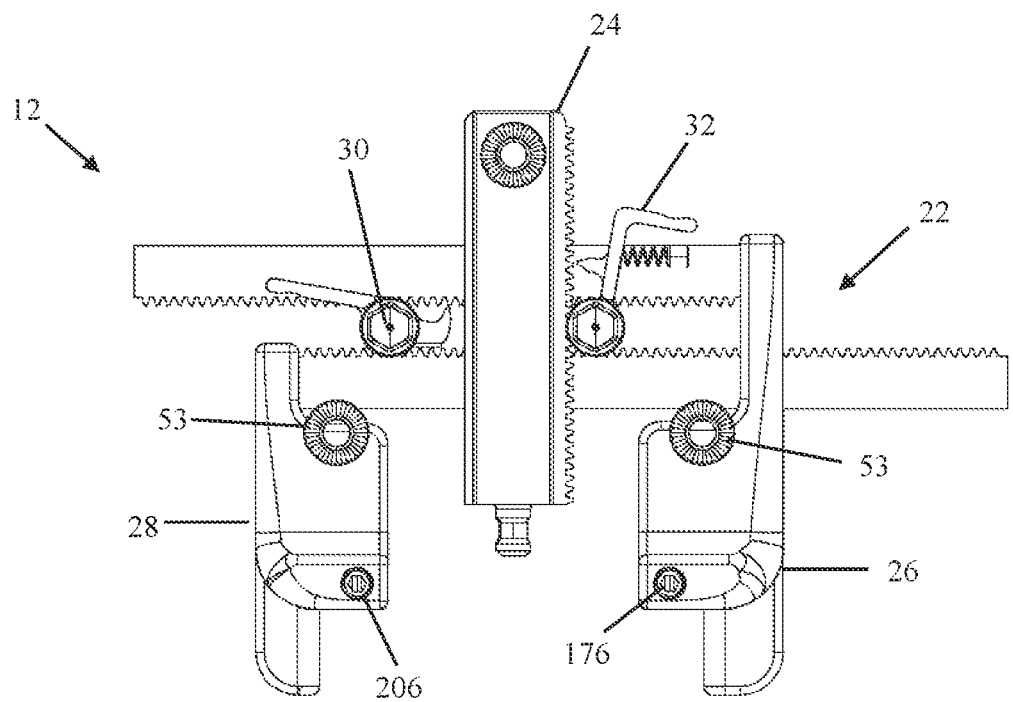
FIG. 11 is a top perspective view of the retractor body of FIG. 8 with the housing member removed.
Figure 12:
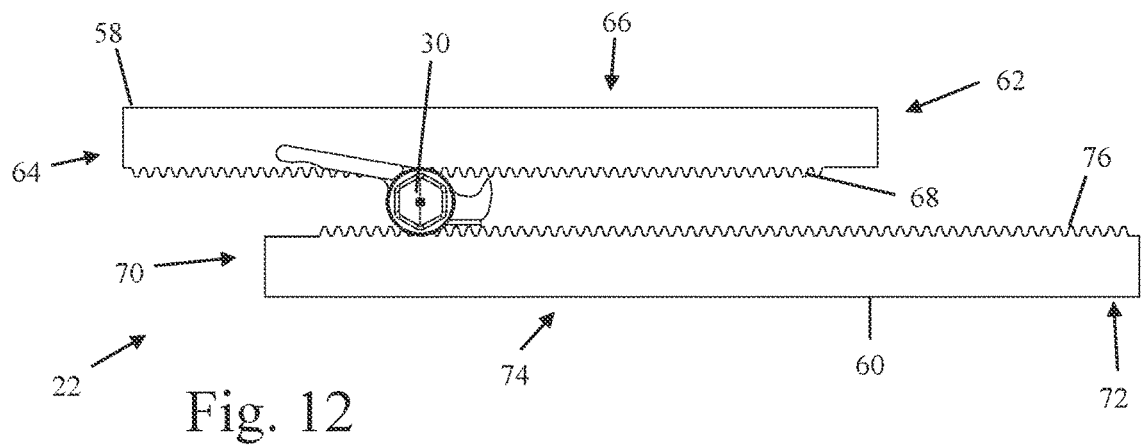
FIG. 12 is a top plan view of an example of a rack member forming part of the retractor body of FIG. 7.

FIG. 11 illustrates the retractor body 12 without the housing member 20 to provide a clear view of the rack 22. Referring now to FIG. 12, the rack 22 includes a first rack member 58 and a second rack member 60. By way of example only, the first rack member 58 is an elongated axial member having a generally rectangular cross section and a first end 62, a second end 64, and an elongated body 66 extending therebetween. Although shown and described as generally rectangular, other cross sectional shapes are possible without departing from the scope of the present invention. The first rack member 58 is dimensioned to be slideably received within the first lumen 54 of the housing member 20. The first end 62 is connected to the first retractor arm 26. The first rack member 58 further includes a plurality of teeth 68 on one surface, the teeth being provided along substantially the length of the first rack member 58. The teeth interact with the first toggle 30 to allow controlled caudal-cranial movement of the first retractor blade 14, as will be described.

By way of example only, the second rack member 60 is an elongated axial member having a generally rectangular cross section and a first end 70, a second end 72, and an elongated body 74 extending therebetween. Although shown and described as generally rectangular, other cross sectional shapes are possible without departing from the scope of the present invention. The second rack member 60 is dimensioned to be slideably received within the second lumen 56 of the housing member 20. The first end 70 is connected to the second retractor arm 28. The second rack member 60 further includes a plurality of teeth 76 on one surface, the teeth being provided along substantially the length of the second rack member 60. The teeth interact with the first toggle 30 to allow controlled caudal-cranial movement of the second retractor blade 16, as will be described.

Figure 13:
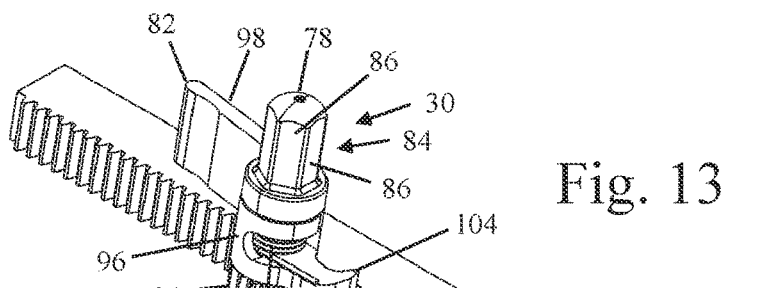
FIG. 13 is a perspective view of the rack member of FIG. 12 with the second rack member removed.
Figure 14:
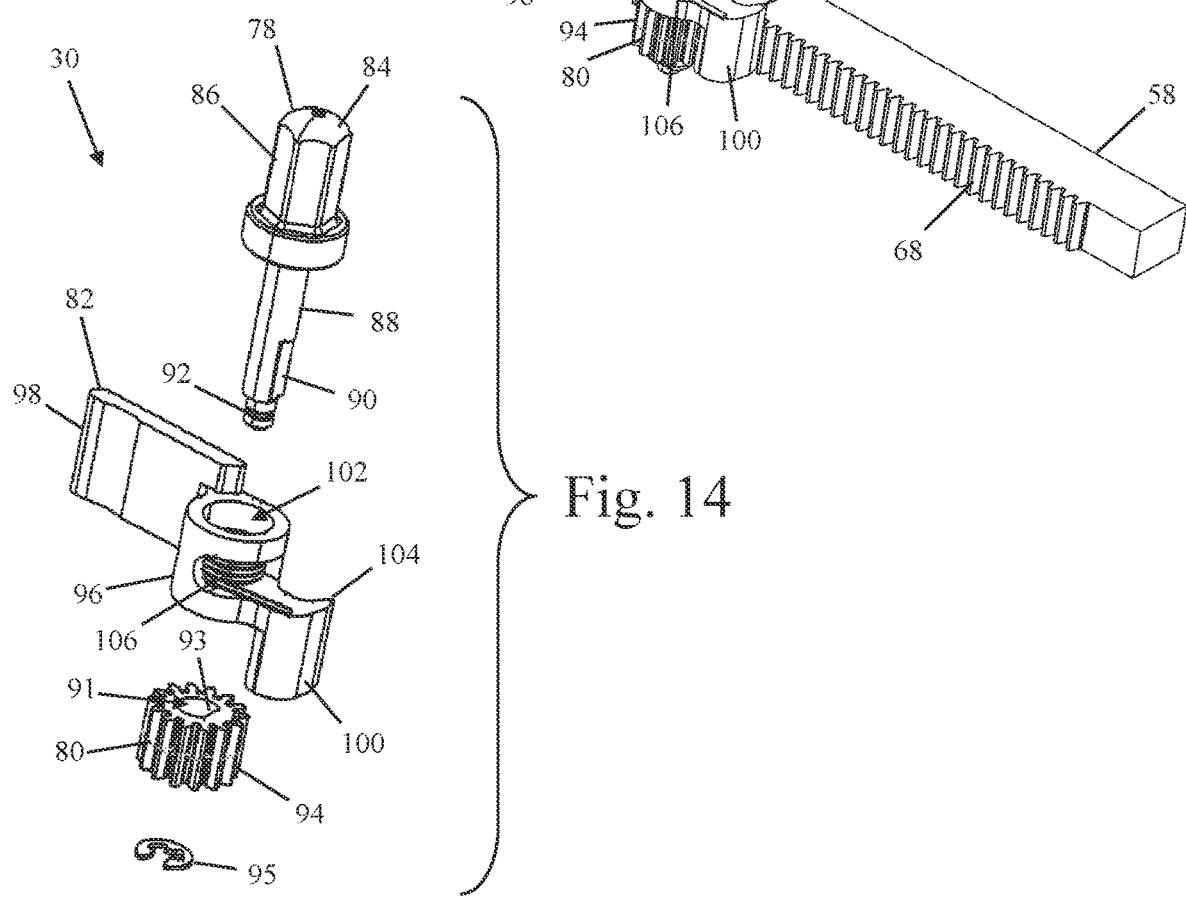
FIG. 14 is an exploded perspective view of a first toggle forming part of the retractor body of FIG. 7.

Referring to FIGS. 7 and 13-14, the first toggle 30 includes an actuator 78, a gear 80, and a release member 82. The actuator 78 includes a superior handle portion 84 that includes a friction feature that enables a user to grip and turn the handle portion 84. By way of example only, the handle portion 84 is provided with a friction feature comprising a plurality of planar surfaces 86 (for engagement with a rotation handle), however other friction features are possible, for example ridges, knobs, dimples, and/or a material overlay such as rubber that provides for adequate gripping by a user. The actuator 78 further includes an inferior post 88 that extends away from the handle portion 84. The inferior post 88 includes at least one generally planar surface 90 configured to mate with the planar surface 93 of the gear 80 and transfer the torque applied by a user to the handle portion 84 to the gear 80, thus turning the gear 80. The inferior post 88 further includes a recess 92 for receiving a snap ring 95, which functions to secure the first toggle 30 to the housing member 20.

By way of example only, the gear 80 has a generally circular cross-section and includes a central lumen 91 extending therethrough and a plurality of teeth 94 in the form of vertical ridges distributed about the perimeter of the gear 80. The central lumen 91 includes a planar surface 93 configured to mate with the planar surface 90 of the actuator 78 to transfer the torque applied by a user to the handle portion 84 to the gear 80, thus turning the gear 80. The teeth 94 of the gear 80 are configured to mate with the teeth 68, 76 of the first and second rack members 58, 60. As shown by way of example in FIG. 12, the first toggle 30 is positioned between the first and second rack members 58, 60 such that the teeth 94 of the gear 80 simultaneously engages the teeth 68 of the first rack member 58 and the teeth 76 of the second rack member 60. Thus, as the handle portion 84 of the actuator 78 is turned by a user, the gear 80 causes the first and second racks 58, 60 to simultaneously move in opposite directions. For example, when the handle portion 84 is rotated in a clockwise direction, the first rack 58 will move in a cranial direction (assuming proper placement of the retractor relative to the spine) and the second rack 60 will move in a caudal direction. The effect of this movement is that the first retractor blade 14, through its connection to the first arm 26 (which is connected to the first rack member 58) will move in a cranial direction and the second retractor blade 16, through its connection to the second retractor arm 28 (which is connected to the second rack member 60) will move simultaneously in a caudal direction.

Referring again to FIGS. 7 and 13-14, the release member 82 includes body 96, a tab 98, and a flange 100. The body 96 is a generally circular member having a central lumen 102 extending therethrough. The central lumen 102 is dimensioned to receive the post 88 of the actuator 78. The tab 98 extends radially from the body and functions as a manipulation point for the user. The flange 100 includes a ratchet member 104 that is dimensioned to interact with the teeth 68 of the first rack member 58. The release member 82 further includes a spring 106 that biases the ratchet member 104 into an engaged position relative to the teeth 68. Thus, as the gear 80 turns and the first rack member 58 moves, the ratchet member 104 clicks into engagement with each passing tooth 68. Thus the ratchet member 104 provides for controlled translation of the first and second rack members 58, 60, and creating a customizable operative corridor established in incremental amounts. The ratchet member 104 further prevents unwanted migration of the first rack member 58 (and therefore the second rack member 60 as well) such that the desired operative corridor will not alter once established. The ratchet member 104 is configured to allow for unidirectional movement of the first rack member 58 relative thereto while the ratchet member 104 is engaged to the gear 80. The ratchet member 104 effectively prevents counterclockwise turning of the handle member 84. To contract the operative corridor, for example upon completion of the desired surgical procedure, the user activates the tab 98, causing the ratchet member 58 to disengage from the teeth 68. This allows for free (though still simultaneous) translation of the first and second rack members relative to the housing member 20. That is, a counterclockwise turning of the handle member 84 will cause the first and second rack members 58, 60 to translate in an opposite direction, such that the first retractor blade 14 will move in a caudal direction and the second retractor blade 16 will move in a cranial direction.

Figure 15:
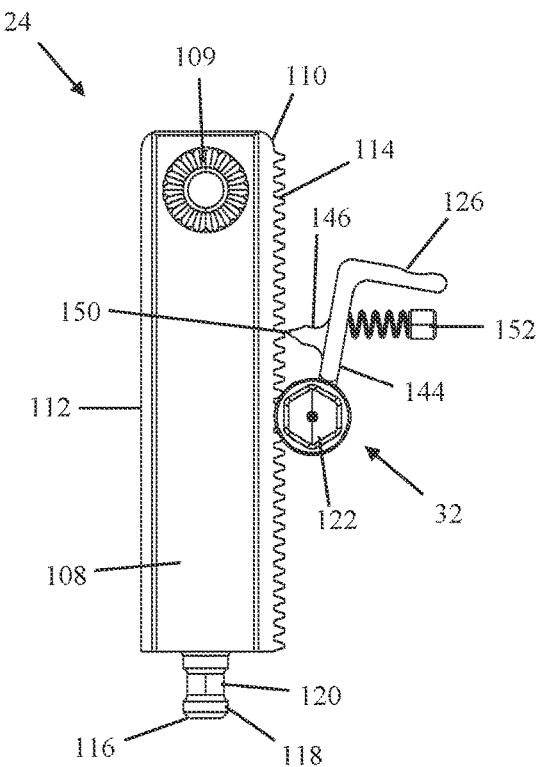
FIGS. 15-16 are top plan and perspective views, respectively, of a medial retraction member coupled with a second toggle, forming part of the retractor body of FIG. 7.
Figure 17:
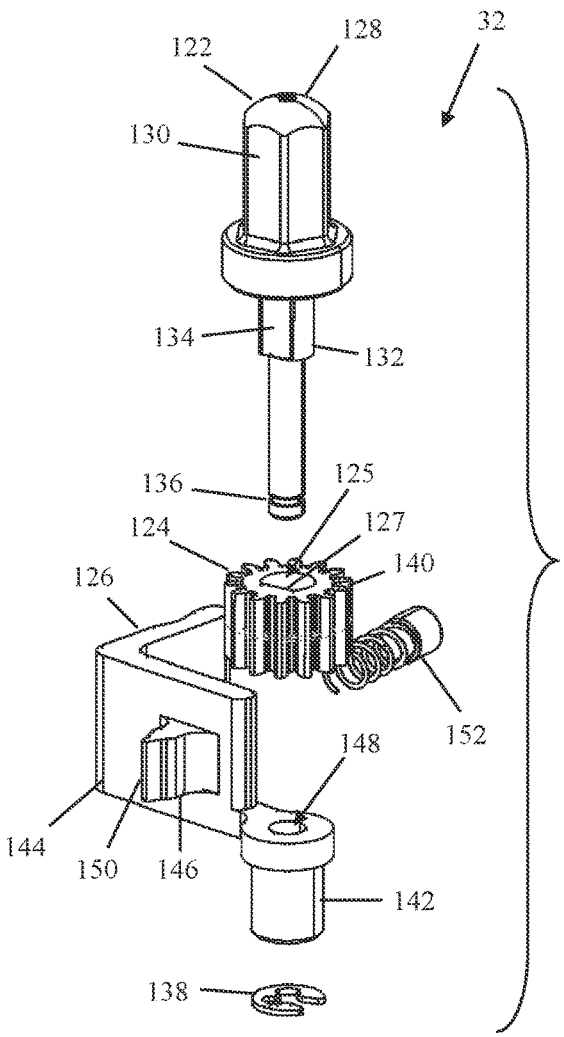
FIG. 17 is an exploded perspective view of a second toggle forming part of the retractor body of FIG. 7.
Figure 16:
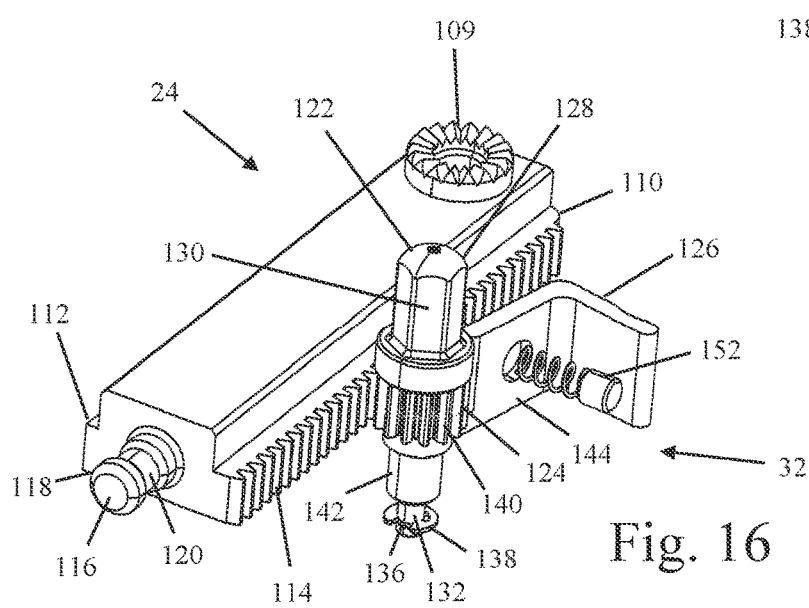

FIGS. 15-17 illustrate the medial retraction member 24 in greater detail. By way of example only, the medial retraction member 24 comprises a medial rack 108 dimensioned to fit in the first recess 42 of the housing member 20. By way of example only, the medial rack 108 is an elongated axial member having a generally rectangular cross section. The medial rack 108 includes a first flange 110 and a second flange 112, each extending the length of the medial rack 108 and dimensioned to engage the overhangs 44 of the first recess 42. The first flange 110 includes a plurality of teeth 114 in the form of vertical ridges that are distributed along the length of the first flange 110. The teeth 114 engage with the gear 124 of the second toggle 32 to enable movement of the medial rack 108. The medial rack 108 further includes a post 116 extending axially from the front end of the medial rack 108. The post 116 is configured for engagement with the medial blade 18. The post 116 has an end portion 118 having a first diameter and a recessed portion 120 between the end portion 118 and the medial rack 108, the recessed portion 120 having a reduced diameter relative to the end portion 118. This configuration allows for engagement, for example a snap-fit engagement, with the medial blade 18.

The medial rack further includes at least one attachment member 109 dimensioned to enable attachment of the medial retraction member 24 to an articulating arm (not shown) within the operative field. This attachment to the articulating arm ensures that the surgical retraction system 10 is securely registered to the operating table. The attachment member 109 on the medial retraction member 24 is structurally identical to, and performs the same function as, the attachment member 53 of the housing member 20 (FIGS. 10-11). However, attachment to the attachment member 109 of the medial retraction member 24 provides an entirely different effect than attachment to the attachment member 53 of the housing member 20. Specifically, attachment to the attachment member 109 registers the medial retraction member 24 to the articulating arm, and therefore the surgical table. In this state, the medial retraction member 109 is secured in place, and actuation of the toggle 32 will therefore cause the retractor body 12, to move laterally relative to the patient. Conversely, when the articulating arm is attached to the attachment member 53 of the housing 20, the housing 20 is secured in place relative to the operating table, the actuation of the toggle 32 will cause the medial retraction member 24 to move medially relative to the patient. This feature is advantageous in situations in which the medial blade 18 has been placed, but for some reason the surgeon would prefer to move the operative corridor laterally relative to the spine rather than medially.

Referring now to FIG. 7 in addition to FIGS. 15-17, the second toggle 32 includes an actuator 122, a gear 124, and a release member 126. The actuator 122 includes a superior handle portion 128 that includes a friction feature that enables a user to grip and turn the handle portion 128. By way of example only, the handle portion 128 is provided with a friction feature comprising a plurality of planar surfaces 130, however other friction features are possible, for example ridges, knobs, dimples, and/or a material overlay such as rubber that provides for adequate gripping by a user. The actuator 122 further includes an inferior post 132 that extends away from the handle portion 128. The inferior post 132 includes at least one generally planar surface 134 configured to mate with the planar surface 127 of the gear 124 and transfer the torque applied by a user to the handle portion 128 to the gear 124, thus turning the gear 124. The inferior post 132 further includes a recess 136 for receiving a snap ring 138, which functions to secure the second toggle 32 to the housing member 20.

By way of example only, the gear 124 has a generally circular cross-section and includes a central lumen 125 extending therethrough and a plurality of teeth 140 in the form of vertical ridges distributed about the perimeter of the gear 124. The central lumen 125 includes a planar surface 127 configured to mate with the planar surface 134 of the actuator 122 to transfer the torque applied by a user to the handle portion 128 to the gear 124, thus turning the gear 124. The teeth 140 of the gear 124 are configured to mate with the teeth 114 of the medial rack member 108. As shown by way of example in FIG. 15, the second toggle 32 is positioned adjacent the medial rack member 108. As the handle portion 128 of the actuator 122 is turned by a user, the gear 124 causes the medial rack 108 to translate in a medial (or lateral) direction. For example, when the handle portion 128 is rotated in a clockwise direction, the medial rack 128 will move in a medial direction (i.e. toward the spinal column, assuming proper placement of the retractor relative to the spine). The effect of this movement is that the medial retractor blade 18, through its connection to the medial rack 108 will move in a medial direction, thereby retracting soft tissue and expanding the operative corridor. The medial rack 108 thus contributes to the customizable nature of the operative corridor.

The release member 126 includes body 142, a tab 144, and a flange 146. The body 142 is a generally circular member having a central lumen 148 extending therethrough. The central lumen 148 is dimensioned to receive the post 132 of the actuator 122. The tab 144 extends radially from the body and functions as a manipulation point for the user. The flange 146 includes a ratchet member 150 that is dimensioned to interact with the teeth 114 of the medial rack member 108. The release member 126 further includes a spring 152 positioned between the tab 144 and the housing 20 that biases the ratchet member 150 into an engaged position relative to the teeth 114. Thus, as the gear 124 turns and the medial member 108 moves, the ratchet member 150 clicks into engagement with each passing tooth 114. Thus the ratchet member 150 provides for controlled translation of the medial rack member 108, and creating a customizable operative corridor established in incremental amounts. The ratchet member 150 further prevents unwanted migration of the medial rack member 108 such that the desired operative corridor will not alter once established. The ratchet member 150 is configured to allow for unidirectional movement of the medial rack member 108 relative thereto while the ratchet member 150 is engaged to the gear 124. The ratchet member 150 effectively prevents counterclockwise turning of the handle member 128. To contract the operative corridor, for example upon completion of the desired surgical procedure, the user activates the tab 144, causing the ratchet member 108 to disengage from the teeth 114. This allows for free translation of the medial rack member 108 relative to the housing member 20. That is, a counterclockwise turning of the handle member 128 with the ratchet member 150 disengaged will cause the medial rack member 108 to translate in an opposite direction (e.g. lateral direction, away from the spine.

Figure 18:
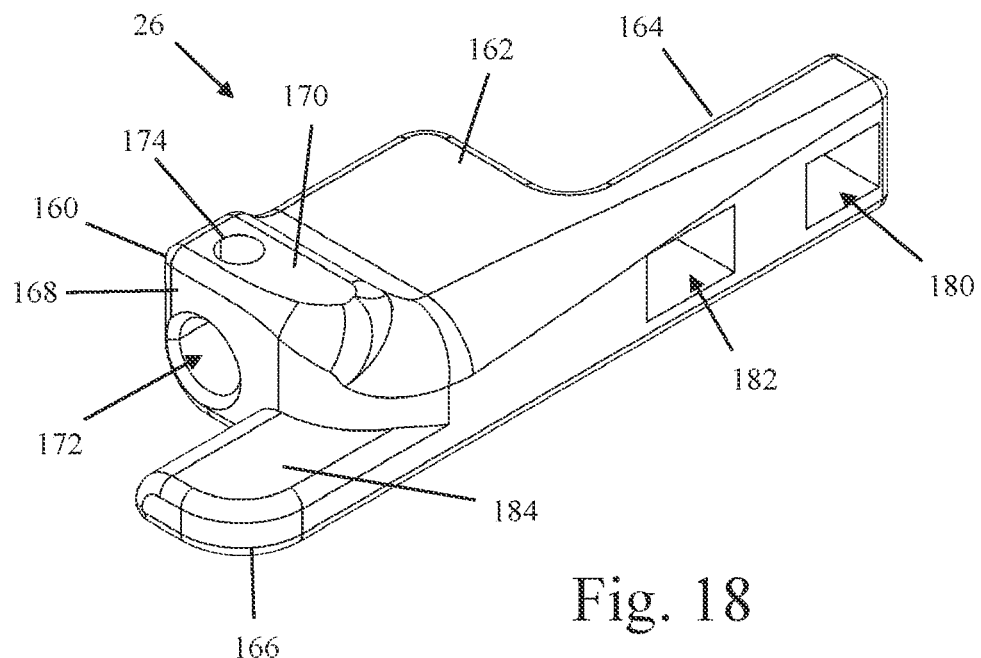
FIGS. 18-19 are perspective views of an example of first arm member forming part of the retractor body of FIG. 7.
Figure 19:
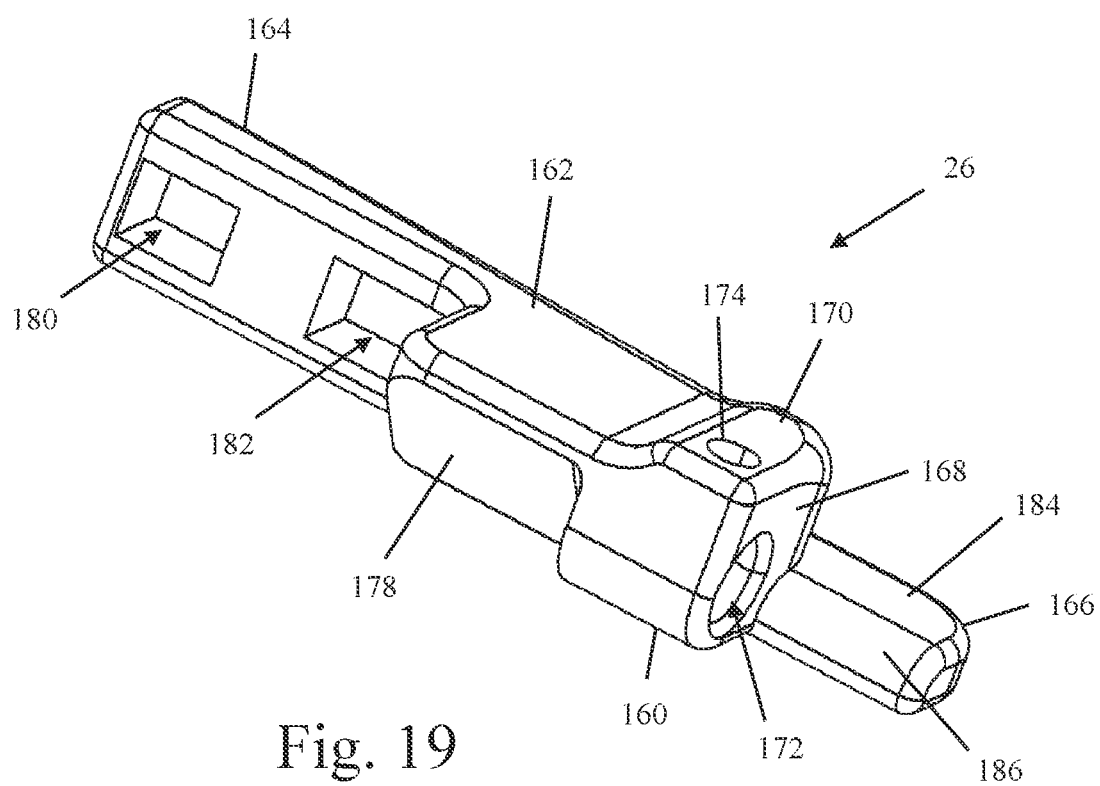

FIGS. 18-19 illustrate the first arm member 26 in greater detail. The first arm member 26 includes a front body portion 160, a rear body portion 162, a first flange 164, and a second flange 166. The front body portion includes a front surface 168 and a top surface 170. The front surface 168 includes an aperture 172 formed therein and extending into the front body portion 160. The aperture 172 is dimensioned to receive the engagement post 230 of the first retractor blade 14 (FIG. 6) to enable engagement of the first retractor blade 14 to the retractor body 12. The top surface 170 includes a second aperture 174 configured to receive a set screw 176 (FIG. 7). The set screw 176 functions to lock the engagement post 230 within the aperture 172, preventing unwanted ejection of the first retractor blade 14 from the first arm member 26. The rear body portion includes a lower-facing inside tapered surface 178 that allows the medial blade 18 to pivot within a plane that is transverse to the longitudinal axis of the medial rack member 108. This pivoting enables intraoperative repositioning of the retractor body 12 relative to the surgical target site without the need to detach the retractor body 12 from the articulating arm. The net effect is to alter the approach angle of the operative corridor relative to the surgical target site.

The first flange 164 extends axially from the rear body portion 162 and includes a third aperture 180 and fourth aperture 182. The third aperture 180 is configured to securely mate with the first end 62 of the first rack member 58 such that the first arm member 26 moves with the first rack member 58. By way of example only, the first arm member 26 can be securely mated with the first rack member 58 by welding, adhesive, snap-fit, friction-fit, or any other suitable method. Alternatively, the first arm member 26 can be integrally formed with the first rack member 58 without departing from the scope of the present invention. The fourth aperture 182 is configured to allow passage of the second rack member 60 therethrough. The third and fourth apertures 180, 182 are generally rectangular in shape, however other shapes are possible depending on the cross-sectional shapes of the first and second rack members 58, 60. The second flange 166 extends axially from the front body portion 160 and includes a generally planar upper surface 184 and a curved medial surface 186. The second flange 166 interacts with the thumbscrew 240 of the first retractor blade 14 and functions as a shelf to enable the lockable adjusted angulation feature of the first retractor blade 14, as well as an alternative distraction feature of the tissue retraction system 10, each of which will be described in greater detail below.

Figure 20:
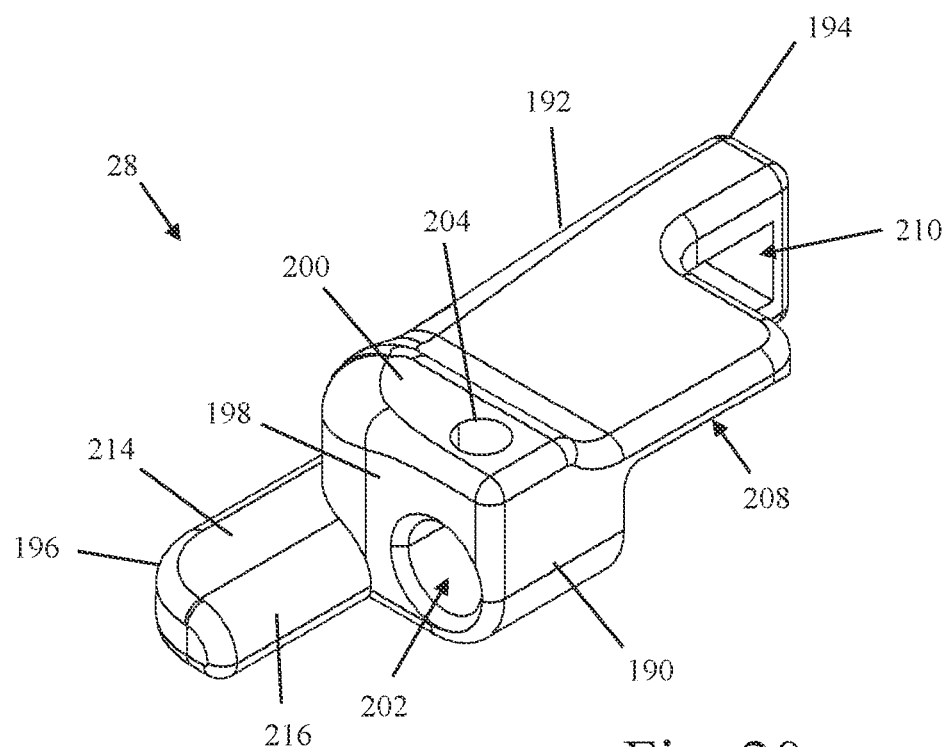
FIGS. 20-21 are perspective views of an example of a second arm member forming part of the retractor body of FIG. 7.
Figure 21:
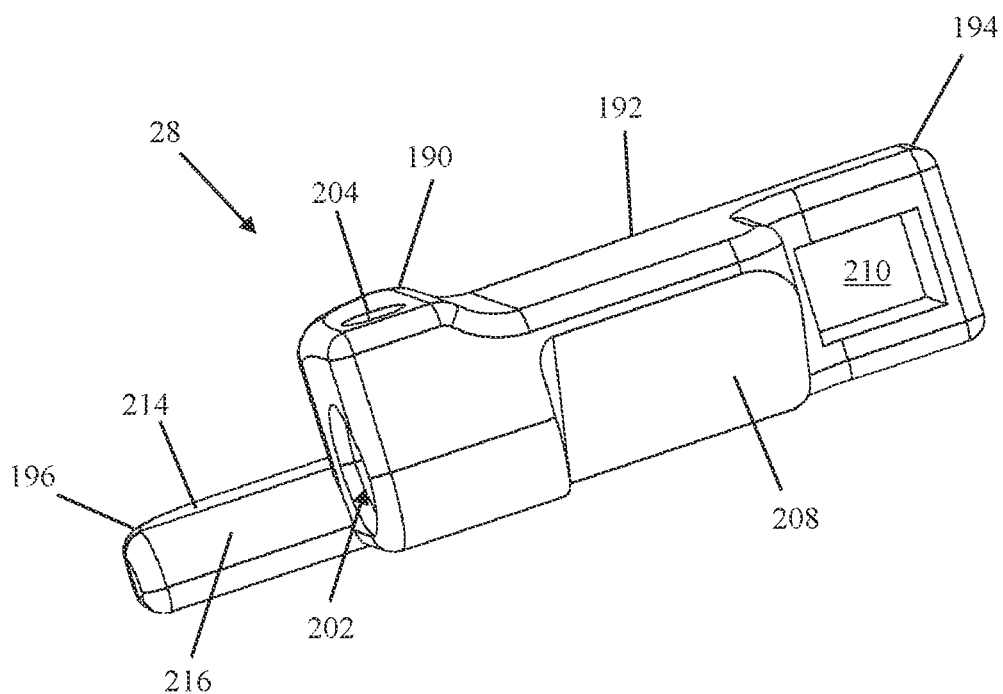

FIGS. 20-21 illustrate the second arm member 28 in greater detail. The second arm member 28 includes a front body portion 190, a rear body portion 192, a first flange 194, and a second flange 196. The front body portion includes a front surface 198 and a top surface 200. The front surface 198 includes an aperture 202 formed therein and extending into the front body portion 190. The aperture 202 is dimensioned to receive the engagement post 230 of the second retractor blade 16 (FIG. 6) to enable engagement of the second retractor blade 16 to the retractor body 12. The top surface 200 includes a second aperture 204 configured to receive a set screw 206 (FIG. 7). The set screw 206 functions to lock the engagement post 230 within the aperture 202, preventing unwanted ejection of the second retractor blade 16 from the first arm member 28. The rear body portion includes a lower-facing inside tapered surface 208 that that allows the medial blade 18 to pivot within a plane that is transverse to the longitudinal axis of the medial rack member 108. This pivoting enables intraoperative repositioning of the retractor body 12 relative to the surgical target site without the need to detach the retractor body 12 from the articulating arm. The net effect is to alter the approach angle of the operative corridor relative to the surgical target site.

The first flange 194 extends axially from the rear body portion 192 and includes a third aperture 210. The third aperture 210 is configured to securely mate with the first end 70 of the second rack member 60 such that the second arm member 28 moves with the second rack member 60. By way of example only, the second arm member 28 can be securely mated with the second rack member 60 by welding, adhesive, snap-fit, friction-fit, or any other suitable method. Alternatively, the second arm member 28 can be integrally formed with the second rack member 60 without departing from the scope of the present invention. The third aperture 210 is generally rectangular in shape, however other shapes are possible depending on the cross-sectional shapes of the second rack member 60. The second flange 196 extends axially from the front body portion 190 and includes a generally planar upper surface 214 and a curved medial surface 216. The second flange 196 interacts with the thumbscrew 240 of the second retractor blade 16 and functions as a shelf to enable the lockable adjusted angulation feature of the second retractor blade 16, as well as an alternative distraction feature of the tissue retraction system 10, each of which will be described in greater detail below.

The retractor blades 14, 16 may be provided in any size or shape suitable to establish and maintain an operative corridor to the surgical target site. In one embodiment, the retractor blades 14, 16 can be individually selected for appropriate length. Therefore, the retractor blades 14, 16 can be of different lengths which gives the surgeon additional control over the shape and size of the operative corridor (as shown for example in FIGS. 62 and 63). The retractor blades 14, 16 may be provided having a generally arcuate cross-section to facilitate a circular or generally oblong surgical corridor. FIGS. 22-25 illustrate an example of a first retractor blade 14 according to the present invention. FIG. 26 is an exploded view of the first retractor blade 14. For the purposes of illustration, the specific features of the invention will be described in relation to the first retractor blade 14. However it should be understood that the features described in relation to first retractor blade 14 are the same for second retractor blade 16, but provided in a mirror-image configuration. Thus, though the first and second retractor blades 14 and 16 are not strictly interchangeable, the features of each blade are virtually identical rendering a repeat discussion unnecessary as cumulative.

Figure 22:
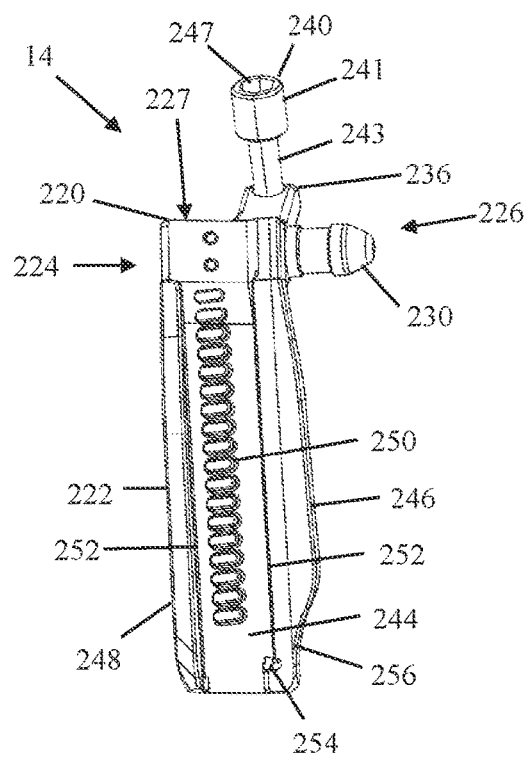
FIGS. 22-25 are various plan views of an example of a retractor blade assembly forming part of the tissue retraction system of FIG. 6.
Figure 23:
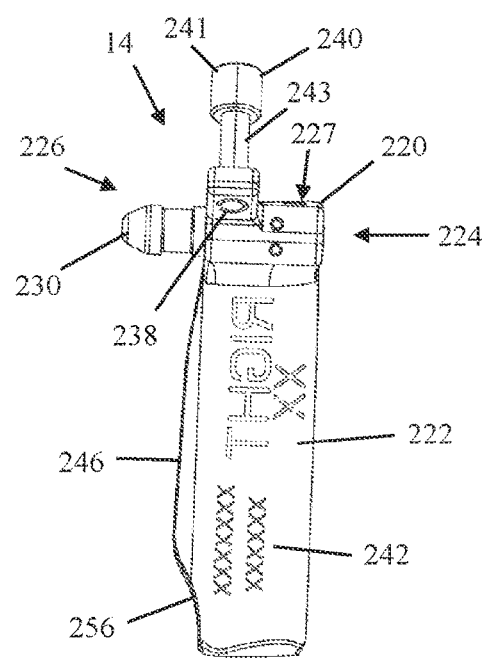
Figure 24:
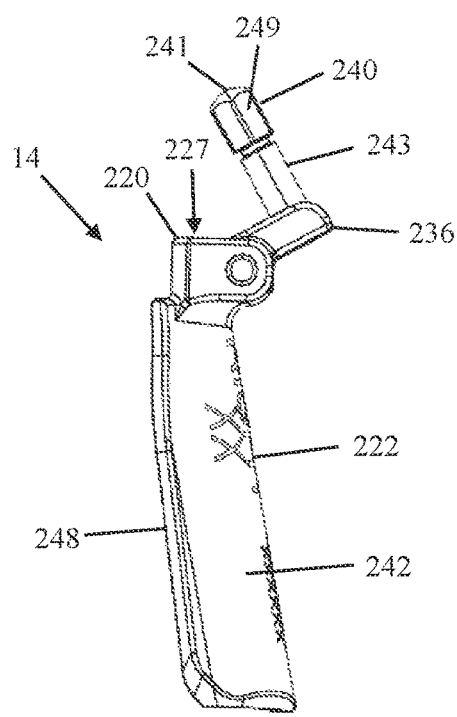
Figure 25:
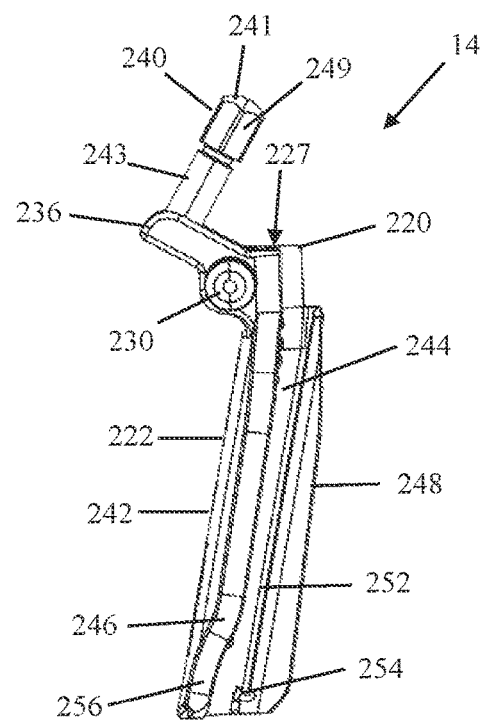
Figure 26:
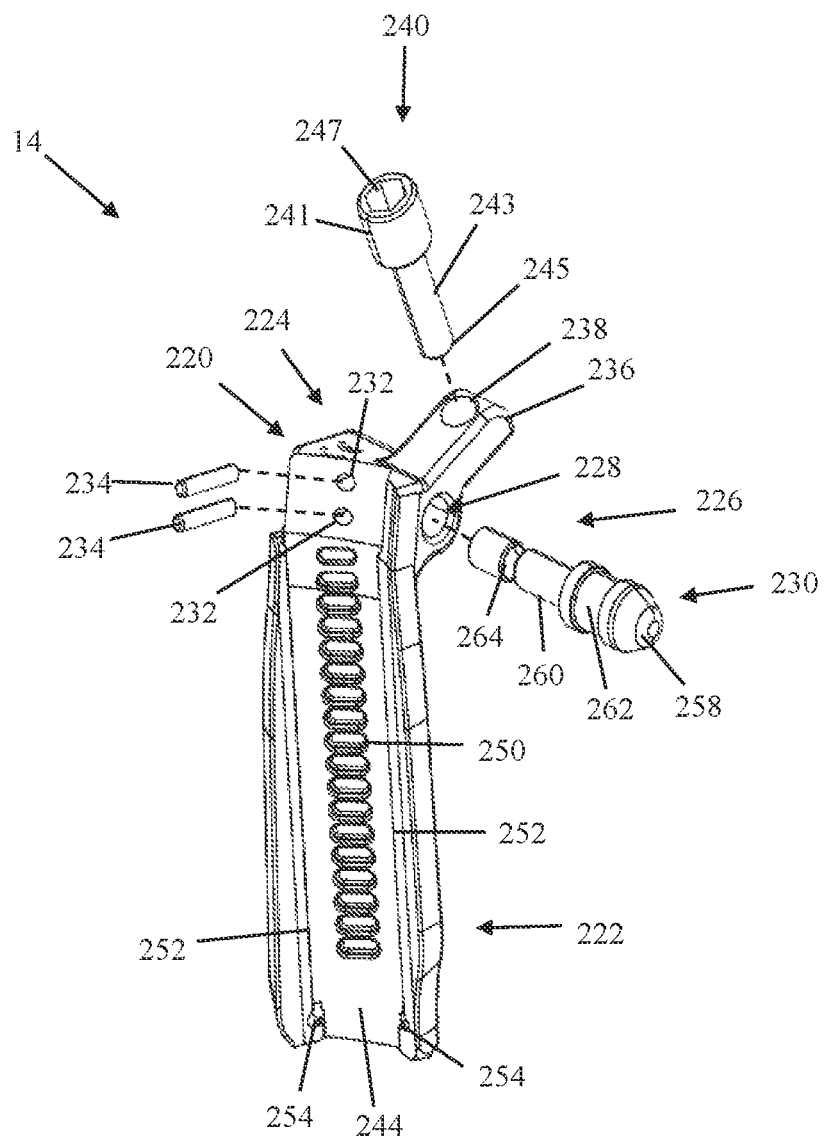
FIG. 26 is an exploded view of the retractor blade assembly of FIG. 22.
Figure 27:
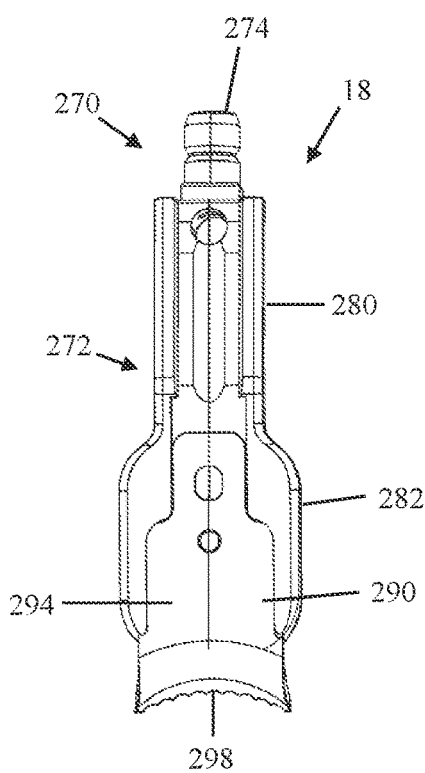
FIGS. 27-30 are front plan, perspective, rear perspective, and side plan views, respectively, of a medial retractor blade assembly forming part of the tissue retraction system of FIG. 6.
Figure 28:
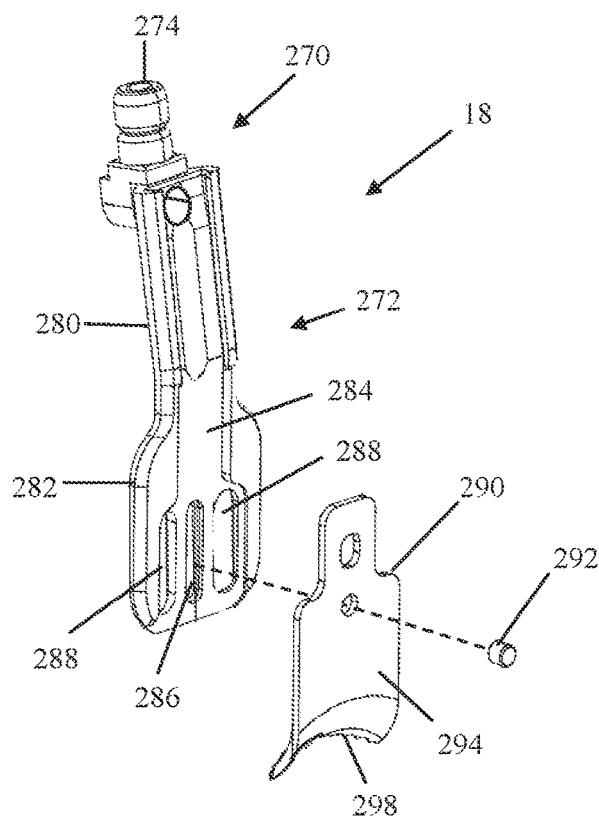
Figure 29:
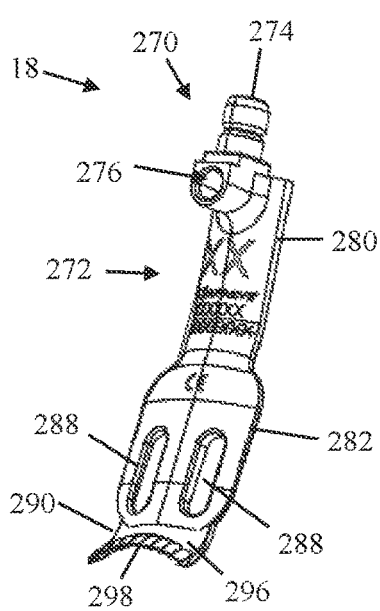
Figure 30:
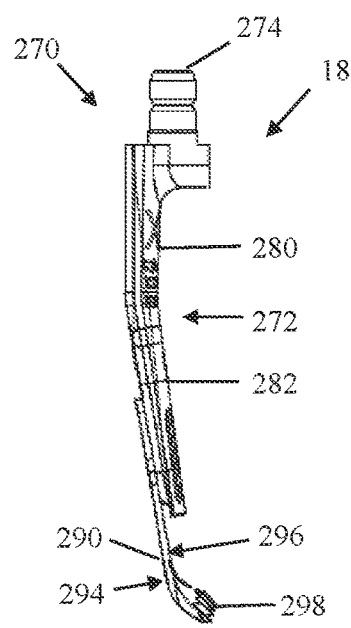
Figure 31:
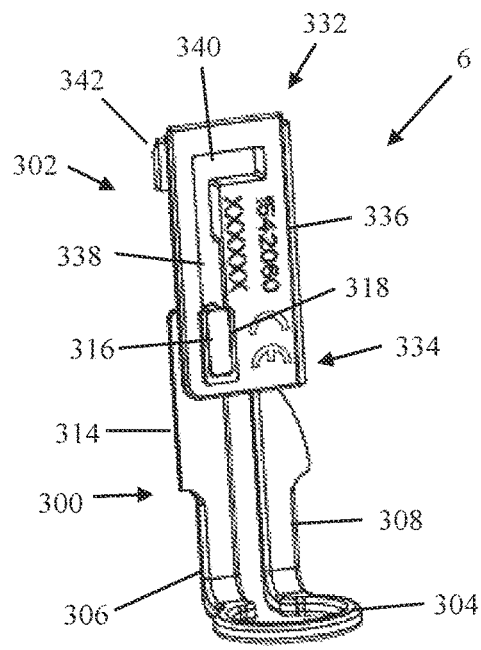
FIGS. 31-34 are perspective, exploded perspective, rear plan, and top plan views, respectively, of an example of a hoop shim assembly forming part of the surgical fixation system of FIG. 1, the hoop shim assembly shown in an unlocked position.
Figure 32:
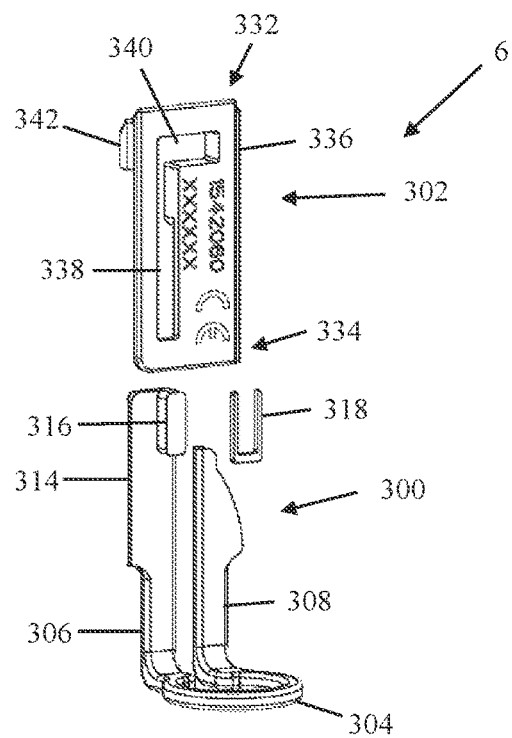

Referring now to FIGS. 22-26, the first retractor blade 14 includes an attachment portion 220 and a blade portion 222 extending distally from the attachment portion 220. The attachment portion 220 has a front side 224, a back side 226, and a top surface 227. The back side 226 includes a first aperture 228 extending into the upper attachment portion 220 and configured to receive an engagement post 230 therein. The engagement post 230 is configured to mate with the aperture 172 of the first arm member 26 to couple the first retractor blade 14 with the retractor body 12. Correspondingly, the engagement post 230 is configured to mate with the aperture 202 of the second arm member 28 to couple the second retractor blade 16 with the retractor body 12. The attachment portion 220 further includes a pair of second apertures 232 extending through the attachment portion 220 parallel to one another and transverse to the first aperture 228. The second apertures 232 are vertically offset from the first aperture 228 but are at least partially in communication with the first aperture 228. The second apertures 232 are configured to receive pins 234 that operate to secure the engagement post 230 to the retractor blade 14 (explained in further detail below). The attachment portion further includes a flange 236 extending angularly (relative to the top surface 227) therefrom, the flange 236 including an aperture 238 configured to receive a thumb screw 240 therein. The flange 236 and thumb screw 240 interact with the second flange 166 of the first arm member 26 to enable the lockable angulation feature of the first retractor blade 14, as well as an alternate tissue distraction feature of the tissue retraction system 10, as will be described in greater detail below. By way of example only, both the thumb screw 240 and aperture 238 include threads to enable a threaded engagement therebetween. However, other engagements are possible without departing from the scope of the present invention. By way of example only, the flange 236 is angularly offset from the top surface 227 within a range of 15 to 50 degrees, with the preferable angle being approximately 30 degrees. The thumbscrew 240 includes a head 241, a shaft 243, and a distal tip 245. The head 241 is generally cylindrical in shape and includes a rotation feature that enables the user to rotate the thumb screw 240. The rotation feature may be anything that is suitable to enable rotation of the thumb screw 240, for example including but not limited to a socket 247 for receiving a driver as shown in FIGS. 22, 23 and 26, and/or an external planar surfaces 249 to provide gripping for a driver or a user's hand, as shown in FIGS. 24 and 25.

The blade portion 222 extends distally from the attachment portion 220 and includes an outside surface 242, an inside surface 244, a first lip 246, and a second lip 248. The outside surface is a smooth arcuate surface configured to interact with the patient's soft tissue near the operative corridor. As best seen in FIG. 24, the outside surface 242 extends from the attachment portion 220 at a non-orthogonal angle relative to the top surface 227. Since much of the blade has a generally uniform thickness, the inside surface 244 extends from the attachment portion 220 at the same non-orthogonal angle relative to the top surface 227. Thus, the effect is that the operative corridor is immediately established having a conical shape with no further adjustment of the tissue retraction assembly 10 required. Additionally, the blade portion 222 extends from the attachment portion 220 such that the blade face (i.e. inner surface 244) is oriented orthogonal to the attachment portion 220. Thus, when the retractor blade is attached to the retractor body 10, the inside surface faces 244 the operative corridor at an angle rather than facing directly at the opposing blade, for example between 20 and 60 degrees). This orientation of the blade portion relative to the attachment portion helps optimize the shape (e.g. triangular) of the operative corridor. The inside surface 244 includes a plurality of notches or recesses 250 arranged in a linear alignment thereon, the notches or recesses 250 being configured to interact with the knob 498 of the inserter 400, as will be described in further detail below. The blade portion 222 further includes a pair of track grooves 252 spaced apart from one another and extending the length of the inside surface 244. The track grooves 252 are configured to slideably receive a shim attachment, for example the hoop shim 6 shown and described herein. It should be understood, however, that any suitable shim attachment may be used without departing from the scope of the present invention. At the distal end of each of the track grooves 252 there is a stop 254, which interacts with the hoop shim 6 to prevent the hoop shim 6 from passing the stop 254 once it has been fully engaged to the retractor blade. The first lip 246 and second lip 248 comprise edges of the blade portion 222 and each extend along the length of the blade portion 222 from the attachment portion 222 to the distal end of the blade portion 222. Notably, the first and second lips 246, 248 are asymmetric relative to one another.

For example, the first lip 246 has a concave portion 256 that allows for clearance of spinal anatomy during blade angulation.

Referring to FIG. 26, the engagement post 230 includes a boss 258 and a post 260. The boss 258 is generally cylindrical in shape and is dimensioned to be received within the aperture 172 of the first arm member 26 to couple the first retractor blade 14 with the retractor body 12. The boss 258 includes a recess 262 formed therein, the recess 262 configured to receive at least a portion of the set screw 176 to securely engage the first retractor blade 14 to the retractor body 12. The post 260 extends axially from the boss 258 and is configured to be received within aperture 228 of the first retractor blade 14. The post 260 further includes a recess 264 formed therein, the recess 264 being sized and dimensioned to receive at least a portion of both pins 234 therein. The pins 234 extend transversely relative to the post 260, and prevent undesirable uncoupling of the post 230 from the first retractor blade 14. In practice, the retractor blade 14 (and retractor blade 16) is provided with the post 230 already secured within the aperture 228 with the pins 234 in place. The pins 234 may be secured by any suitable method, including for example welding, that ensures that the pins 234 securely retain the post 230 within the aperture 238. Although described herein as using a set screw 176 to secure the first retractor blade 14 (and/or second retractor blade 16) to the retractor body 12, any suitable attachment mechanism can be used without departing from the scope of the present invention. For example, a quick connection mechanism such as a snap fit engagement is possible, as is a friction engagement or an integral blade.

Referring to FIGS. 27-30, the medial retractor blade 18 may be provided in any size or shape suitable to establish and maintain an operative corridor to the surgical target site. By way of example only, the medial retractor blade 18 includes an attachment portion 270 and a blade portion 272. The attachment portion 270 includes a knob 274 and an aperture 276. The knob 274 is configured to allow manipulation by a user, for example to change the angulation of the medial retractor blade 18. The knob also connects to a manual insertion tool (not shown). By way of example, the manual insertion tool includes a cylinder with a canted coil received in a notch therein. In a natural position, the coil extends into the cylinder. The tapered end of the knob 274 deflects the canted coil as the knob passes. When the coil reaches the groove formed in the knob, the coil returns to the natural position and secures the blade to the manual inserter. The aperture 276 extends into the attachment portion 270 and is configured to receive the post 116 of the medial retraction member 24 therein to securely attach the medial retractor blade 18 to the retractor body 12. The engagement between the medial retractor blade 18 and the post 116 is provided by way of example as a snap-fit engagement allowing for relative easy insertion and/or removal of the medial retractor blade 18. However, other engagements are possible without departing from the scope of the present invention, including but not limited to using a set screw (e.g. through the knob 274 into the aperture 276), friction engagement, or providing a medial retraction member with integral blade. This engagement allows a user to intraoperatively change the medial retractor blade 18, for example to swap out a shorter blade for a longer blade, and vice versa.

The blade portion 272 includes an upper portion 280 and a lower portion 282. The upper portion 280 is adjacent to the attachment portion 270 and extends generally orthogonally therefrom. The lower portion 282 is located distally of the upper portion 280 and is offset from the upper portion 280 such that it forms an obtuse angle with the upper portion 280 (best shown in FIG. 30). By way of example only, the offset is such that the distal end of the lower portion 282 is offset from the plane of the upper portion 280 by approximately one-quarter of an inch. Depending upon the length of the blade portion 272, the angle formed between the upper and lower portions 280, 282 is variable to achieve this one-quarter inch offset. The lower portion 282 is wider than the upper portion to accommodate the retraction of a greater amount of the patient's soft tissue near the surgical target site. The lower portion 282 includes a recess 284 configured to receive a blade extension 290 therein. The recess 284 includes an elongated central slot 286 formed therein and configured to receive a guide extension 292 therein. The recess 284 may further include a pair of elongated lateral slot 288 formed therein on either side of the central aperture 286.

A blade extension 290 may be provided to enhance the functionality of the medial retractor blade 18. The blade extension 290 is received within the recess 284 and is coupled to the medial blade 18 by the fastener 292. According to one embodiment, the blade extension 290 is slideably coupled to the medial blade 18. To enable this slidable coupling, the fastener 292 is slideably received within the elongated central aperture 286. The blade extension 290 includes a front surface 294 and a back surface 296. In use, the blade extension 290 is oriented such that the front surface 294 faces the operative corridor, and the back surface 296 engages the patient's soft tissue. The blade extension 290 may be generally curved such that the front surface 294 has a concave curvature and the back surface 296 has a convex curvature or it may the front and back may be generally flat. The blade extension 290 further includes a distal anchor element 298 provided thereon. The distal anchor element 298 comprises a roughened surface including a series of ridges and spike members that enable the clearing away of soft tissue from the surgical target site. The distal anchor element 298 has two aspects of curvature. The first aspect of curvature is that the distal anchor element 298 curves toward the back surface 296. The second aspect of curvature is that the front surface 294 maintains its concave curvature.

The result is that the distal anchor element 298 acts much the same way as a "boat anchor" in that it is capable of travelling along the surgical target site, displacing soft tissue until the distal anchor element 298 engages hard tissue such as bone. By way of example only, when used during a TLIF procedure such as the one described herein by example, the distal anchor element 298 advantageously removes soft tissue from the facet as it is being retracted, saving the surgeon from having to manually clean the facet. Due to its unique shape, the distal engagement element 298 will either penetrate the bone or become wedged underneath the bone. The blade extension 290 is slideably coupled to the medial blade 18 such that, upon tilting or other movement of the surgical retraction system 10, the blade extension 290 will remain stationary relative to the bone segment while the medial retractor blade 18 moves relative to the blade extension 290. The blade extension 290 is therefore capable of telescoping (i.e. extending or retracting) to conform to anatomy during retraction, both with and/or without manual adjustments from the surgeon. Thus, the blade elongates since it is secured distally at the bone and proximally at the retractor body 12. In this manner, the surgeon is able to further optimize, customize, and alter the operative corridor without having to disengage the retractor and/or any blades, while ensuring the exposure at the surgical target site (the base of the operative corridor) does not change, and thereby preventing previously retracted soft tissue from entering the operative corridor under the blade. Optionally, the blade extension 290 may be mechanically biased toward the extended position in order to ensure that its tissue clearing functionality is maximized. This may be accomplished, for example, by including a spring member (not shown) attached to the medial blade 18 and configured to bias the blade extension 290 in the distal direction.

FIGS. 31-34 illustrate an example of a hoop shim assembly 6 according to one embodiment of the present invention. The hoop shim assembly 6 includes a hoop portion 300 slideably engaged with a shim portion 302. The hoop portion 300 includes a hoop member 304, a first flange 306 and a second flange 308 extending proximally from the hoop member 304. The hoop member 304 is a generally circular member having a central aperture 310 configured to receive a bone anchor 7 therein. The hoop member 304 has a first, unlocked position having a first diameter allowing passage of the bone anchor 7 therethrough. In this first position, the head of the bone anchor 7 may pass through, but with resistance. The hoop member 304 further has a second, locked position, having a second diameter that does not allow passage of the head of the bone anchor 7 therethrough. Thus, when the hoop member 304 is in the locked position, the bone anchor 7 is secured to the hoop shim 6. As will be explained below, this secured engagement does not mean that the bone anchor 7 is immobilized—on the contrary it is a polyaxial engagement (as illustrated in FIGS. 58-61). The hoop member 304 may be optionally provided with an insert 312 (FIGS. 35-37) to provide protective interaction with the bone anchor 7. More specifically, the insert 312 protects the neck of the bone anchor 7 from a metal-on-metal contact with the hoop shim 6, which could ultimately weaken the bone anchor 7. The insert 312 may be composed of any suitable materials, including but not limited to polyetheretherketone (PEEK).

Figure 38:
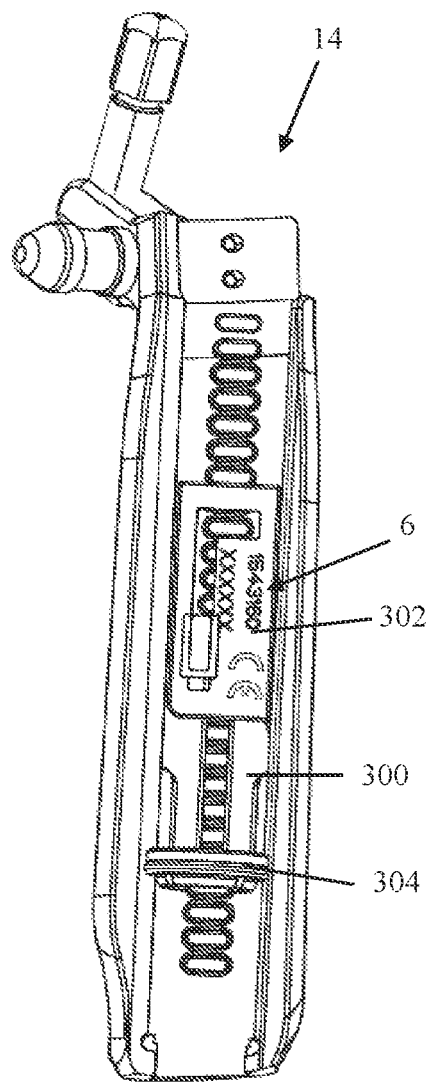
FIG. 38 is a front plan view of the hoop shim assembly of FIG. 31 being coupled to a retractor blade assembly of FIG. 22.

The first flange 306 is generally elongated and extends generally perpendicularly in a proximal direction from the hoop member 304. The first flange has a wing 314 extending at least partially along the length of the flange 306 from the proximal end toward the distal end. The wing 314 is dimensioned to engage one of the track grooves 252 of the first retractor blade 14 (and/or second retractor blade 16) to enable slidable engagement of the hoop shim assembly 6 with the retractor blade 14 (as shown in FIG. 38, for example). The first flange 306 further includes a tab member 316 projecting in a forward direction (i.e. same direction as the hoop member 304). The tab member 316 is generally rectangular and configured to slidably engage the vertical slot 338 of the shim portion 302. The tab member 316 has a generally U-shaped retaining pin 318 attached thereto that prevents the tab member 316 from becoming disengaged with the vertical slot 338 during use. By way of example only, the retaining pin 318 is welded to the tab member 316 during assembly of the hoop shim assembly 6, however other attachment methods are possible without departing from the scope of the present invention. For example, the tab member 316 and retaining pin 318 may be integrally formed with one another and then welded onto the first flange 306. Additionally, a retaining plate may be welded over the tab instead of the retaining pin.

The second flange 308 is generally elongated and extends generally perpendicularly in a proximal direction from the hoop member 304 opposite and generally parallel (in an initial position) to the first flange 306. The second flange 306 has a distal portion 320, a proximal portion 322, and an intermediate portion 324 positioned between the distal portion 320 and proximal portion 322. The distal portion 320 is attached to the hoop member 304, and has a first width. The proximal portion 322 has a second width that enables the proximal portion 322 to pass the knob 346 of the shim portion 302 and into the recess 344 of the shim portion 302. By way of example only, the first width is greater than the second width. The intermediate portion 324 has a third width that is greater than both the first and second widths, and a convex edge 326 extending from the proximal portion 322 to an apex 328. The intermediate portion 324 further includes a concave edge 330 extending between the apex 328 and the distal portion 320.

Figure 33:
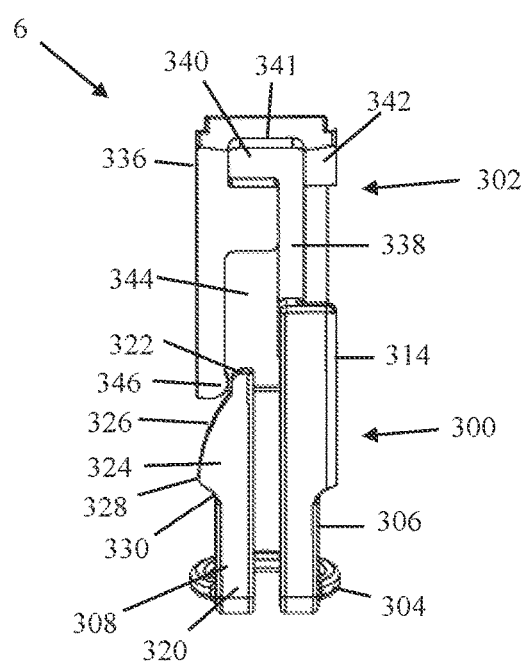
Figure 34:
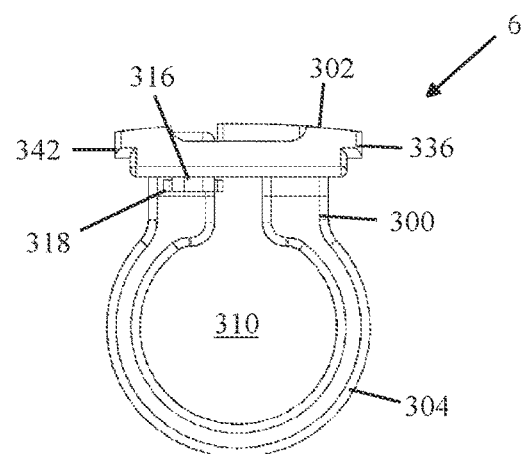

The shim portion 302 is a generally rectangular elongated member having a proximal end 332 and a distal end 334. The shim portion 302 further includes a first wing 336 extending substantially the length of one side of the shim portion 302 (e.g. the side that corresponds to the second flange 308 of the hoop portion 300). The first wing 336 is dimensioned to engage one of the track groove 252 of the first retractor blade 14 (and/or second retractor blade 16) to enable slidable engagement of the hoop shim assembly 6 with the retractor blade 14 (as shown in FIG. 36, for example). The shim portion further includes an elongated vertical slot 338 extending substantially the length of the shim portion 302. The vertical slot 338 is configured to slidably receive the tab member 316 therein. The shim portion 302 further includes a horizontal slot 340 positioned near the proximal end 332. The horizontal slot 340 is dimensioned to engage the distal projection 366 of the hoop shim removal tool 350, as described below. The horizontal slot has a ramped surface 341 extending toward the proximal end 332 of the shim portion 302. By way of example only, the vertical slot 338 and horizontal slot 340 are shown as one connected L-shaped aperture, however separate apertures are possible without departing from the scope of the invention. The shim portion 302 further includes a second wing 342 positioned near the proximal end 332 on the opposite side of the shim portion 302 from the first wing 336. The second wing 342 is dimensioned to align with the wing 314 of the first flange 306 during use (as shown in FIG. 33). The second wing 342 has the same function as the first wing 336. The shim portion 302 further includes a recess 344 formed within the back side of the shim portion. The recess 344 is dimensioned to receive at least a portion of the second flange 308 of the hoop portion 300, to enable the hoop shim 6 to transition to a locked position. The recess 344 also includes a knob 346 positioned at the distal end of the recess 344. The knob 346 functions to reduce the width of the opening of the recess 344 to prevent easy disengagement of the hoop portion 300.

In use, the hoop shim assembly 6 is preferably provided in a preassembled form in which the tab member 316 is engaged within the vertical slot 338 and the retaining pin 318 is welded to the tab member 316, preventing disengagement of the tab member 316 from the vertical slot 338. In the initial position, the proximal portion 322 of the second flange 308 is positioned within the recess 344 of the shim portion 302 and adjacent to the knob 346. In this initial position, a bone anchor 7 may be loosely engaged to the hoop member 304, within the central aperture 310. To secure the bone anchor 7 to the hoop shim assembly 6, the hoop shim assembly 6 is moved from its initial unlocked position to a final locked position. To achieve this, the first and second flanges 306, 308 are slidably advanced proximally along the shim portion 302. The convex edge 326 of the intermediate portion 324 of the second flange 308 includes a relatively gradual curvature. As the second flange 308 is advanced past the knob 346 and into the recess 344, the interaction between the knob 346 and the convex edge 326 causes the second flange 308 to deflect toward the first flange 306. The width of the intermediate portion is preferably such that the intermediate portion still engages the inner wall of the recess and remains in the deflected position. The concave edge 330 has a relatively steep concave curvature, and thus the apex 328 will not reverse past the knob 346 absent sufficient applied force. Once the apex 328 is beyond the knob 346 and within the recess 344 of the shim portion 302, the hoop shim assembly 6 is in a locked position, and the bone anchor 7 is successfully and securely engaged thereto (e.g. FIG. 44).

This final, locked position is illustrated by way of example only in FIGS. 35-37. The bone anchor 7 is positioned within the aperture 310 of the hoop portion 300. An insert 312 is provided within the hoop member 304. Notably, the head 8 of the bone anchor 7 is positioned proximally of the hoop member 304, and in this position is unable to pass through the aperture. The threaded shank 9 of the bone anchor 7 extends distally of the hoop member 304.

Figure 39:
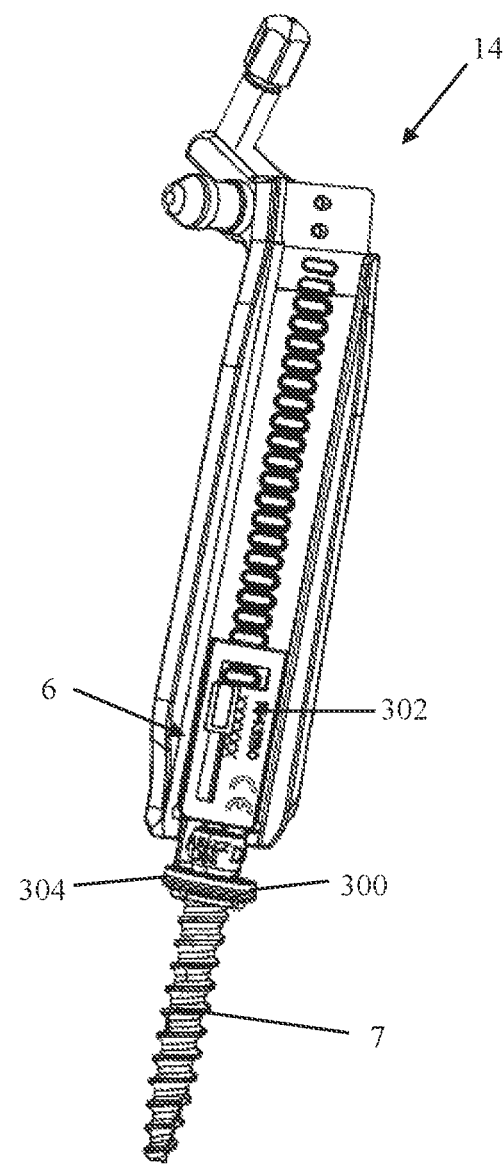
FIG. 39 is a front plan view of the hoop shim assembly locked and engaged with the bone anchor of FIG. 35 coupled to a retractor blade assembly of FIG. 22.

FIG. 38 illustrates a hoop shim assembly 6 engaged with a retractor blade 14, in an unlocked position and without a bone anchor engaged thereto. FIG. 39 illustrates a hoop shim assembly 6 lockingly engaged to a bone anchor 7 and engaged with a retractor blade 14. The hoop shim assembly 6 may be coupled with the bone anchor 7 and/or retractor blade 14/16 either before or during a surgical procedure. In one embodiment, the hoop shim assembly 6, bone anchor 7, and retractor blade 14 are provided in a pre-assembled state. In such an embodiment, the hoop shim assembly 6 is first coupled to a retractor blade 14 as described above, in an unlocked position. A bone anchor 7 is then introduced such that the neck region is within the central aperture 310. At this point the engagement between the hoop shim assembly 6 and bone anchor 7 is unsecure. The hoop shim assembly 6 is then moved into a locked position, securing the bone anchor 7 therein. The bone anchor 7, hoop shim assembly 6, and retractor blade 14 may then be coupled to an inserter, for example such as the inserter 400 shown and described in relation to FIGS. 64-78 below, and advanced simultaneously through the operative corridor to the surgical target site. Alternatively, the bone anchor 7 may be placed within the surgical target site and then engaged with the hoop shim assemblies 6 by slipping the heads 8 of the bone anchors 7 within the central aperture 310 of the hoop shim assembly 6 and then locking the hoop shim assemblies 6. Moreover, the hoop shim assembly 6 may be intraoperatively engaged and/or disengaged from an implanted bone anchor 7 within a surgical target site. This feature is advantageous in that it allows the operative corridor to be registered to an anatomical landmark, and also removed from that registration, for example if the user wanted to expand the operative corridor beyond the implanted bone anchors. A further advantage of this feature is that it allows for intraoperative exchange of retractor blades 14, 16, for example to swap out for a longer or shorter blade, without losing the ability to register the operative corridor to an anatomical landmark, and without changing the position of the retractor body 12.

Figure 40:
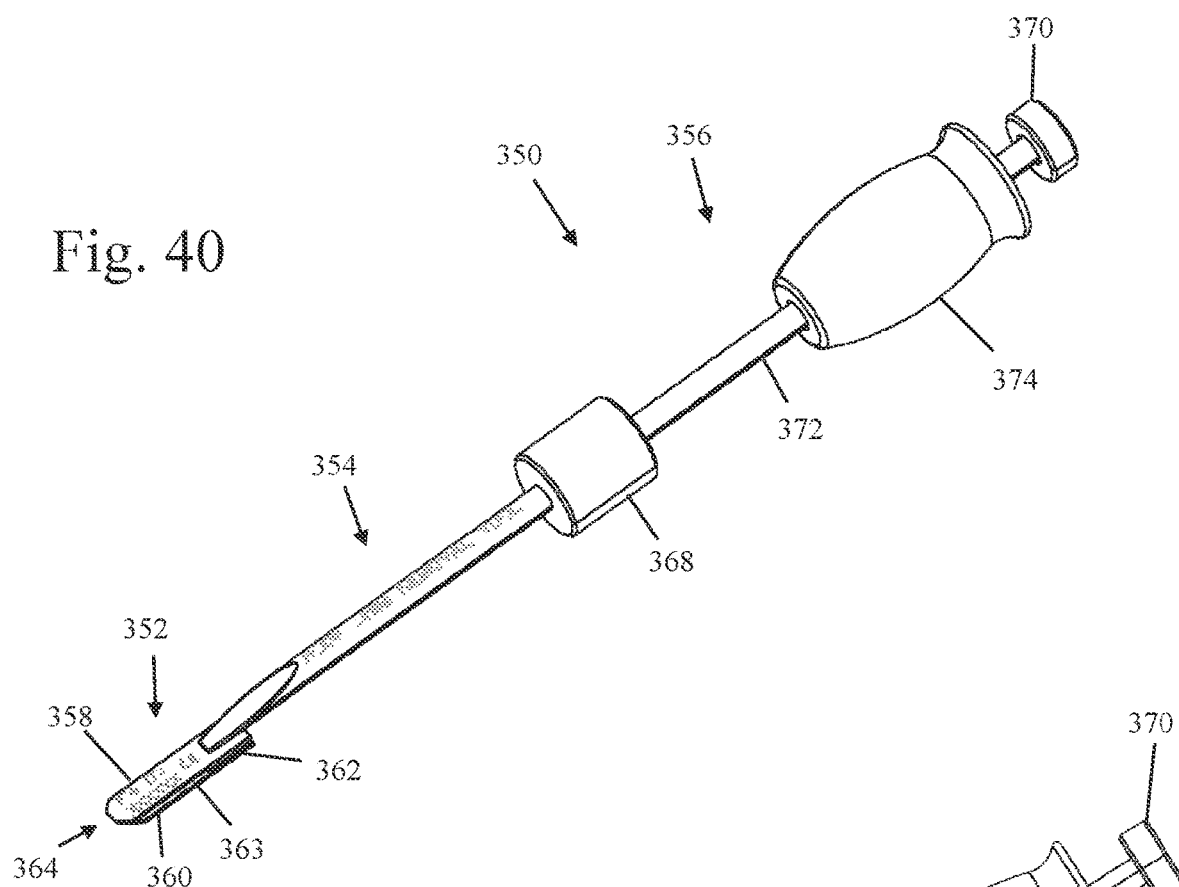
FIGS. 40-41 are perspective and side plan views, respectively, of an example of a hoop shim removal tool according to one embodiment of the present invention.
Figure 41:
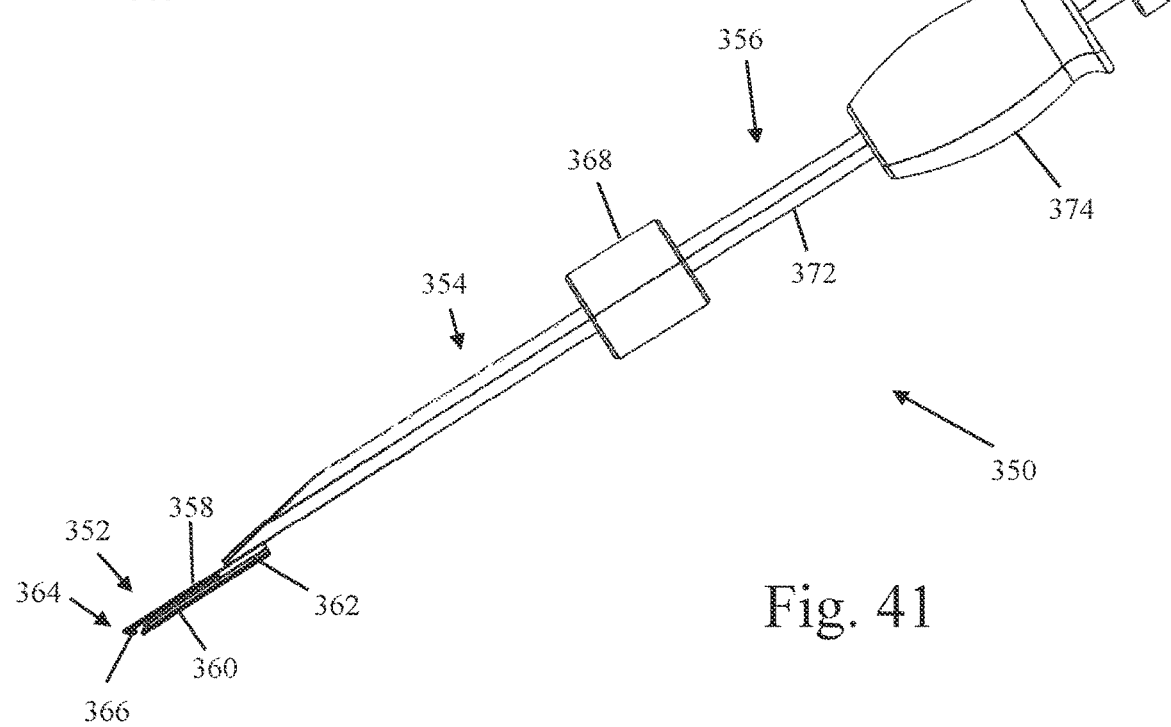
Figure 42:
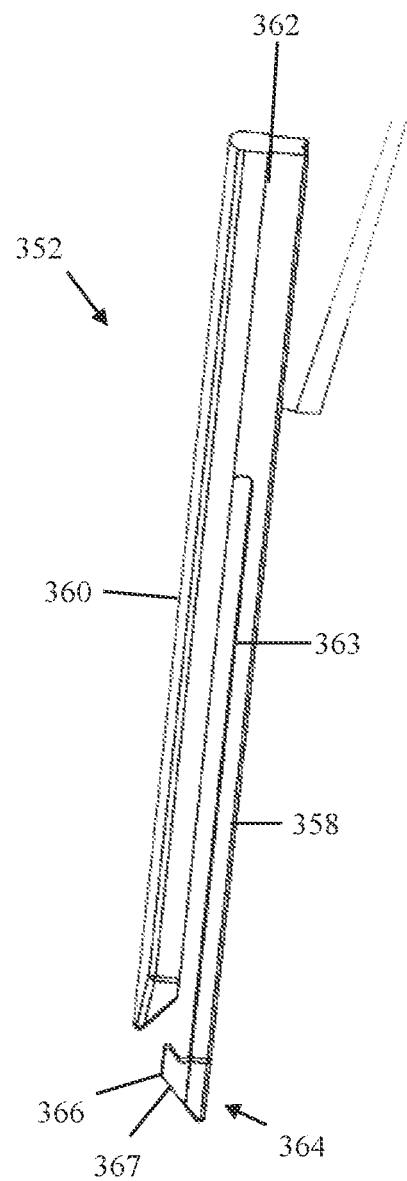
FIG. 42 is a side plan view of a distal engagement region forming part of the hoop shim removal tool of FIG. 40.

FIGS. 40-42 illustrate an example of a hoop shim removal tool 350 according to one embodiment of the present invention. The hoop shim removal tool 350 is a generally elongated instrument having a distal engagement member 352, an intermediate shaft 354, and a proximal slap hammer 356 attached thereto. The distal engagement member 352 includes a top panel 358, a bottom panel 360, and a base 362 positioned between the top and bottom panels 358, 360 at the proximal end of the distal engagement member 352. The top panel 358 has a distal portion 364 that extends beyond the end of the bottom panel 360. The distal portion 364 includes a projection 366 configured to engage the horizontal slot 340 of the hoop shim assembly 6. As illustrated in FIG. 42, the projection 366 is oriented such that there is an acute angle formed between the projection 366 and the top panel 358. The projection 366 further includes a ramped leading surface 367 configured to deflect off the shim portion 302 as the distal engagement member 352 is advanced into engagement with the shim portion 302. The bottom panel 360 includes a pair of lateral wings 363 positioned on either side of the bottom panel 360. The lateral wings 363 are dimensioned to engage the track grooves 252 of the first retractor blade 14 (and/or second retractor blade 16) to enable slidable engagement of the hoop shim removal tool 350 with the retractor blade 14 (as shown in FIG. 43, for example).

The slap hammer 356 includes a distal stop 368, a proximal stop 370, an elongated shaft 372 extending between the distal and proximal stops 368, 370, and a slapper 374 slidably positioned on the elongated shaft 372. The slapper 374 is configured to slide along the elongated shaft 372 between the distal and proximal stops 368, 370. The slap hammer 356 is designed to allow a user to generate a tremendous force in the proximal or distal direction. For example, a user would grab the slapper 374 and exert a force in a proximal direction by "slapping" it against the proximal stop 370.

Figure 45:
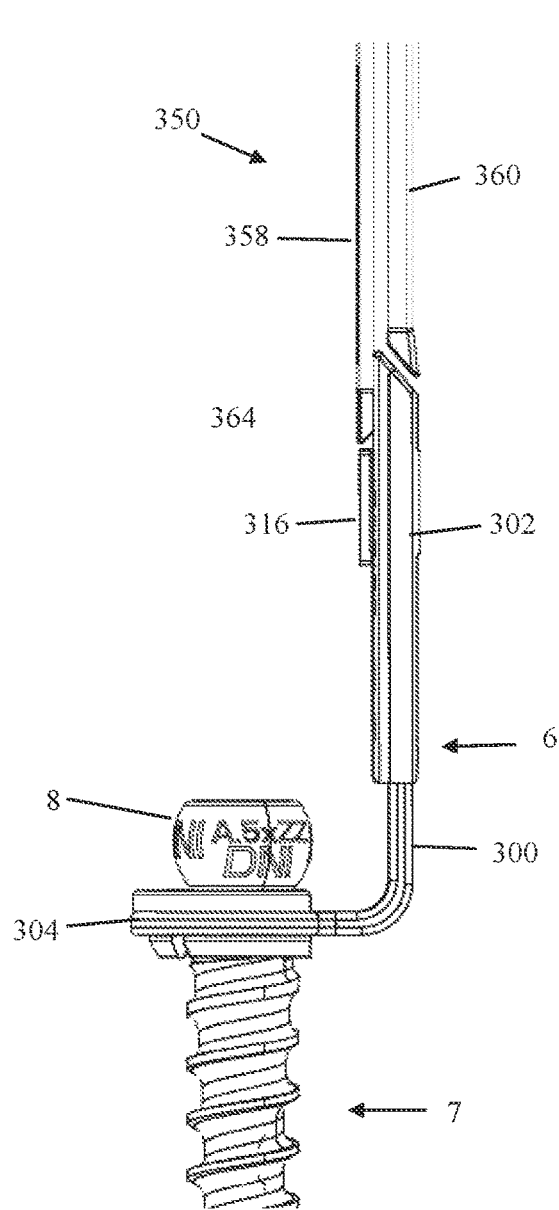
Figure 46:
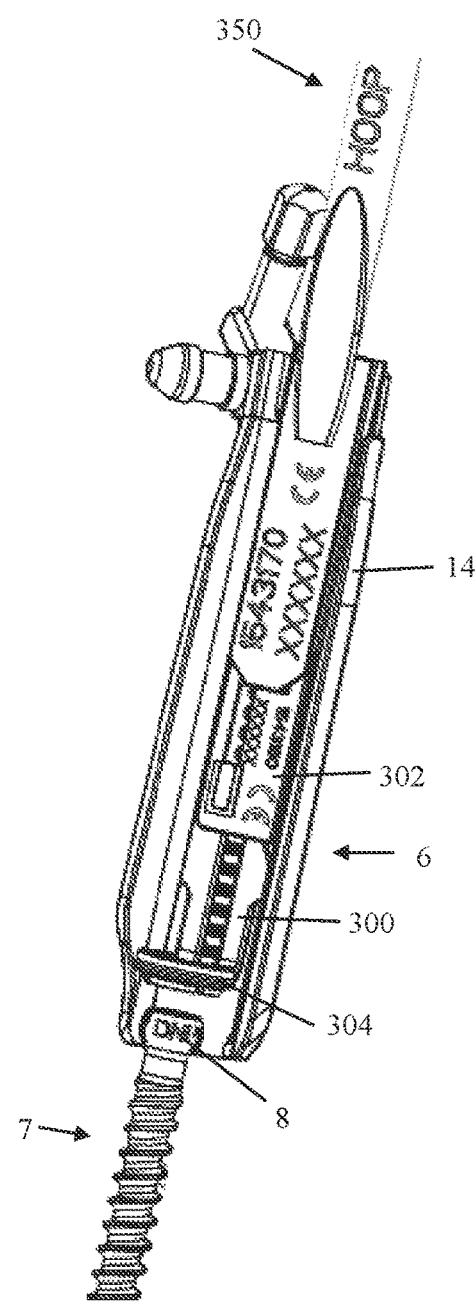
FIG. 46 is a perspective view of the hoop shim assembly unlocked and disengaged from the bone anchor of FIG. 35 coupled to a retractor blade assembly of FIG. 22, and also coupled to the hoop shim removal tool of FIG. 40 after disengagement of the hoop shim assembly from the bone anchor.
Figure 47:
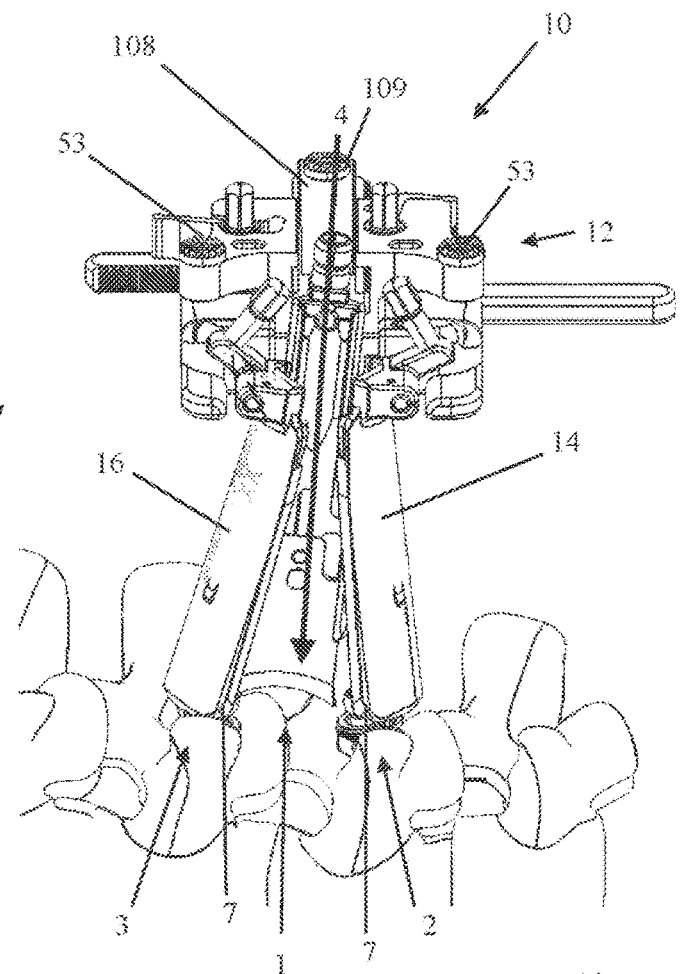
FIGS. 47-48 and 50-53 are perspective views of the surgical fixation system of FIG. 1 during different stages of use on a spinal segment.
Figure 48:
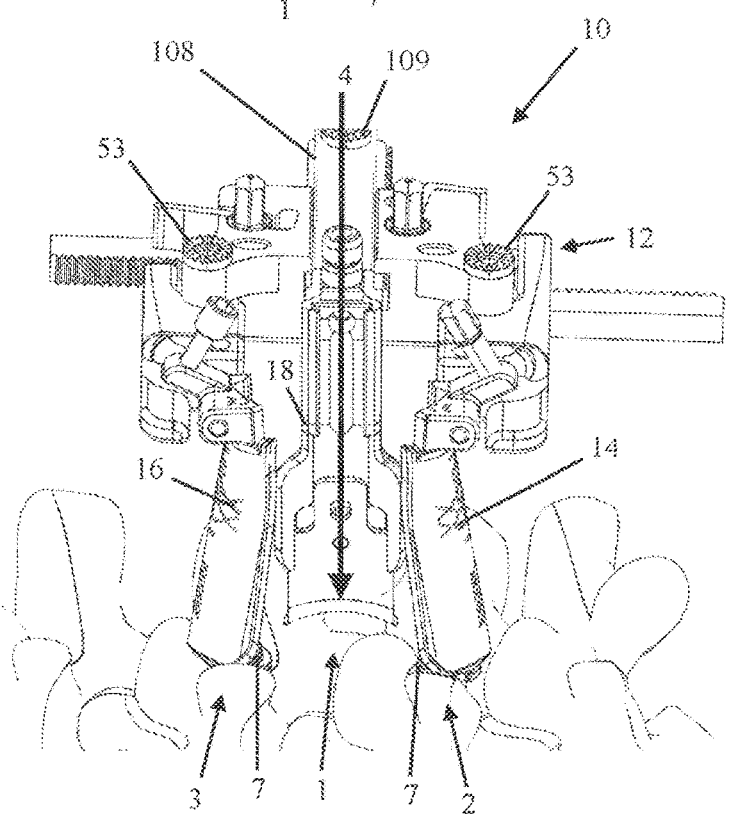
Figure 49:
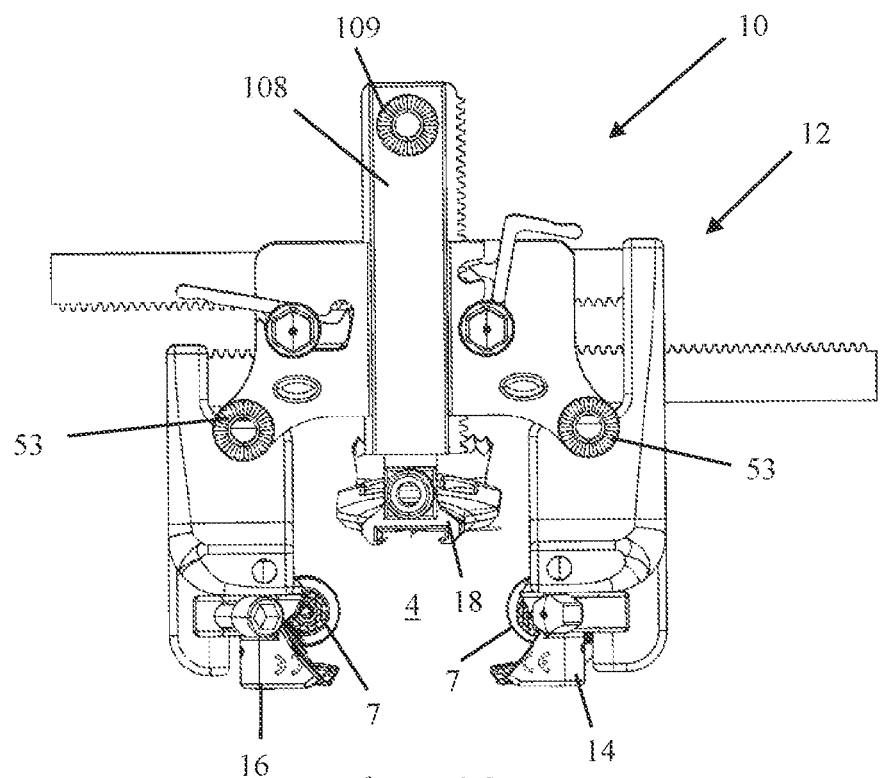
FIG. 49 is a top plan view of the fully assembled surgical fixation system of FIG. 1.
Figure 50:
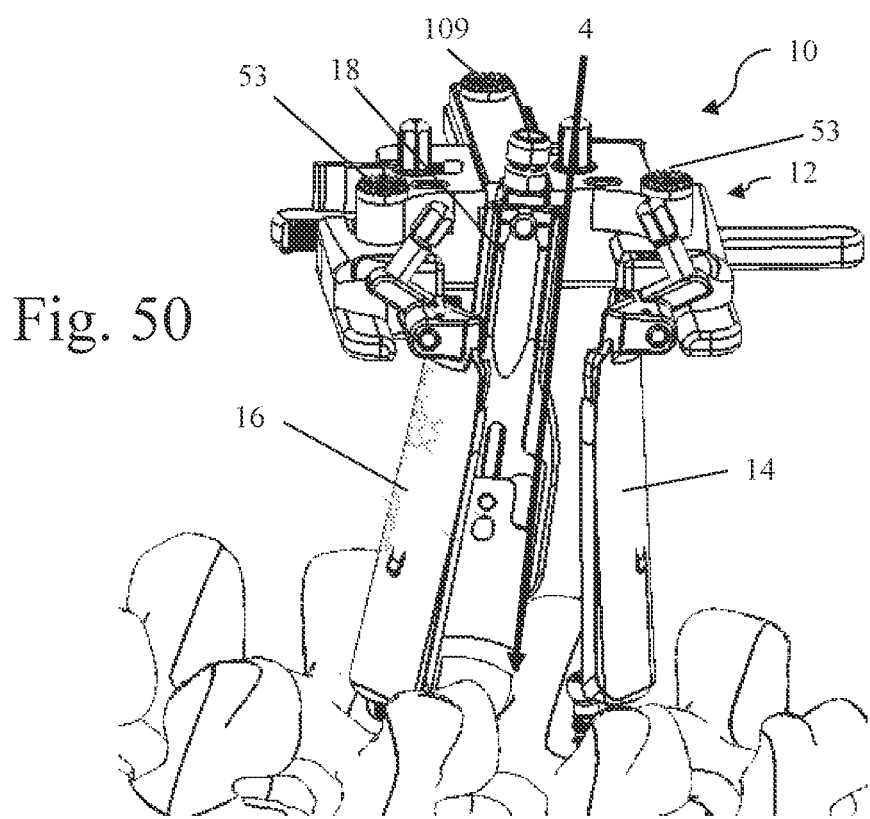

FIGS. 43-46 illustrate the steps of using the hoop shim removal tool 350 to remove the hoop shim 6. First, as illustrated in FIGS. 43-44, the hoop shim removal tool 350 is slidably engaged to the retractor blade 14 as described above. The distal engagement member 352 is advanced along the retractor blade 14 until the projection 366 engages the locked hoop shim assembly 6. As the projection 366 is being advanced over the shim portion 302 between the proximal end 332 and the horizontal slot 340, the top panel 358 is outwardly displaced. As the projection 366 engages the horizontal slot 340, the top panel 358 snaps back into place and a secure engagement is achieved between the hoop shim removal tool 350 and the hoop shim assembly 6, as illustrated in FIGS. 44 and 45. The user then slaps the slapper 374 against the proximal stop 370 to generate a proximal force on the shim portion 302 of the hoop shim assembly 6. This force should be great enough to at least pull the knob 346 past the intermediate portion 324 of the second flange 306, causing the hoop shim assembly 6 to return to its unlocked position. In the unlocked position, the aperture 310 has an increased diameter. Another slapping of the slapper 374 should supply enough force to pull the hoop member 304 past the head 8 of the anchor member 7, thus disengaging the hoop shim 6 from the anchor member 7 (as shown in FIG. 46) and retrieving the hoop shim assembly 6 from the retractor blade track. Of course, a single slapping of the slapper 374 may be sufficient to both unlock the hoop shim assembly 6 and disengage the hoop member 304 from the anchor head 7. The retractor blade 14 is no longer registered to the anchor member in the surgical fixation site, but can rather move freely and/or be removed entirely.

Although the hoop shim removal tool 350 has been described by way of example with regard to a specific embodiment, other mechanisms are possible. For example, the slap hammer may be replaced by a Kerrision-style trigger without departing from the scope of the present invention.

The surgical retraction system 10 described herein may be used in a variety of different surgical techniques involving a variety of areas of the body. By way of example only, the surgical retraction system 10 is ideal for performing a novel procedure for performing a transforaminal lumbar interbody fusion (TLIF) procedure on a human spine. For the purposes of illustration, the example technique will be explained with regard to a one-level TLIF, in which two adjacent vertebrae are fused across a single intervertebral space. However, it should be noted that the system and method disclosed herein may be suitable to be used on multiple vertebral levels without departing from the scope of the present invention. Moreover, the system and methods described herein may be used and/or adapted for use in a variety of different surgical techniques involving a variety of areas of the body without departing from the scope of the present invention.

Prior to performing this technique, the patient is positioned in the prone position, (i.e. on his/her stomach). The first step in the method is to locate the pedicles that will in part define the surgical target site. The next step is to create an incision in the patient's skin above the surgical target site (in this example, an intervertebral disc space between two adjacent vertebrae). Specifically, the incision should be made between the pedicles along the lateral border. K-wires are then placed via a jamshidi through the small incisions into the pedicles on adjacent vertebrae. To assist with this, the surgeon may use a navigated guidance system, for example one shown and described in commonly owned PCT Application Nos. PCT/US07/11962, entitled "Surgical Trajectory Monitoring System and Related Methods," filed May 17, 2007, and PCT/US08/12121, entitled "Surgical Trajectory Monitoring System and Related Methods," filed on Oct. 24, 2008, the entire contents of which are each incorporated by reference into this disclosure as if set forth fully herein. Once the K-wires are positioned properly within the target pedicles, the surgeon may create an initial surgical corridor through finger dissection. The distance from the vertebral body and surface of the skin is measured using a ruled dilator or another suitable instrument. Another tool may be used to measure the appropriate screw length by indicating how far into bone the K-wire has been advanced. The next step in the procedure is pilot hole formation. Navigated guidance and fluoroscopic imaging may continue to be used to help the surgeon ensure the proper approach and trajectory into the pedicles is being maintained. A cannulated tap is then passed over each of the K-wires to tap an appropriate sized pilot hole into each of the pedicles. Optionally, the cannulated tap may be substantially insulated and provided with an electrified tip, or alternatively a second insulated cannula may be provided while the tap is electrified, in order to enable pedicle integrity testing during pilot hole formation. This function is similar to the procedure shown and described in U.S. patent application Ser. No. 10/836,105, now issued as U.S. Pat. No. 7,664,544, filed Apr. 30, 2004, entitled "System and Methods for Performing Percutaneous Pedicle Integrity Assessments," the complete disclosure of which is hereby incorporated by reference into this document as if set forth fully herein. Once this is completed, the appropriate length of retractor blades 14, 16 is selected and assembled with the hoop shim assembly 6, an anchor member 7, and inserter 400 as shown and described herein. This step is repeated for both the first and second retractor blades 14, 16.

Figure 54:
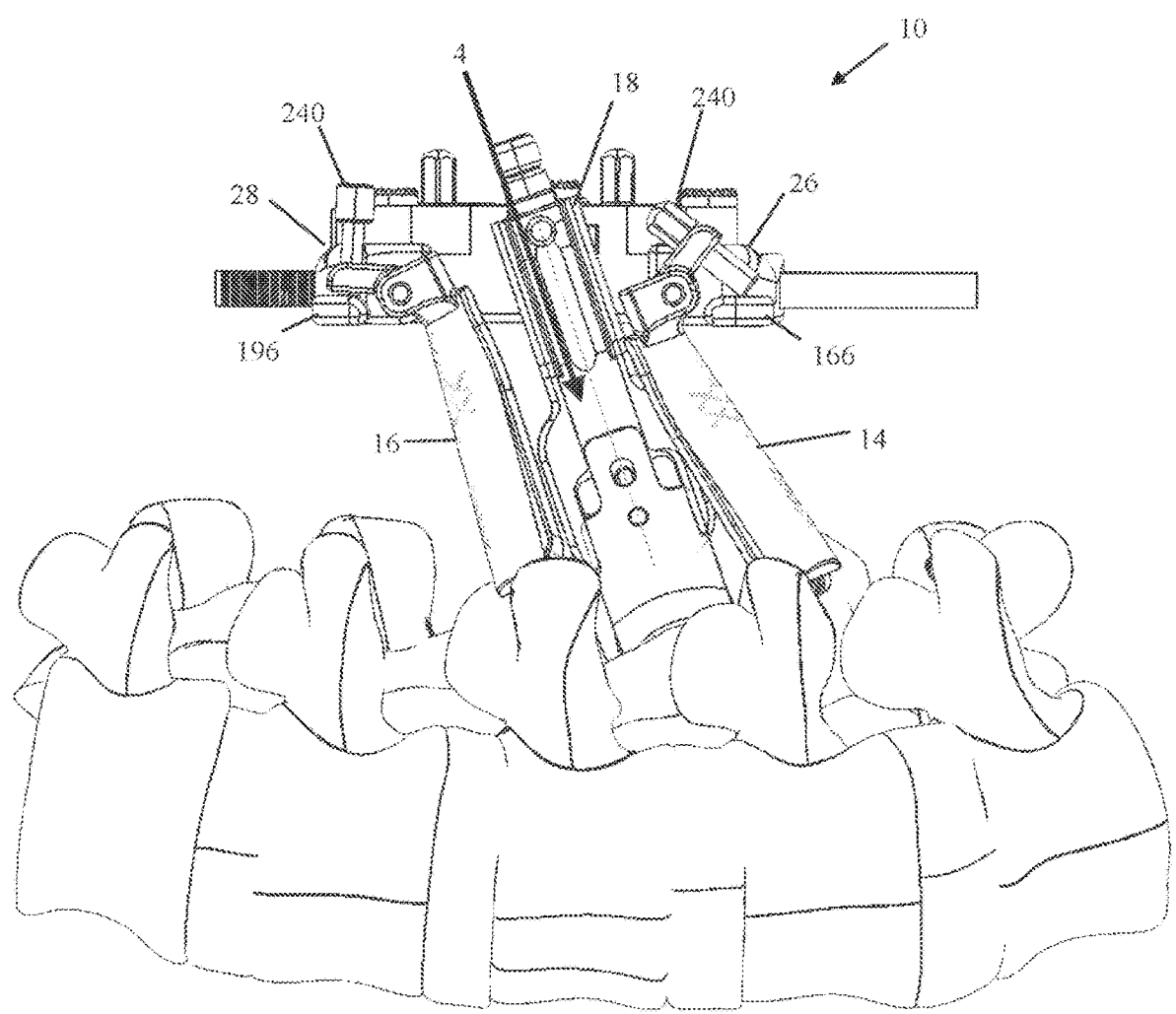
FIGS. 54 and 55 are front plan and perspective views, respectively, of the fully assembled surgical fixation system of FIG. 1 in use on a spinal segment, particularly illustrating the extreme angulation capability of the system.
Figure 55:
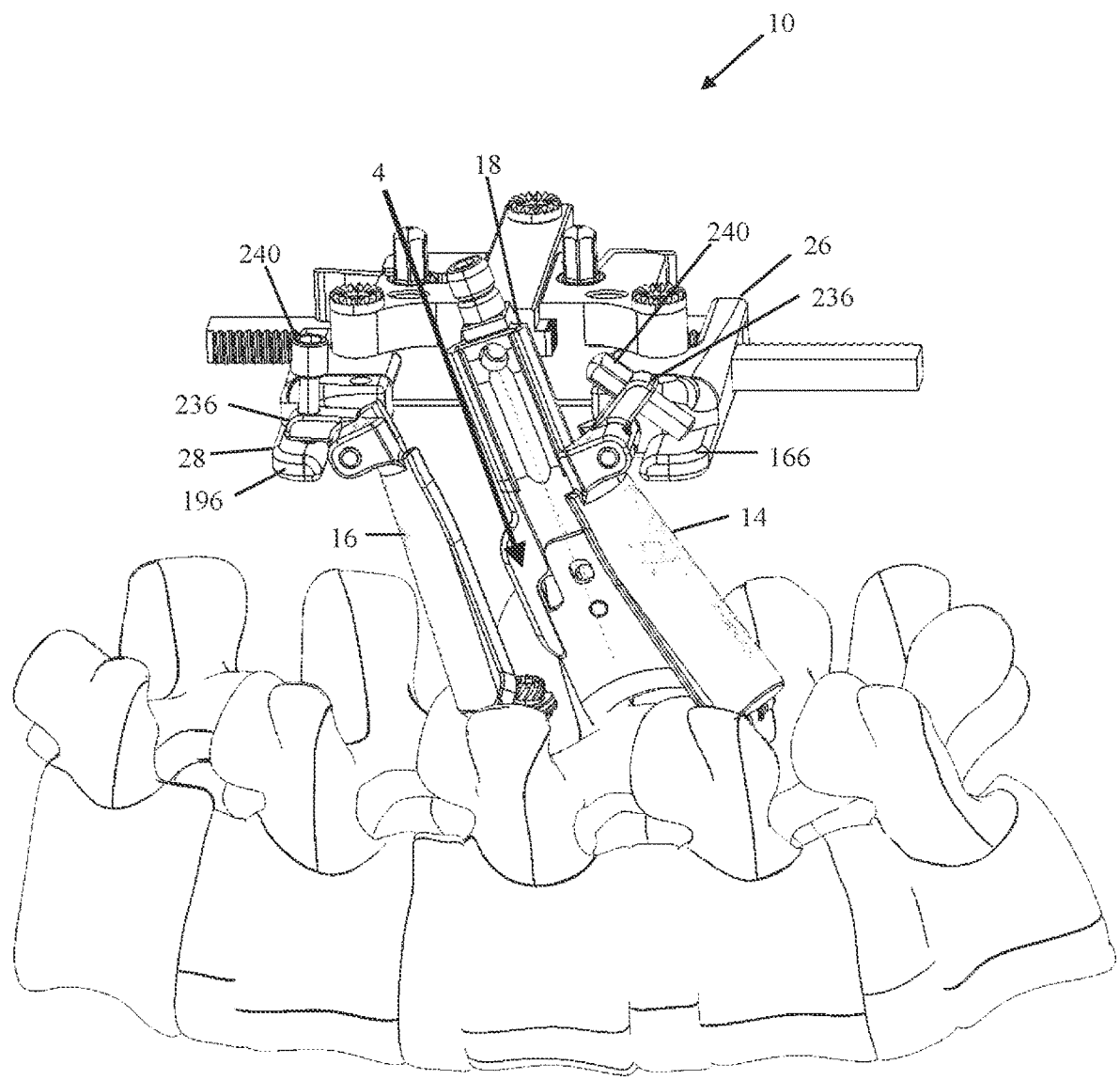
Figure 56:
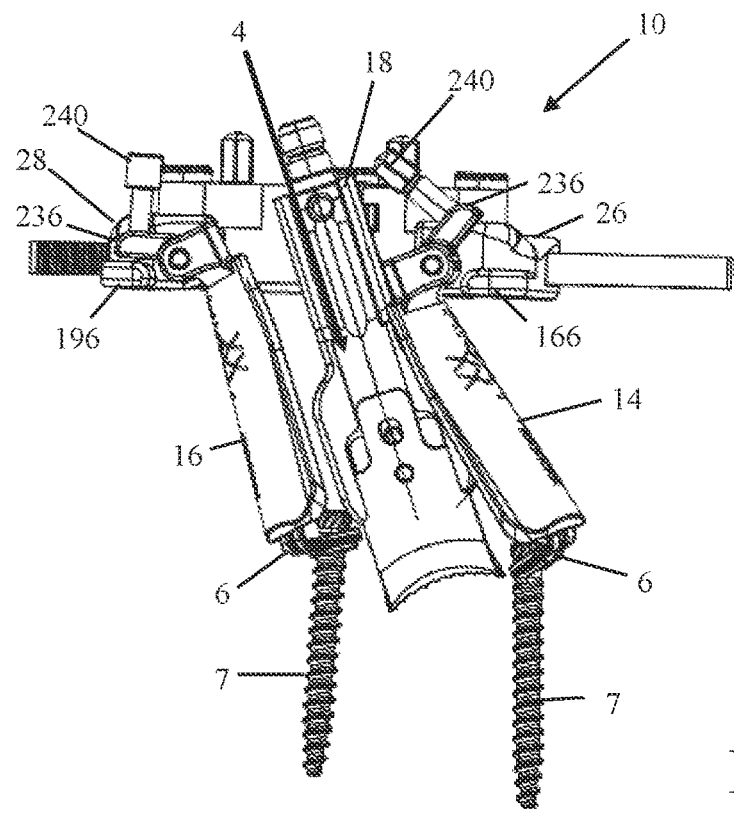
FIG. 56 is the front plan view of the fully assembled surgical fixation system of FIG. 49 with the spinal segment removed.

Once the blade-shim-anchor assembly has been securely created, the anchor member 7 (with hoop shim 6 and first retractor blade 14 securely attached) is advanced through the initial operative corridor and driven into the pilot hole in a first of the adjacent pedicles. This process is repeated with the second retractor blade 16 assembly and the second pilot hole, until the first and second retractor blades 14, 16 are protruding from the initial incision, with the distal ends of the blades being securely registered to the anchor members 7 via the hoop shim assemblies 6. At this point, the first and second retractor blades 14, 16 may be attached to the retractor body 14 as described above. The surgeon may then operate the retractor body 12 to cause the retractor blades 14, 16 to move in cranial and caudal directions, respectively, at the skin level. Because the distal portions of the retractor blades 14, 16 are securely (and polyaxially) registered to the implanted anchor members 7, the anchor members 7 will not move. However, the angle of the retractor blades 14, 16 relative to the anchor members 7 may be adjusted to a desired angle (for example as shown in FIG. 54, and the operative corridor will be established. Once established, the retractor body 12 may be locked to an articulating arm (not shown) by either one of the attachment members 53 of the retractor body 12, or attachment members 109 of the medial rack 108. Using a suitable tool or a finger, the surgeon then releases soft tissue from the facet. A medial retractor blade 16 may then be inserted and retracted as desired and as described above. As mentioned previously, the medial retractor blade may operate to clear remaining soft tissue from the facet. The medial retractor blade 16 may be angled to match the operative corridor by pivoting the blade in a plane that is transverse to the longitudinal axis of the medial rack 108. In this fashion, the entire operative corridor may be established at an angle that is suitable for superior access to the disc space.

At this point, the tissue retraction assembly 10 is positioned as shown by way of example in FIGS. 47-50. The surgeon has established a primary operative corridor 4 to a surgical target site 1, and has distinct landmarks (i.e. the implanted anchor members 7) delineating the cranial and caudal boundaries of the relevant operative window (the respective pedicles of the superior and inferior vertebrae 2, 3). The surgeon can now perform the necessary steps to clean out the intervertebral disc space and perform the interbody fusion procedure. This example procedure continues with a facetectomy in which at least a portion of the facet joint is removed, allowing access to the intervertebral disc space. The disc space is prepared using techniques generally known in the art, including disc brushes, scrapers, etc. The interbody implant is then inserted into the cleaned out disc space. By way of example only this may include, but not be limited to, inserting one or more artificial or allograft implants within the intervertebral space. According to one example, the implant may be inserted and positioned obliquely across the disc space. If necessary, the surgeon may use the tissue retraction system 10 to distract the disc space without expanding the incision at the patient's skin and without any further instrumentation. This tissue distraction feature of the disclosed device is described in greater detail below.

Figure 51:
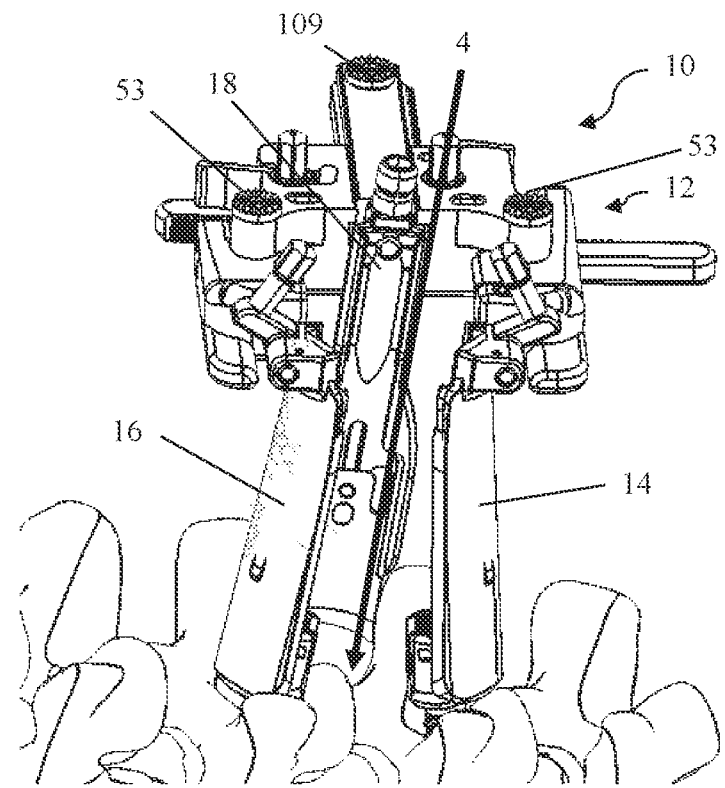
Figure 52:
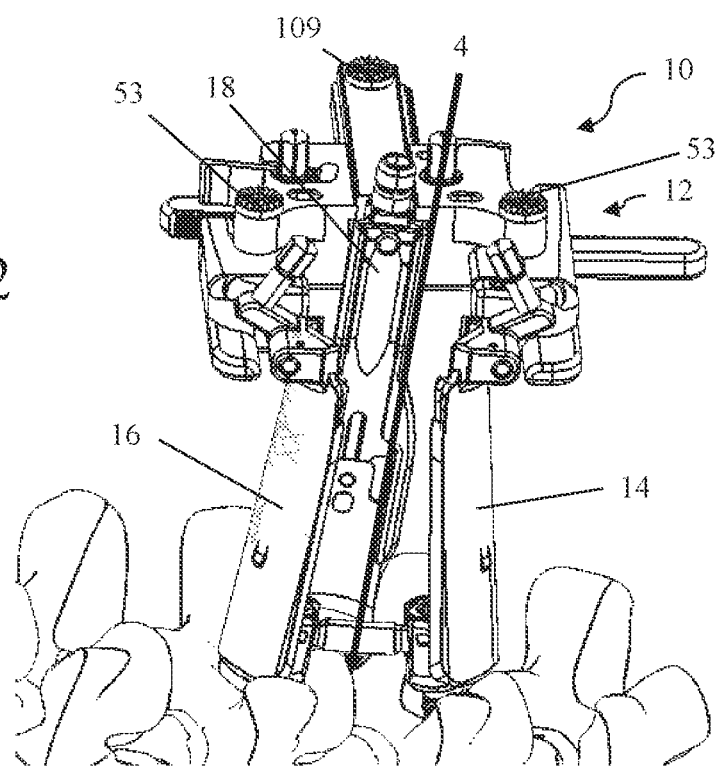
Figure 53:
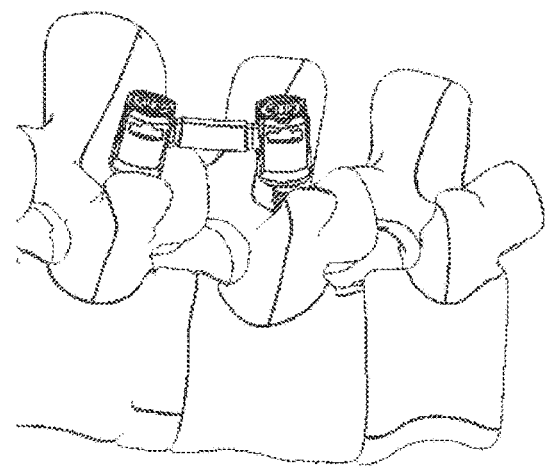

After placement of the interbody implant, the distraction of the screws is released, and the hoop shim assemblies 6 are removed using the hoop shim removal tool 350 as described above. The surgeon then "opens" the retractor slightly in a caudal-cranial direction using the thumbscrews 240 on the blades (opposed to the rack assembly 22) as described below to increase the space around the pedicle screws. The pedicle screw tulips are then inserted onto the pedicle screws (FIG. 51). A posterior fixation rod is then placed within the tulips (FIG. 52), followed by compression (if necessary) and locking of the rod. With the procedure completed, the retractor can be returned to a "closed" position and then removed from the patient, closing the operative corridor (FIG. 53). The surgeon will then close the operative wound, completing the procedure.

The surgical fixation system 5 shown and described herein by way of example boasts a variety of advantageous features. An advantage of the present system is that it allows for intraoperative adjustment of the operative corridor, and in particular the angle of approach (in all directions) to the surgical target site with assurance that the exposure will not stray from the desired target site because the distal ends of the retractor blades 14, 16 are fixed in position at the target site. This advantage is accomplished by one or more features of the present invention. For example, the retractor blades 14, 16 that define the exposure are fixed to the target site with a polyaxial engagement (e.g. the hoops shim assemblies 6 have a polyaxial interaction with the bone anchors 7). The retractor blades 14, 16, 18 are each capable of multiaxial movement relative to the retractor body 12. The first and second retractor blades 14, 16 are capable of being locked in an angulated position.

FIGS. 54-57 illustrate extreme angulation capabilities of the tissue retraction system 10. Once the primary operative corridor has been established as described above, it may become necessary to alter the position of the operative corridor, for example to be able to access intervertebral disc material that otherwise would not be able to be accessed. With the tissue retraction system 10 disclosed herein the angle of the operative corridor 4 may be altered without changing the surgical window at the target site—only the approach angle changes. This is enabled by the multiaxial movement capabilities of the retractor blades 14, 16, 18. In this context, "multiaxial" means having the ability to pivot in a number of different directions relative to an initial position along one axis (or in a single plane). For example, each of the retractor blades 14, 16, has the ability to pivot in both a caudal and cranial direction. Similarly, the medial blade 18 has the ability to pivot in a caudal and cranial direction. It is contemplated that the retractor blades 14, 16, 18 may also be capable of polyaxial movement. In this context, "polyaxial" means having the ability to pivot in a number of different directions relative to an initial position along a number of axes (or in a number of different planes). Thus, blades may also be provided with the ability to pivot in a medial and/or lateral direction, or in a generally arcuate manner without departing from the scope of the present invention. Similarly, the medial retractor blade 18 may also be provided with the ability to pivot in a medial and/or lateral direction, or in a generally arcuate manner without departing from the scope of the present invention.

Figure 57:
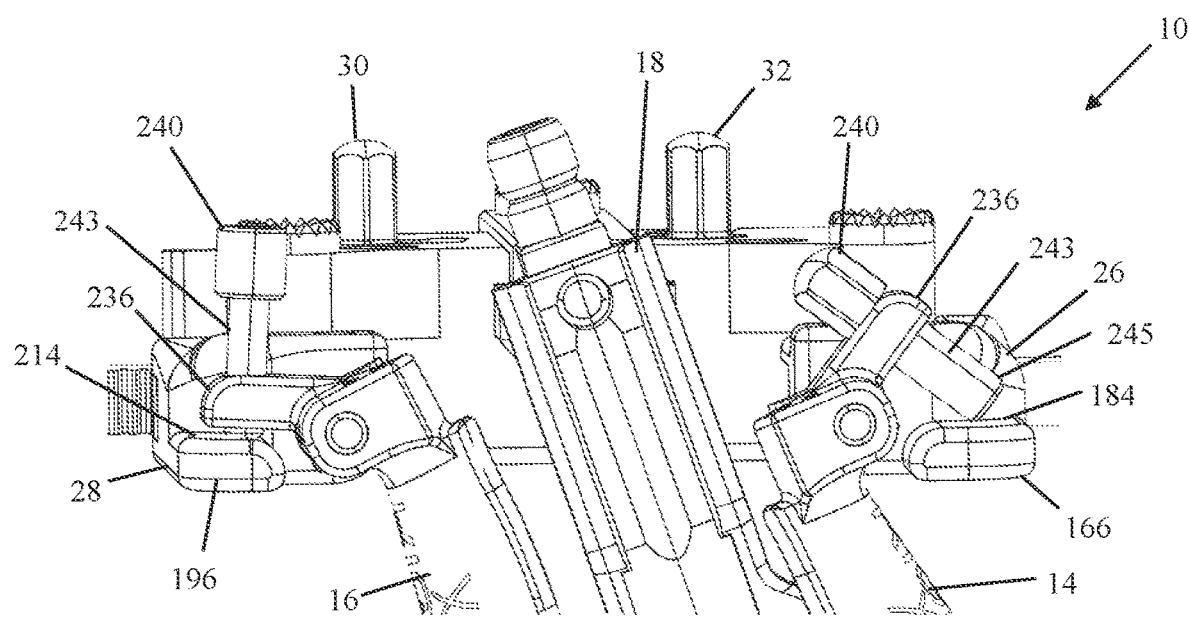
FIG. 57 is a close-up plan view of the fully assembled surgical fixation system of FIG. 49, illustrating in particular the lockability of the system in an extreme angulation state.
Figure 58:
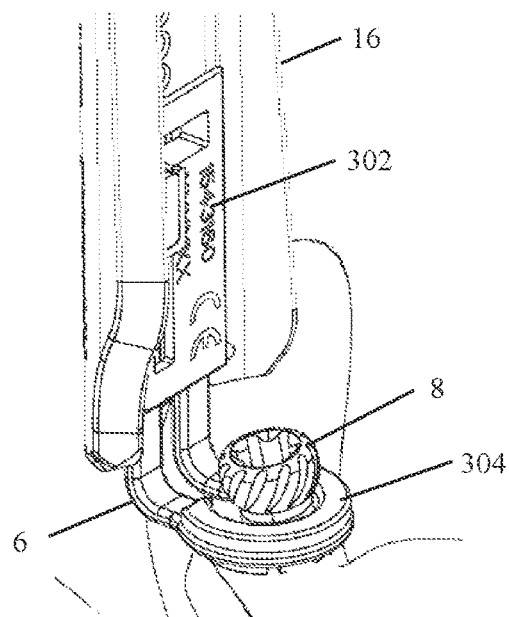
FIGS. 58-61 are perspective views of a locked hoop shim assembly and bone anchor combination of FIG. 35, with the bone anchor implanted within a bony segment, illustrating in particular the polyaxial engagement between the hoop shim assembly and bone anchor.
Figure 59:
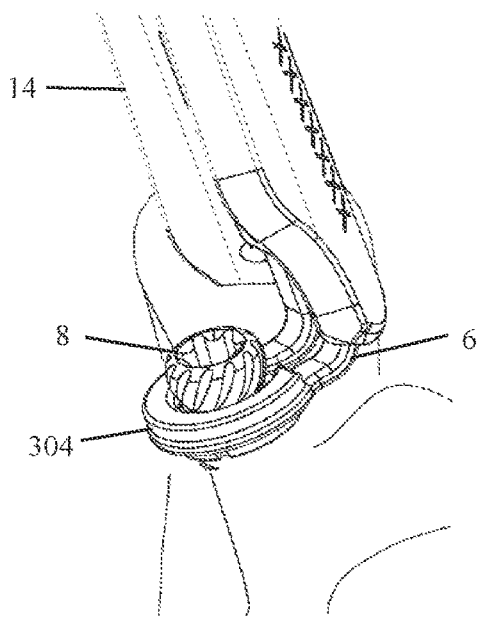
Figure 60:
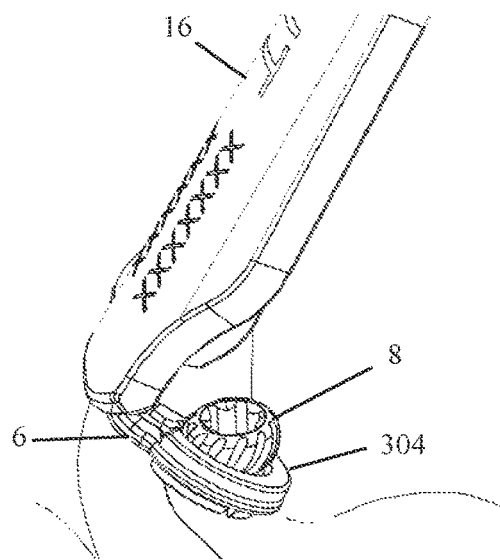
Figure 61:
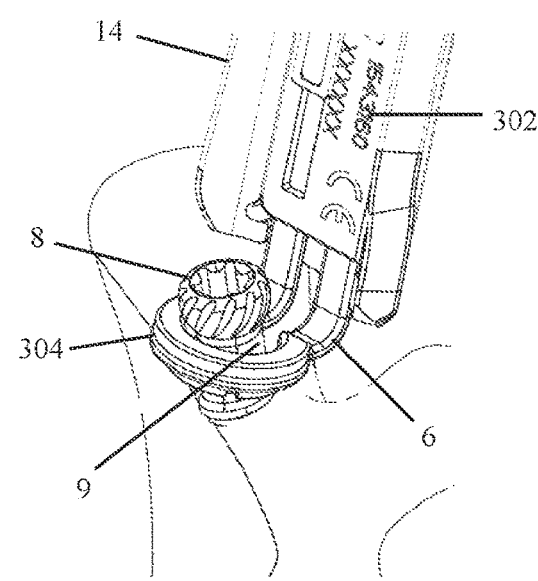

As mentioned previously, the result of this pivoting is that the tissue retraction system 10 described herein is capable of establishing and maintaining an angled operative corridor 4 to a surgical target site. The tissue retraction system 10 is able maintain this angulation due to the thumb screws 240 that are provided on each of the retractor blades 14, 16. As described earlier in relation to FIGS. 22-26, the flange 236 and thumb screw 240 of the first retractor blade 14 interact with the second flange 166 of the first arm member 26 to enable the lockable angulation feature of the first retractor blade 14. Similarly, the flange 236 and thumb screw 240 of the second retractor blade 16 interact with the second flange 196 of the second arm member 28 to enable the lockable angulation feature of the second retractor blade 16. In one embodiment, the aperture 238 on the flange 236 and the thumb screw 240 are both threaded such that there is a threaded engagement between the flange 236 and thumb screw 240. As best illustrated in FIG. 57, once a desired angulation of the first retractor blade 14 is established, the thumb screw 240 is rotated clockwise to advance the threaded shaft 243 through the threaded aperture 238 until the distal tip 245 of the thumb screw 240 engages the top surface 184 of the second flange 166. At this point, the user stops rotating the thumb screw 240 and the first retractor blade 14 is prevented from pivoting in the opposite direction due to the threaded engagement of the flange 236 and thumb screw 240, as well as the engagement between the distal tip 245 of the thumb screw 240 and the top surface 184 of the second flange 166. This process is repeated for the second retractor blade 16. For example, once a desired angulation of the second retractor blade 16 is established, the thumb screw 240 is rotated clockwise to advance the threaded shaft 243 through the threaded aperture 238 until the distal tip 245 of the thumb screw 240 engages the top surface 214 of the second flange 196. At this point, the user stops rotating the thumb screw 240 and the second retractor blade 16 is prevented from pivoting in the opposite direction due to the threaded engagement of the flange 236 and thumb screw 240, as well as the engagement between the distal tip 245 of the thumb screw 240 and the top surface 214 of the second flange 196.

The medial retractor blade 18 may be provided with a locking element or be allowed to freely pivot. However, once the first and second retractor blades 14, 16 are locked in position, the operative corridor 4 is established and will not move whether or not the medial retractor blade 18 is locked in position.

FIGS. 58-61 illustrate the polyaxial engagement between the hoop shim assembly 6 and the anchor member 7. Due to the unique structure of the hoop member 304 and the head 8 of the anchor element 7, the hoop shim assembly 6 (and by extension the retractor blade 14/16) is able to maintain secure engagement to the anchor element 7 at a variety of angulations, including variable angulations. For example the hoop member 304 fits securely but loosely over the head 8 of the anchor member 7 to allow for locking of the hoop shim assembly 6 to the anchor member 7 but also allowing for polyaxial engagement therewith. This interaction between the hoop member 304 and anchor member 7 will serve several functions. First it provides a temporary but secure attachment for the retractor blades 14/16 to help keep the operative corridor secure during the surgical procedure and act as fixed anatomical landmarks for the surgeon, provided the surgeon knows exactly where the bone anchors are placed. In other words, the operative window at the surgical target site will not move even if the position of the retractor body 12 were to move, or even if the angles of the blades 14/16 were to alter, because the blades 14, 16 are registered to the anchor members 7, which are already implanted in the bone. Secondly, this interaction provides a pivot point for the retractor assembly, allowing the surgeon to tilt the retractor assembly (and therefore the operative corridor) while maintaining the proper placement of the distal end of the operative corridor (e.g. the space between the anchor members 7). Another benefit to this feature is that the retractor body 12 is always securely registered to the patient. Yet another benefit of this feature is that it enables multi-axial maneuverability of the retractor blades 14/16. More specifically, each retractor blade is able to tilt in a caudal direction or cranial direction (or even medial or lateral directions) without adversely affecting the engagement between the hoop shim assembly 6 and the anchor member 7.

A second advantage of the tissue retraction system 10 disclosed herein is that it functions not only as a soft tissue retractor but also may function as a distracter capable of moving the adjacent vertebrae apart in order to distract the intervertebral disc space in a caudal-cranial direction. There are at least two distinct ways in which this can be accomplished. The first is by locking the retractor blades 14, 16 in a desired orientation as described above and then operating the first toggle 30 of the rack member 22 to cause the retractor blades 14, 16 to move apart from one another, thereby distracting the disc space. With this first instance, there would necessarily be an expansion of the operative wound at the skin level, because the retractor body 12 is working to expand the entire operative corridor. The general shape of the operative corridor (e.g. angulation of the retractor blades 14, 16) remains constant but the width of the operative corridor expands.

The second, alternative method of distracting the disc space involves maintaining the first and second rack members 58, 60 in a stationary position, and then using the thumb screws 240 on the first and second retractor blades 14, 16 to cause the distal ends of the retractor blades 14, 16 to migrate apart from one another. Since these distal ends are attached to the implanted bone anchors 7, the result is a separation of the vertebral bodies. However, since the retractor body 12 remains constant, there is no enlargement of the surgical wound at the skin level. The general conical shape of the operative corridor itself changes, as the angulation of the blades 14, 16 also changes. This type of distraction can potentially have less detrimental effect to the patient because the skin incision is relatively unaltered. Referring again to FIG. 57, in order to accomplish this distraction, the user starts with the first and second retractor blades 14, 16 locked in position such that the distal tip 245 of the thumb screw 240 of the first retractor blade 14 is engaged with the top surface 184 of the second flange 166 of the first retractor arm 26, and the distal tip 245 of the thumb screw 240 of the second retractor blade 16 is engaged with the top surface 214 of the second flange 196 of the second retractor arm 28. At this point, the user would rotate one or both of the thumb screws 240 in a clockwise direction (to enable increased distraction) or in a counterclockwise direction (to decrease the distraction).

For the sake of simplicity, this process will be further described in relation to the first retractor blade 14 only, however it will be understood that the process is the same for the second retractor blade 16 as well. As the user rotates the thumb screw 240 when the distal tip 245 is engaged with the top surface 184 of the second flange 166 of the first retractor arm 26, flange 236 will effectively travel in a proximal direction relative to the shaft 243 of the thumb screw 240, since the distal tip 245 is prevented from travelling in a distal direction by the second flange 166. This causes the distal end of the retractor blade to swing outward, or away from the working channel. Since the distal end is engaged to a bone anchor 7 via a hoop shim assembly 6 as described above, the movement of the distal end of the retractor blade will cause the bony segment to be displaced in the same direction (away from the working channel). This causes distraction of the disc space. This process can be performed independently for each retractor blade 14, 16, thus enabling further customization of the operative corridor and/or surgical target site.

Figure 62:
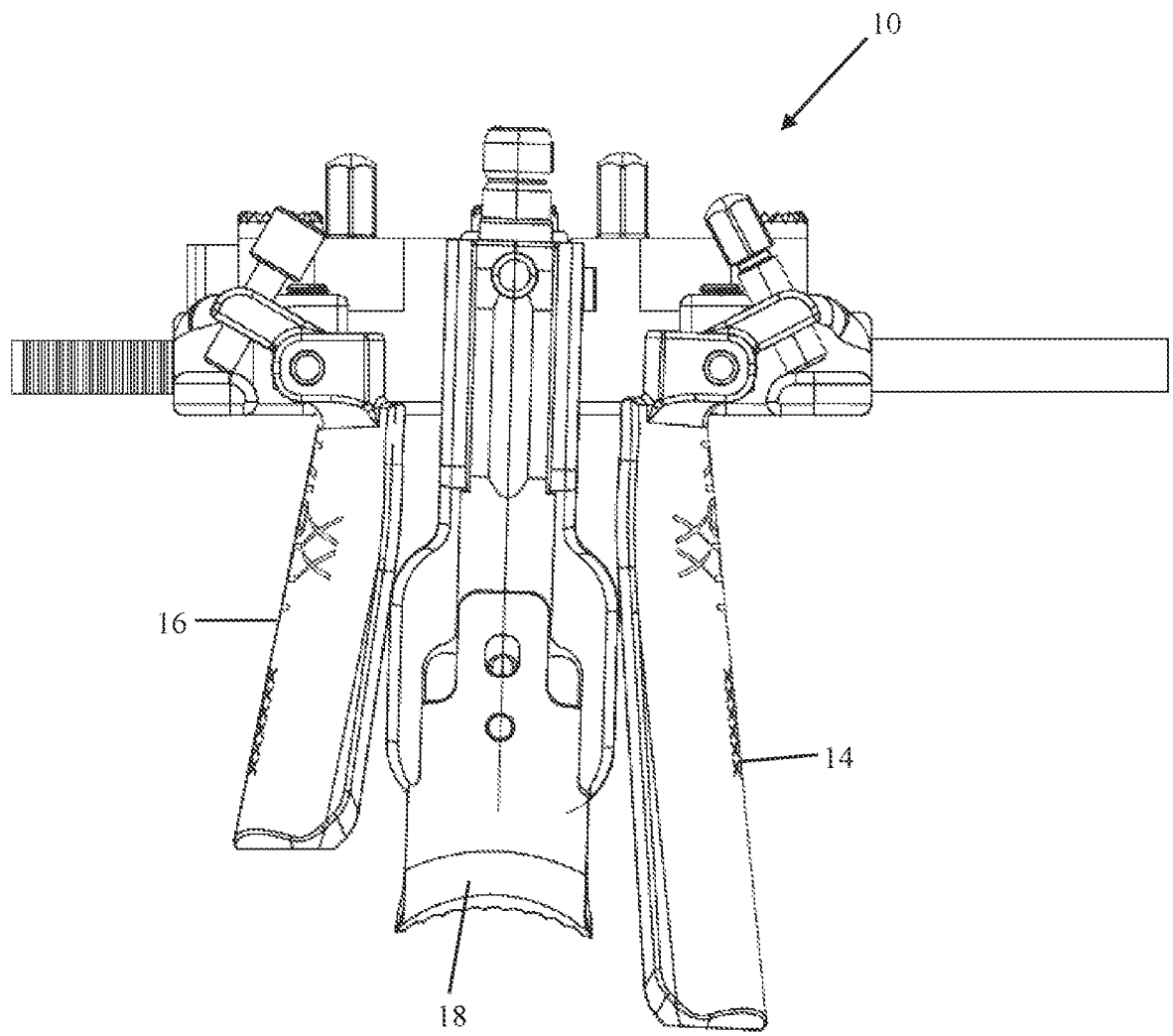
FIGS. 62 and 63 are front plan and perspective views, respectively, of the tissue retraction system of FIG. 6 having retractor blades of different lengths.
Figure 63:
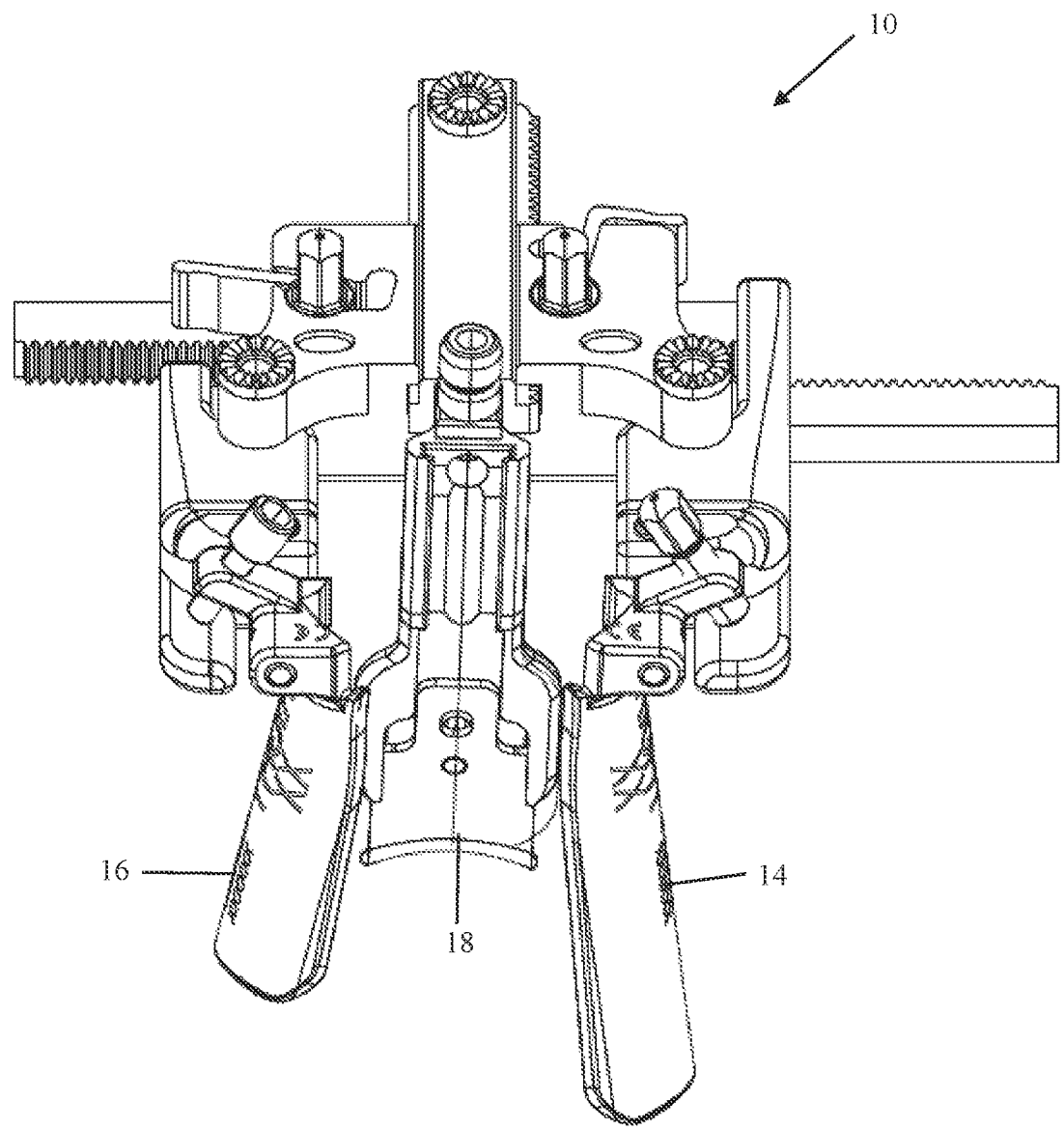

A third advantage of the tissue retraction system 10 described herein is the ability to intraoperatively exchange retractor blades 14, 16, 18. For example, this may be useful in situations in which the user desires one blade to be longer than the other. FIGS. 62-63 illustrate option for different sized blades. Because the blades 14, 16 are independently insertable, and are also inserted prior to the retractor body 12 being attached, an opportunity exists for a surgeon to elect multiple sized retractor blades depending upon the type of procedure to be performed. For example, if the surgeon is anticipating the need for extreme angulation in a particular direction, he or she may choose to use a longer retractor blade to accommodate for increased angle of one of the retractor blades. The interchangeability of the retractor blades allows for customization of the operative corridor.

Figure 64:
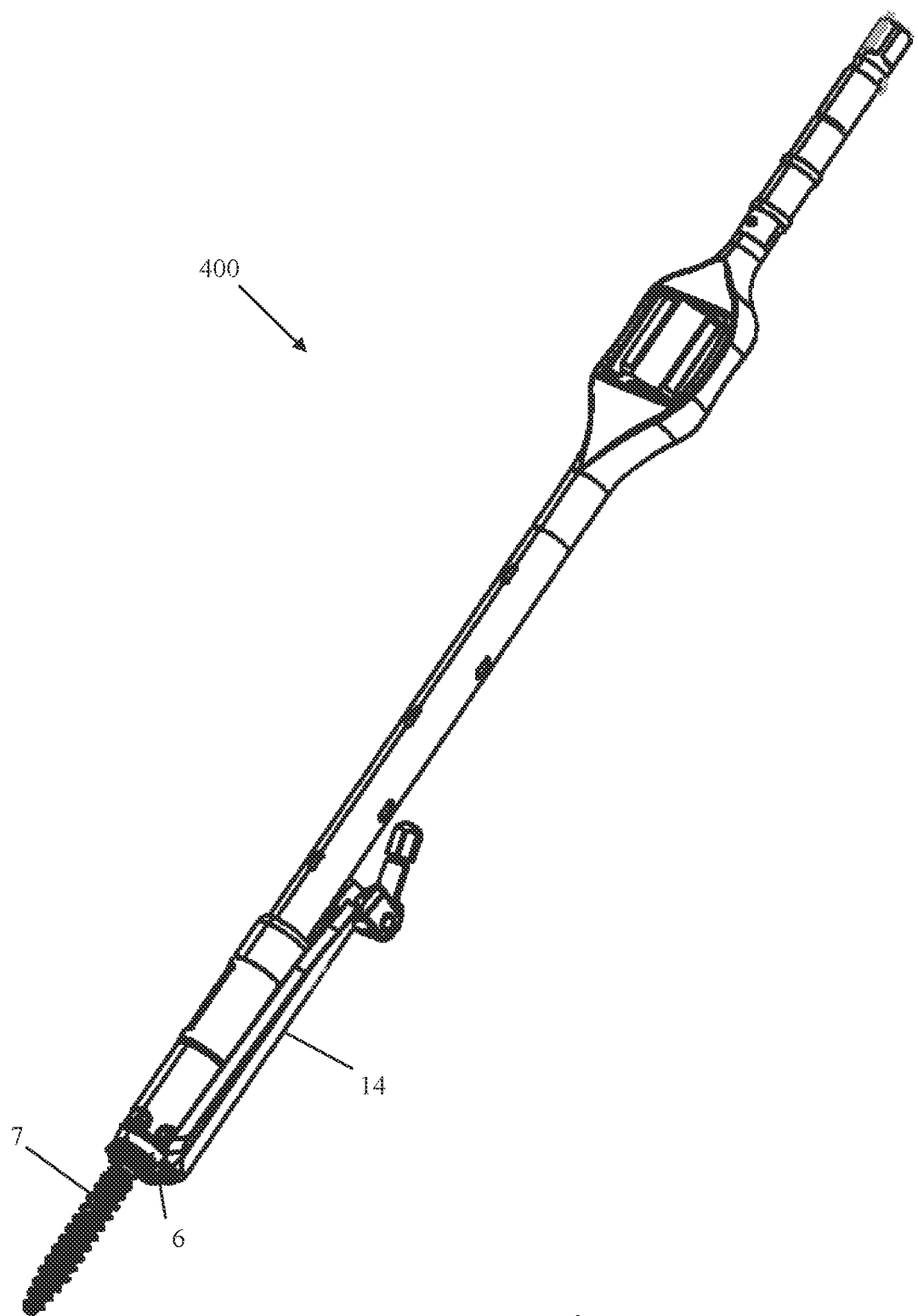
FIG. 64 is a perspective view of an example of an inserter according to one embodiment of the present invention, coupled to a bone anchor and hoop shim assembly of FIG. 35 and retractor blade of FIG. 22.
Figure 65:
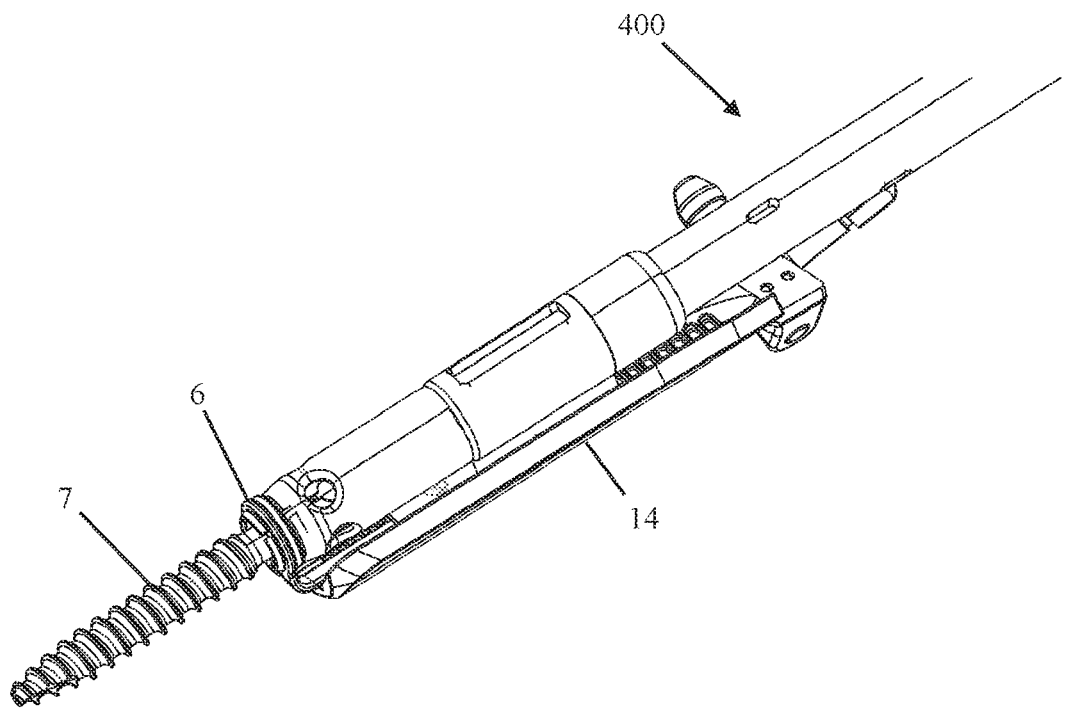
FIG. 65 is a perspective view of a distal region of the inserter, bone anchor, hoop shim assembly, and retractor blade combination of FIG. 64.

FIGS. 64-67 illustrate an example of an inserter 400 for use with the tissue retraction system 10 of the present invention. As mentioned previously, the bone anchor 7, hoop shim assembly 6, and retractor blade 14 may then be coupled to an inserter, and advanced simultaneously through the operative corridor to the surgical target site. FIGS. 64 and 65 illustrate a bone anchor 7, hoop shim assembly 6, and retractor blade 14 coupled to the inserter 400. In order to couple the various components together prior to insertion through an operative corridor, the first step is to slidably engage the unlocked hoop shim assembly 6 with the retractor blade 6 as described above. The bone anchor 7 is then loosely coupled with the hoop shim assembly 6. The hoop shim assembly 6 is then locked with the bone anchor 7 engaged. The inserter 400 is then slidably engaged to the retractor blade 14 (as described below), advanced toward the bone anchor 7, and then releasably coupled to the bone anchor as described below. Once this coupling has occurred, the insertion assembly is very secure due to the fact that each component (bone anchor 7, hoop shim assembly 6, retractor blade 14 and inserter 400) is coupled to two other components at the same time. Specifically, the bone anchor 7 is coupled to the hoop shim assembly 6 and inserter 400. The hoop shim assembly 6 is coupled to the bone anchor 7 and retractor blade 14. The retractor blade 400 is coupled to the hoop shim assembly 6 and the inserter 400. The inserter 400 is coupled to the bone anchor 7 and retractor blade 14. The result is a secure and robust engagement that allows the user to safely advance the components to the surgical target site.

Figure 66:
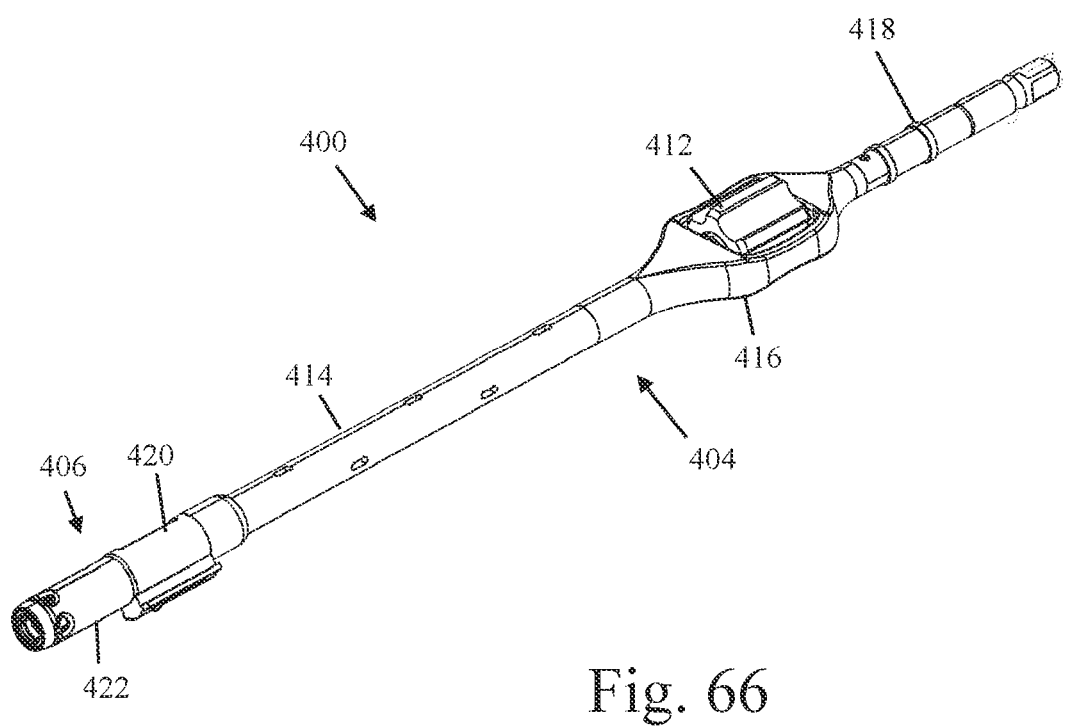
FIG. 66 is a perspective view of the inserter of FIG. 64.

Referring to FIGS. 66 and 67, the inserter 400 includes a receiver assembly 402, a driver assembly 404, and an engagement assembly 406. Broadly, the receiver assembly 402 includes a receiver member 408, an elongated shaft 410, and a thumbwheel 412, and functions to securely engage the exterior of the head 8 of the anchor member 7. The driver assembly 404 includes cannulated driver 414, a housing 416, and a proximal engagement member 418, and functions to engage the head of the bone anchor 7 and drive it into the bone. The engagement assembly 406 includes a blade engagement member 420 and functions to engage the inserter 400 and retractor blade 14, as well as enable the locking of the head 8 of the anchor member 7 within the receiver assembly 402.

Figure 70:
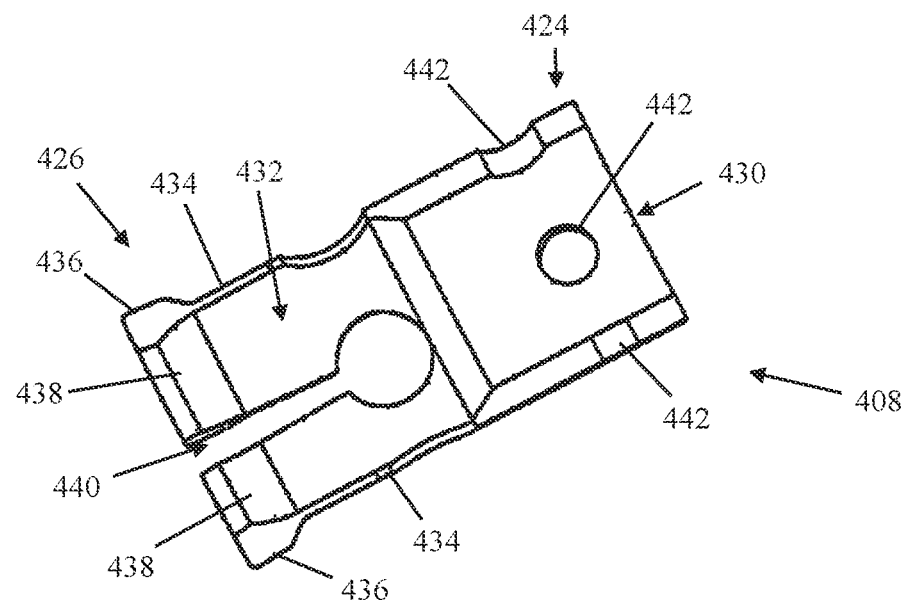

Referring to FIGS. 68-70, the receiver member 408 is a generally cylindrical member having a proximal end 424, a distal end 426, and a body 428 extending therebetween. The receiver member 408 further includes a central lumen 430 extending therethrough from the proximal end 424 to the distal end 426. At the proximal end 424, the central lumen 430 has a first diameter. At the distal end 426, the central lumen 430 has a second diameter that is greater than the first diameter, forming a receptacle 432 configured to receive the head 8 of the anchor member 7 therein. The distal end 426 further includes a plurality of deflectable flanges 434 arranged radially about the distal end 426. The deflectable flanges 434 include a raised surface 436 extending radially outward at the exterior of the distal end 426. Within the central lumen 430, the deflectable flanges 436 also include a concave surface 438 such that the opening 440 of the central lumen 430 has a smaller diameter than that of the receptacle 432. The raised surfaces 436 interact with the distal aperture 494 of the engagement assembly 406 to cause the flanges 434 to be deflected inward. This in turn causes the concave surfaces 438 to engage the neck 9 of the bone anchor 7, thereby entrapping the head 8 within the receptacle 432. The proximal end 424 further includes a plurality of apertures 442 formed therein, the apertures configured to receive connectors 452 at the distal end 446 of the shaft 410. By way of example only, the receiver member 408 includes four apertures 442, however, any number may be provided without departing from the scope of the present invention.

Figure 71:
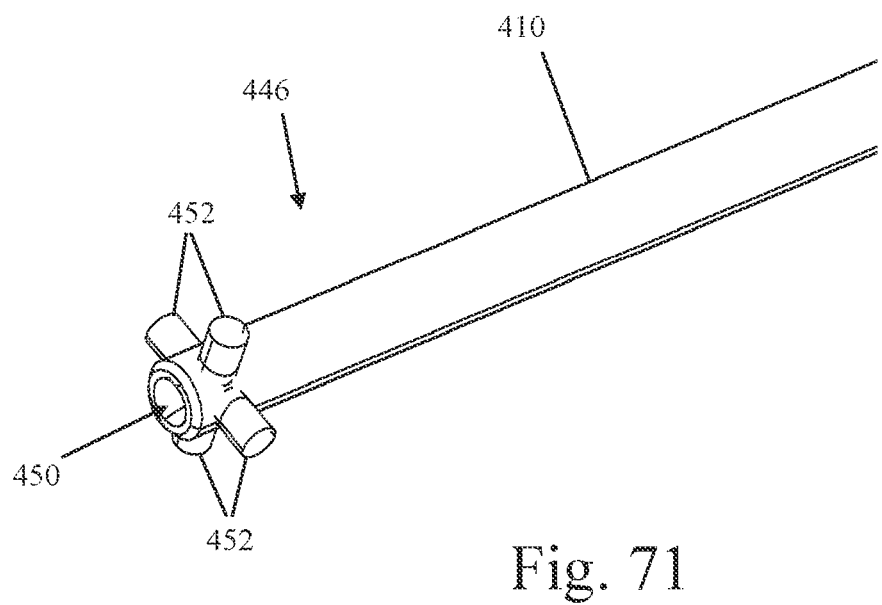
FIGS. 71 and 72 are perspective views of a distal end of a receiver assembly forming part of the inserter of FIG. 64.
Figure 72:
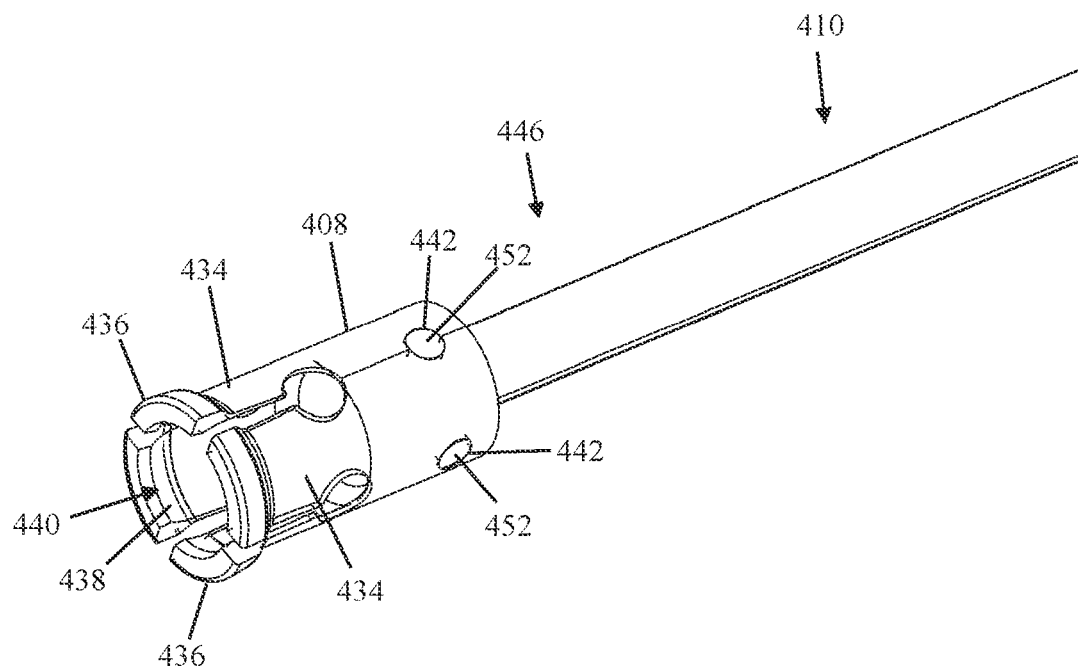

Referring to FIGS. 67, 71 and 72, the shaft 410 has a proximal end 444 and a distal end 446. The proximal end 444 includes a threaded region 448 configured to threadedly engage the thumbwheel 412, as will be described in further detail below. The shaft 410 is cannulated and therefore has a lumen 450 extending therethrough from the proximal end 444 to the distal end 446. The lumen 450 is dimensioned to receive a K-wire (not shown) or similar guidance tool to guide the inserter 400 to the surgical target site during a surgical procedure. The distal end 446 includes a plurality of connectors 452 dimensioned to be received within the apertures 442 on the receiver member 408. The connectors 452 snugly fit within the apertures 442 and are provided to prevent the receiver member 408 from rotating when the bone anchor 7 is being driven into bone.

The thumbwheel 412 has a lumen 454 extending axially therethrough and includes a pair of recesses 456 located on either end of the lumen 454 the recesses are each configured to receive a stopper 458 therein. The stoppers 458 are annular members that help hold the thumbwheel 412 in place and provide friction resistance to the thumbwheel 412 so that some force is required to turn the thumbwheel 412. The lumen 454 is threaded to interact with the threaded region 448 of the shaft 410. As will be explained below, the thumbwheel 412 is operable to cause the shaft 410 to translate proximally and distally, thereby causing the receiver member 408 to translate in and out of the distal aperture 494 of the engagement assembly 406, and further causing the receiver member 408 to lock or unlock a head of an anchor member 7 therein. The thumbwheel 412 is further provided with a suitable friction engagement element 460, for example ridges, recesses, bumps, adhesives, and the like, for enabling a user to grip and rotate the thumbwheel 412.

Figure 73:
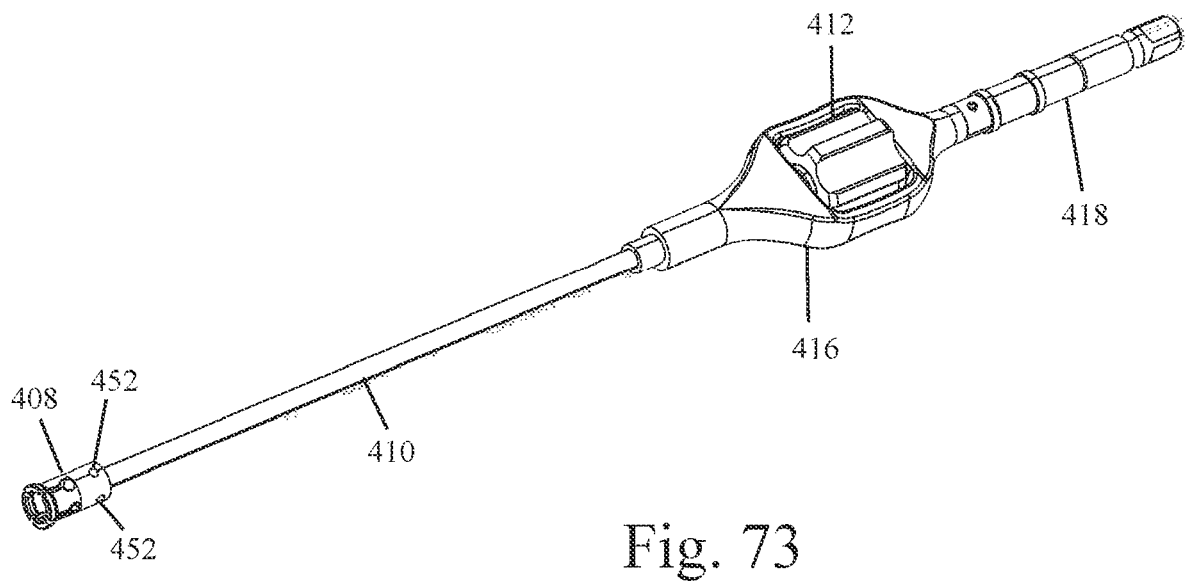
FIG. 73 is a perspective view of a receiver assembly forming part of the inserter of FIG. 64.

Referring to FIGS. 67 and 73, the housing 416 includes a proximal end 462, a distal end 464, and an aperture 466 positioned therein. The aperture 466 is dimensioned to receive the thumbwheel 412 and at least a portion of each of the stoppers 458. The housing 416 is cannulated, having a lumen 468 extending therethrough dimensioned to receive the shaft 410 therein. The proximal end 462 includes a post 470 dimensioned to engage the proximal attachment member 418. The distal end 464 includes a second post 472 dimensioned to engage the cannulated driver 414. The proximal engagement member 418 extends proximally from the housing 416 and is configured to engage an attachment (e.g. a T-handle) that enables the application of torque by a user in order to drive a bone anchor 7 into bone.

Figure 74:
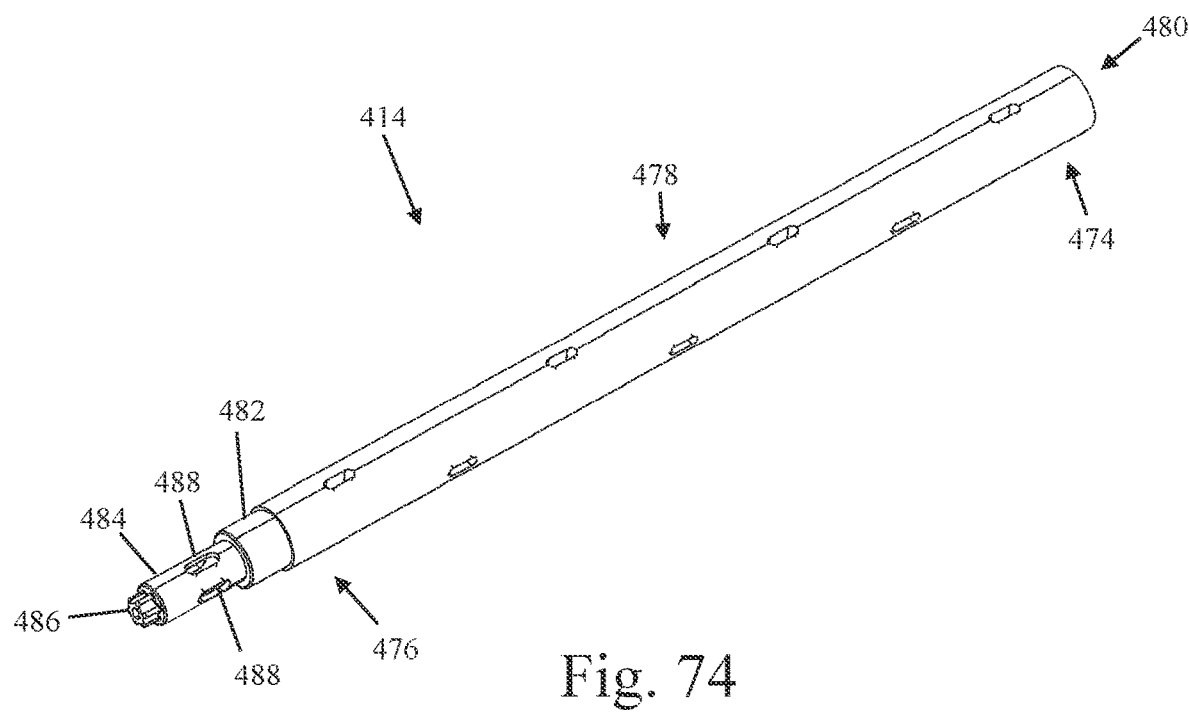
FIG. 74 is a perspective view of a driver member forming part of the inserter of FIG. 64.
Figure 75:
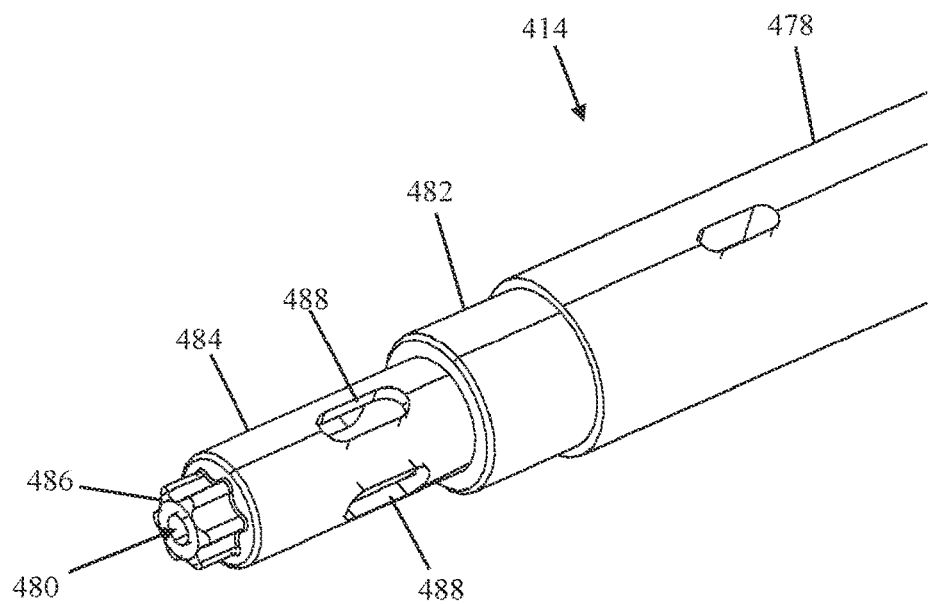
FIG. 75 is a perspective view of a distal end of the driver member of FIG. 74.
Figure 76:
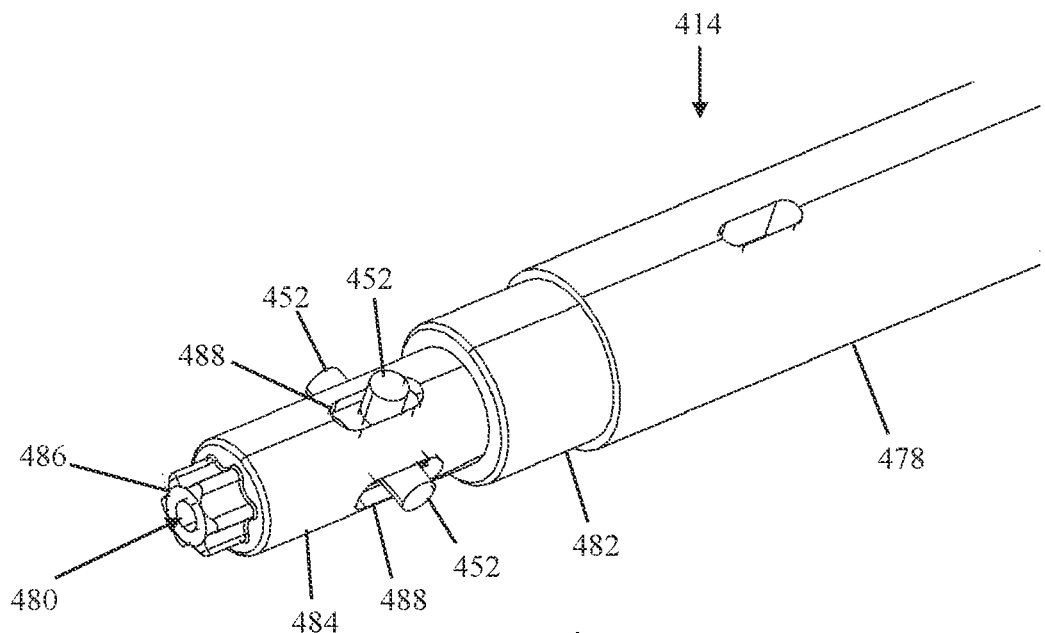
FIG. 76 is a perspective view of a distal end of the driver member of FIG. 74 coupled with the receiver assembly of FIG. 71.
Figure 77:
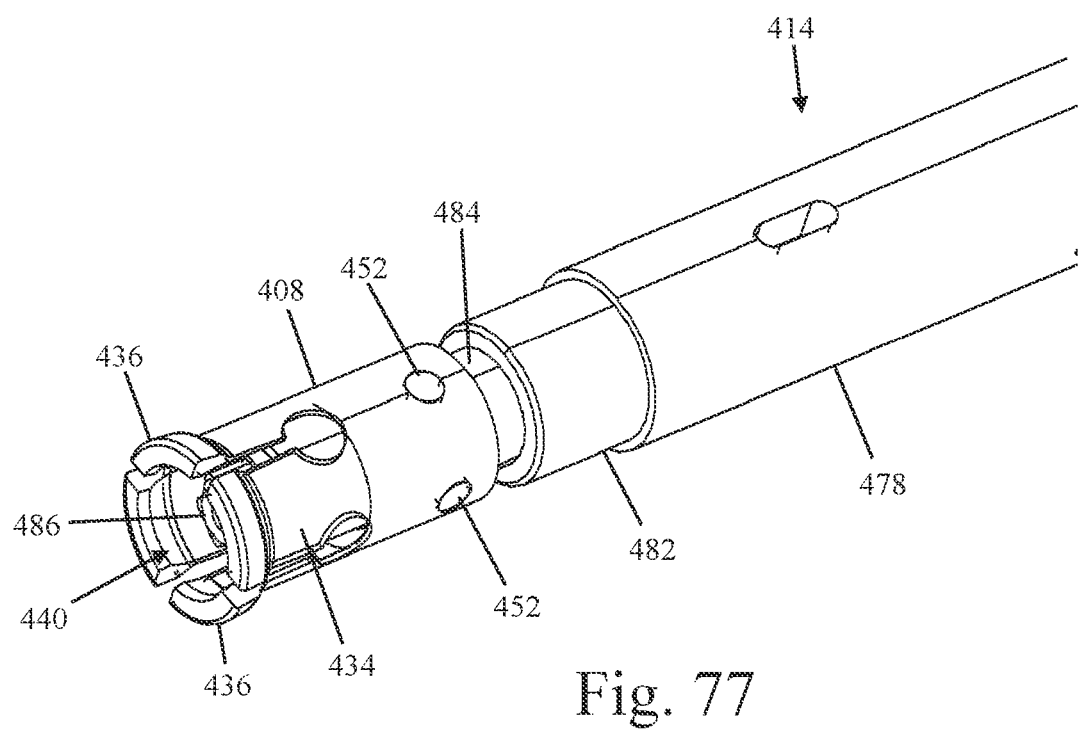
FIG. 77 is a perspective view of a distal end of the driver member of FIG. 74 coupled with the receiver assembly of FIG. 72.

Referring to FIGS. 74 and 75, the cannulated driver 414 includes a proximal end 474, a distal end 476, and an elongated cylindrical shaft 478 extending therebetween. The cannulated driver 414 further includes a lumen 480 extending axially therethrough, the lumen 480 configured to receive the shaft 410 of the receiver assembly 402. The distal end 476 includes a first cylinder 482 adjacent the shaft 478 and a second cylinder 484 extending distally from the first cylinder 482. The first cylinder 482 is configured to engage the blade engagement member 406. The second cylinder 484 has a diameter that is smaller than the diameter of the first cylinder 482, and is configured to be at least partially received within the lumen 430 of the receiver member 408. The second cylinder 484 includes a plurality of elongated slots 488 extending axially therethrough. The elongated slots 488 are provided in a number corresponding to the number of connectors 452 provided on the shaft 410. By way of example, the second cylinder 484 includes four elongated slots 488, however any number is possible. The elongated slots 488 each have width dimension corresponding to the diameter of the connectors 452. The connectors 452 are slidably engaged within the elongated slots 488, as illustrated by way of example in FIGS. 76 and 77. The length of the elongated slots 488 determine the degree of translation of the shaft 410, and thus the receiver member 408 that is allowed upon operation of the thumbwheel 412.

Figure 78:
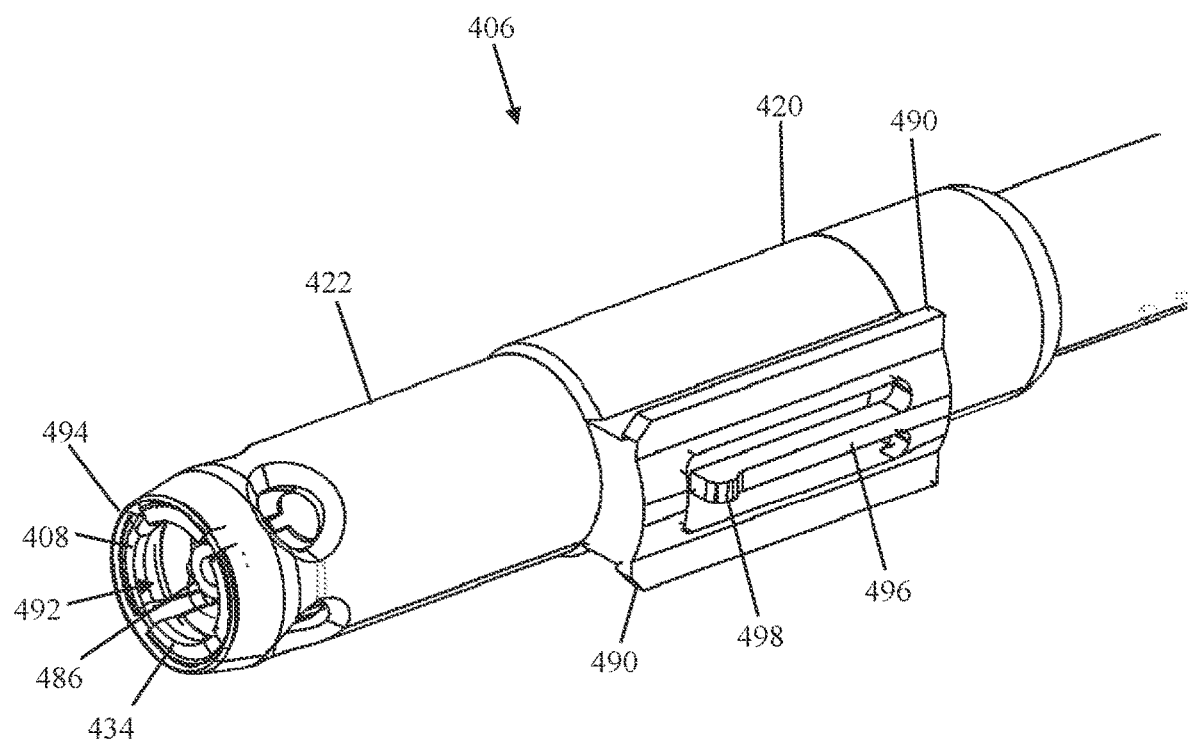
FIG. 78 is a perspective view of a blade engagement assembly forming part of the inserter of FIG. 64.
Figure 79:
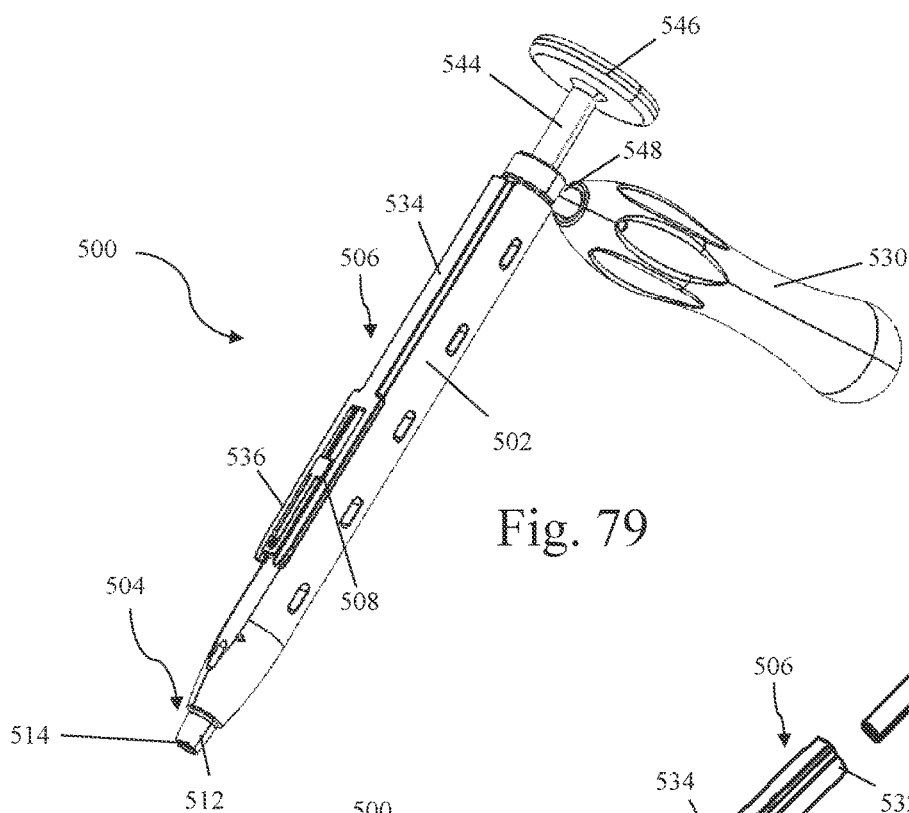
FIG. 79 is a perspective view of an example of a hoop shim reattachment tool according to one embodiment of the present invention.

Referring to FIG. 78, the engagement assembly 406 includes a blade engagement member 420 and a cylindrical body 422. The blade engagement member has a pair of elongated wings 490 that are configured to slidably engage the track grooves 252 of the first and/or second retractor blades 14, 16. The cylindrical body 422 includes a lumen 492 extending axially therethrough and a distal aperture 494. The lumen 492 is dimensioned to receive the receiver member 408 and cannulated driver 414 therein. The aperture 494 is dimensioned to allow passage of the receiver member 408 therethrough. The blade engagement member 420 further includes an axially oriented deflectable flange 496 extending thereon, the deflectable flange 496 including a knob 498 configured to be received within the recesses 250 in the retractor blade 14. When the knob 498 is positioned within a recess (or notch) 250, the flange 496 is in a relaxed position. As the inserter 400 is being advanced along the retractor blade 14, the knob 498 is forced out of the recess 250 and the flange 496 is deflected and under stress. When the knob 498 enters the next recess 250, the flange 496 snaps back into its initial position. This provides both a tactile and audible indication of the sequential advancement of the knob 498 along the series of recesses 250. In this manner, the user may be able to use the audible and tactile indications to determine how far the inserter 400 has been advanced along the retractor blade 14.

In use, preferably the hoop shim assembly 6, bone anchor 7, and retractor blade 14 are coupled together as described above, with the hoop shim assembly 6 in the locked position. The inserter 400 is provided in an initial position, with the distal end 426 of the receiver member 408 protruding from the distal aperture 494 of the engagement assembly 406. The inserter 400 is coupled to the retractor blade 14 via the engagement between the wings 490 of the engagement assembly 406 and the track grooves 252 of the retractor blade 14. Once coupled to the retractor blade 14, the inserter is slidably advanced along the retractor blade until the head 8 of the anchor member 7 is received within the receptacle 432 of the receiver member 408. The opening 440 is slightly smaller than the diameter of the head 8 of the anchor member 7, and thus there will be a tactile and/or audible indication as to when the anchor member 7 is received within the receiver member 408. Once this indication is relayed, the user then turns the thumbwheel 412 to lock the head 8 within the receiver member 408. Clockwise rotation of the thumbwheel 412 causes the shaft 410 (through the threaded engagement between the threaded region 448 of the shaft 410 and the threaded lumen 454 of the thumbwheel 412) to migrate proximally through the inserter 400. Due to the engagement between the connectors 452 and the receiver member 408, a proximal migration of the shaft 410 causes a proximal migration of the receiver member 408. This in turn draws the distal end 426 of the receiver member 408 through the distal aperture 494 of the engagement assembly 406. As this happens, the raised surface 436 interacts with the distal aperture 494 to cause the flanges 436 to be deflected radially inward. This causes the concave surfaces 438 to become engaged with the head 8 and/or neck 9 of the anchor member 7, thereby securely locking the anchor member 7 to the inserter 400. The assembly comprising the hoop shim assembly 6, anchor member 7, retractor blade 14, and inserter 400 is now ready for use.

To disengage the inserter 400 from the anchor member 7, the thumbwheel 412 is rotated in a counterclockwise direction. This rotation reverses the effects described above, and releases the inserter 400 from the anchor member 7. The inserter 400 may then be slidably removed from the retractor blade 14.

FIGS. 79-82 illustrate an example embodiment of a reattachment tool 500 for use with the tissue retraction system 10. The reattachment tool 500 may be used to simplify the act of reattaching a hoop shim 6 (and retractor blade 14, 16) to the head of an implanted bone anchor 7, in the event the hoop shim 6 becomes inadvertently or intentionally disengaged. For example, during the procedure the user may decide to swap out one or both of the retractor blades 14, 16 with longer or shorter blades. To do this, the user the user may disengage the hoop shim 6 from the bone anchor 7, with the hoop shim removal tool 350. The hoop shim 6 and retractor blade 14, 16 are removed from the operative corridor while the bone anchor 7 remains anchored. The new blade 14, 16 and hoop shim 6 are engaged, as described above, with the hoop shim 6 in the unlocked position. The reattachment tool 500 is then engaged with the retractor blade 14, 16 above the hoop shim 6 and the blade, hoop shim, and reattachment tool are advanced towards the bone anchor 7. The hoop member is then attached over the bone anchor 7 and the hoop shim is locked.

Figure 80:
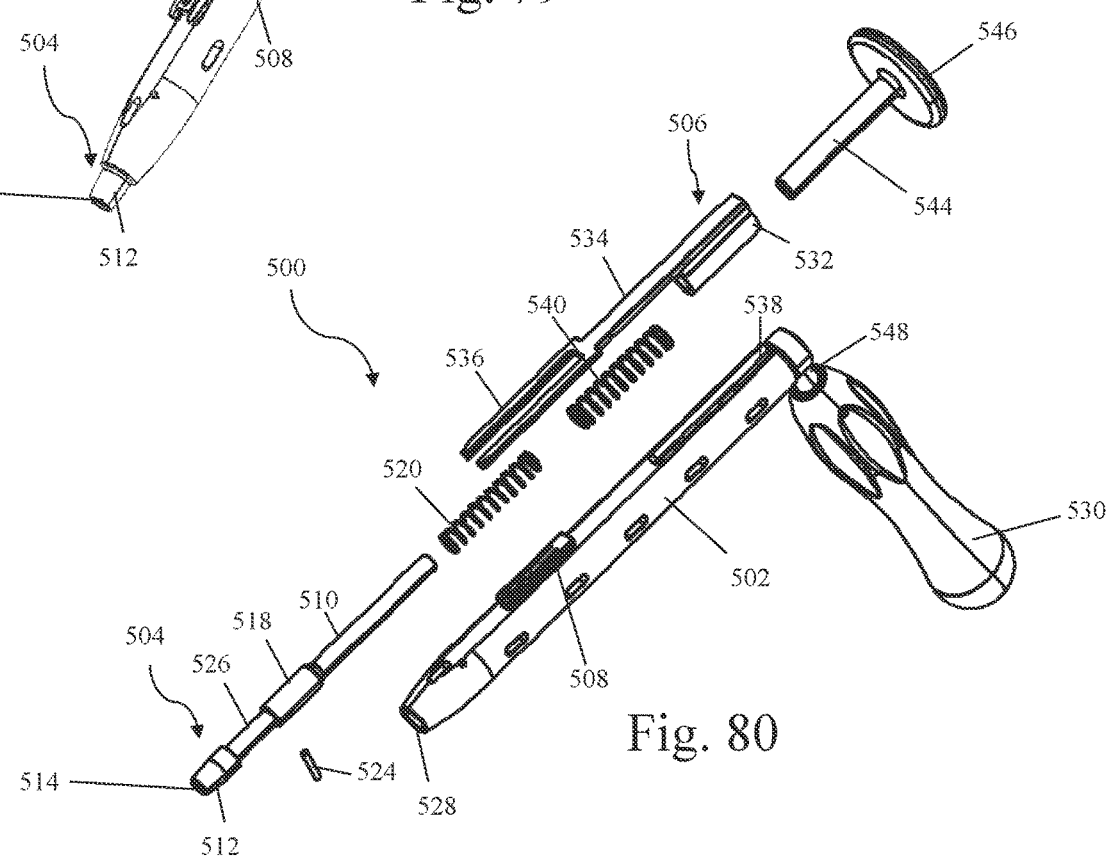
FIG. 80 is an exploded perspective vie w of the hoop shim reattachment tool of FIG. 79.
Figure 81:
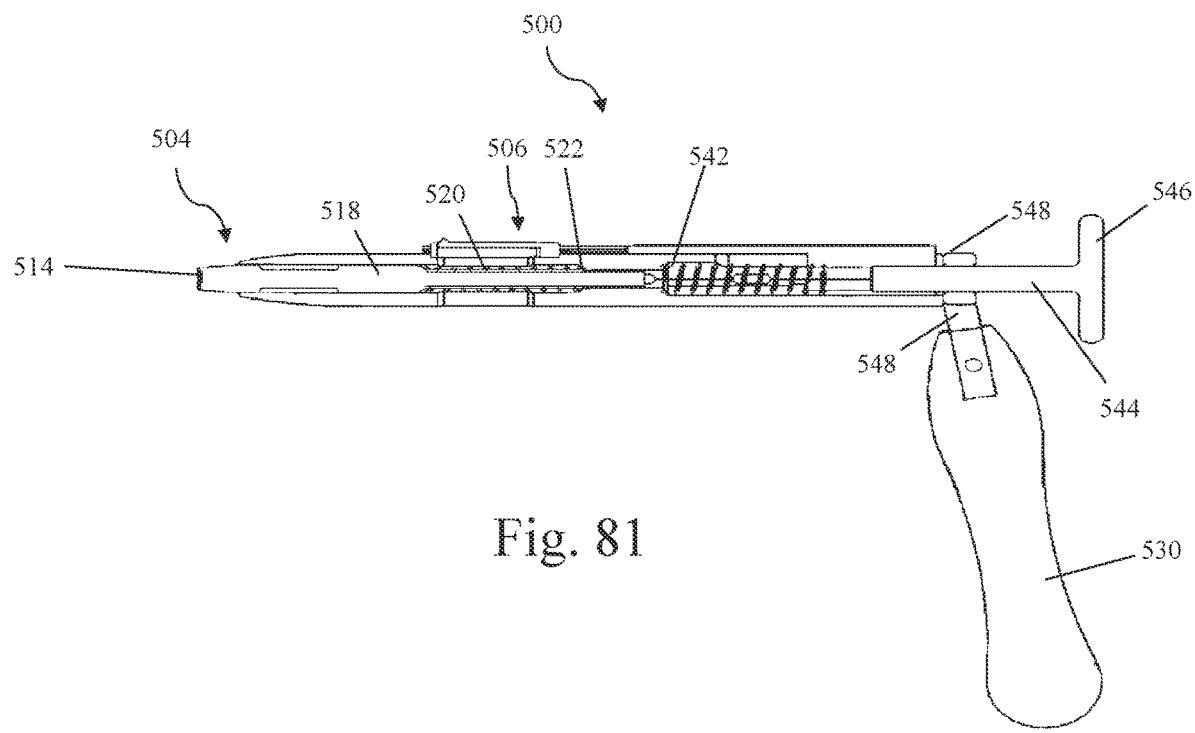
FIG. 81 is a side cross-section view of the hoop shim reattachment tool of FIG. 79.
Figure 82:
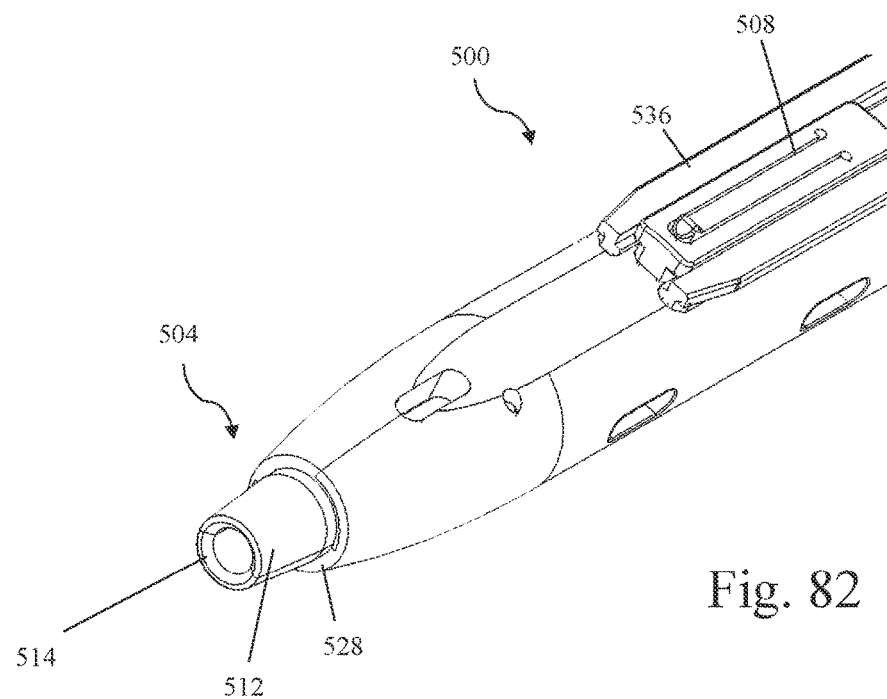
FIG. 82 is an enlarged perspective view of the distal end region of the hoop shim reattachment tool of FIG. 79.

The reattachment tool 500 includes an outer body 502, an anchor engaging member 504, a shim engaging member 506, and a blade engaging member 508. With reference to FIGS. 80-81, the anchor engaging member 502 includes a shaft 510 terminating in a distal head 512 with a spherical pocket 514. The anchor engaging member is spring loaded in a distal cavity 516 of the body 502. The shaft 510 has a neck region 518 with a diameter that is larger than the rest of the shaft 510. A spring 520 encircling the shaft 510 is captured between the neck 516 and aback wall 522 of the cavity 516. A pin 526 traversing through cavity 516 prevents passage of the neck 518, keeping the anchor engagement member 504 fixed in the body 502. A cutout 526 between the distal head 512 and the neck 518 permits the anchor engaging member to slide along the pin 524 between a neutral position wherein the distal head 512 extends out of the body 502 and a depressed position wherein the distal head 512 is fully received within the body 512. With the anchor engaging member 504 contacting the head 8 of bone anchor 7, downward pressure is applied to the body 502 causing the distal head 512 of the anchor engaging member 504 to retract into the body 502 as the body 502 advanced towards the anchor site. The opening 528 at the distal end of the body 502 is large enough to receive the head 8 therein. As the head 8 is received into the body 502, the distal end presses the hoop member 304 over the head 8, such that the hoop shim 6 and bone anchor 7 are engaged in the unlocked position. The spherical pocket 514 of the distal head 512 complements the head 8 of the bone anchor 7 to help maintain engagement and alignment of the distal head 512 and anchor head 8. A handle 530 is preferably included to facilitate use of the reattachment tool.

The shim engaging element 506 has a base 532 and an arm 534 ending in a pair of fingers 536. The base 532 is spring loaded in a proximal cavity 536 of the body 502. The arm 534 and fingers 536 extend along the outside of body 502. Slot 538 in body 502 allows the base 532 and arm 534 to travel along the body 532. A spring 540 is captured between a front wall 542 of the proximal cavity 536 and the base 532 and holds the shim engaging element 506 in a neutral position. Fingers 536 slidably engage the track grooves 252 of the retractor blade 14, 16 and rest above the top of the shim element 302 of the hoop shim 6 when in the neutral position. Pusher 544 connects to the base 532 through a proximal end 548 of the body 502 and is used to advance the shim engaging element 506 distally towards the hoop shim 6. After reengaging the hoop member 304 over the anchor head 8, and with the distal end of the body still pressed against the hoop member 304 at the anchor site (and thus with the anchor head 8 still captured within the body 502), the pusher is used to apply downward force to the shim element 302, via the fingers 536, to move the hoop shim into the locked configuration. The pusher 544 preferably includes an enlarged end 546 for easier use.

The blade engagement member 508 extends from the body 502 and includes a deflectable flange 550 extending thereon. The deflectable flange 550 includes a knob 552 configured to be received within the recesses 250 in the retractor blade 14, 16. When the knob 552 is reattachment tool 500 is being advanced along the retractor blade 14, 16, the knob 552 is forced out of the recess 250 and the flange 550 is deflected and under stress. When the knob 552 enters the next recess 250, the flange 550 snaps back into its initial position. This provides both a tactile and audible indication of the sequential advancement of the knob 552 along the series of recesses 250, as well as a secure (but releasable) engagement to the retractor blade 14, 16. The fingers 536 of the shim engaging element are situated on either side of the blade engaging element 508 and slidably engage the track grooves.

Figure 83:
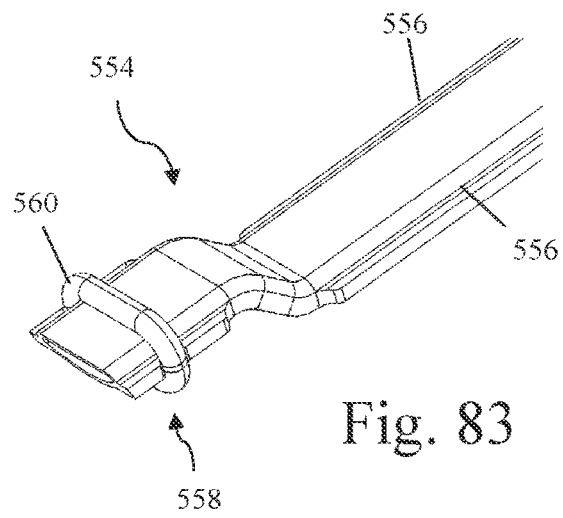
FIG. 83 is a perspective view of the distal end of a light cable, according to one example embodiment of the present invention.
Figure 84:
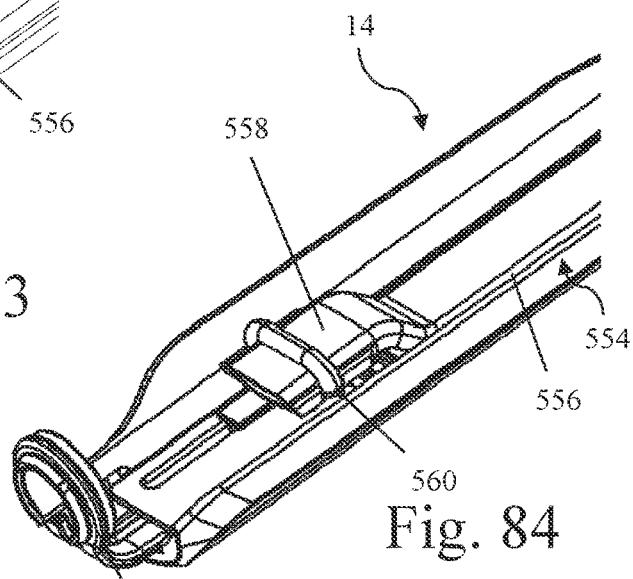
FIG. 84 is a perspective view of the distal end of the light cable of FIG. 83 engaged to the retractor blade of FIG. 22 and extending over the proximal end of the hoop shim of FIG. 31.
Figure 85:
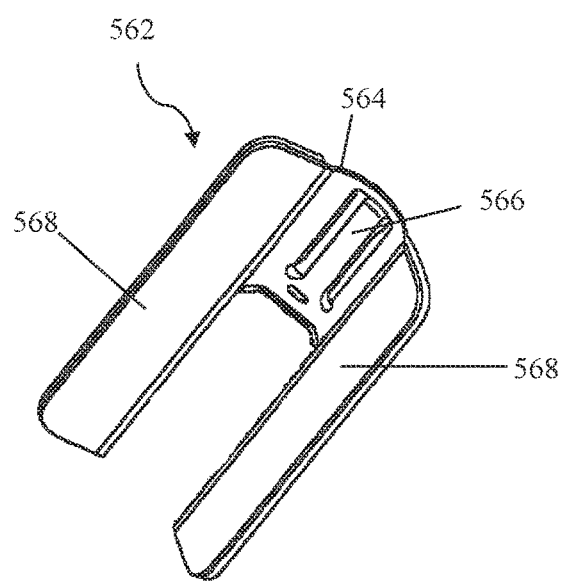
FIG. 85 is a perspective view of a tissue shim according to one example embodiment of the present invention.
Figure 86:
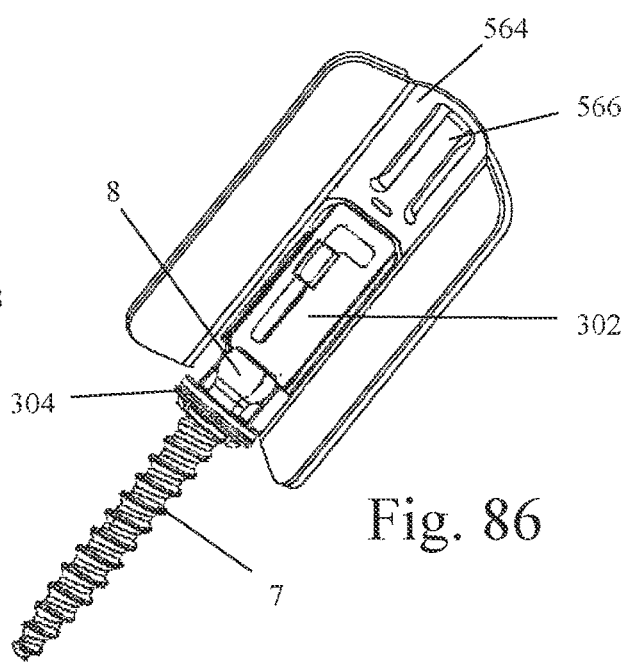
FIG. 86 is a perspective view of the tissue shim of FIG. 86 illustrating the manner in which the shim element of the hoop shim nestles between wings of the tissue shim.

Turing to FIGS. 83-86, the surgical fixation system described herein may be provided with a number of additional features or accessories. For example, as depicted in FIG. 83, a light cable 554 capable of coupling to the retractor blade assemblies and illuminating the operative corridor without obstructing the surgeon's view may be provided. The light cable 554 has an offset distal end 556 and wing extensions 558 beginning proximally to the offset distal end. In this configuration the distal end 556 can slide over the shim element 302 when the light cable is advanced down the track grooves 252, as shown in FIG. 84. By extending the distal end 556 over the shim element 302 of the hoop shim, glare that might occur from light reflecting off of the shim element 302 is negated. An o-ring 560 disposed around the distal end 558 engages the slot 340 of the shim element 302 to secure the light cable 554 from unwanted movement. The light cable may be bendable but also capable of holding its bended such that the proximal portions can be bended out of the way after exiting the retractor blade.

By way of further example, tissue shims 562 are capable of coupling to the retractor blade assemblies to extend the width of the retractor blades. The tissue shims 562 include a blade engaging portion 564. The blade engaging portion includes wing extensions (not shown) that slidably engage the track grooves 252 of the retractor blade 14, 16. A deflectable tab 566 similar those previously described engages the notches 250 on the interior face of the retractor blades 14, 16 to secure the position of the tissue shim 562 along the retractor blade. Branches 568 extend outward and downward from the blade engaging portion 564, such that when the blade engaging portion 564 is slidably received down the track grooves 252 of the retractor blade 14, 16, the branches 568 extend down to the target site, or nearly so, while the blade engaging portion remains above the shim element 302 of the hoop shim 6. The light cable 554 may be inserted above the tissue shim 562.

Still by way of further example, though not shown, a fourth blade attachment may be provided that independently places a fourth retractor blade within the operative corridor opposite the medial retractor blade. The fourth retractor blade assembly may be attached to retractor body, medial blade assembly, or either of the first or second (or both) retractor blade assemblies. The fourth retractor blade may be attached to the retractor body so as to allow multi axial movement or polyaxial movement. The fourth retractor blade may be used to expand the operative corridor laterally to expose the transverse processes. The fourth retractor blade may be similar to the third retractor blade 18 described above. The blade extension of the fourth retractor blade may be free floating as described for retractor blade 18 or it may be fixed. In either case, it is intended that the distal end of the forth retractor blade may elevate tissue off of the bone as it is extend or swept laterally. Exposing the transverse processes in this manner may provide the ability to increase fusion of the adjacent vertebrae by fusing the transverse processes together.

According to yet still another example, a malleable wall barrier may be provided that can be inserted between the retractor blades and the surrounding soft tissue to help keep the soft tissue out of the operative corridor and surgical target site. This malleable barrier may be semi-rigid in that it can be formed to conform to a desired shape yet hold this shape under pressure from the surrounding tissue. It is contemplated that this malleable barrier be supported by the retractor blades, but not necessarily attached to them. The malleable barrier may also extend out of the operative corridor (out of the patient) and be capable of being "folded" to lie on the patient's skin so as to be out of the surgeon's way.

While the retractor system 10 and methods described above have been directed towards single level fusion, it is possible to perform multiple level fusions using the retractor system 10. This may be accomplished in a number of different fashions. For example, the steps described above can be completed in the same fashion expect that the blade-shim-anchor assemblies are implanted in the pedicles of the vertebra at either end of the multi level spinal segment such that the operative corridor simply spans the entire segment. Alternatively, the operative corridor may be adjusted to expose each level of the multi level fusion sequentially. In this case, a third blade-shim-anchor assembly is advanced and anchored into the pedicle of the additional vertebra. For efficiency, this step may be performed at the same time the blade-shim-anchor assemblies are anchored to the first and second pedicles or it may be performed once the user is ready to begin work on the additional level(s). The hoop shim 6 is disengaged from the bone anchor 7 at the middle vertebrae of the segment and the retractor blade 14 or 16 is removed and replaced with a retractor blade 16 or 14, respectively, that faces the opposite direction (and the added third retractor blade). In one example this may be accomplished using the reattachment tool 500 as described above. According to another example, an alternate retractor blade 600 may be provided to facilitate swapping of the left and right facing blade at the middle level.

Figure 87:
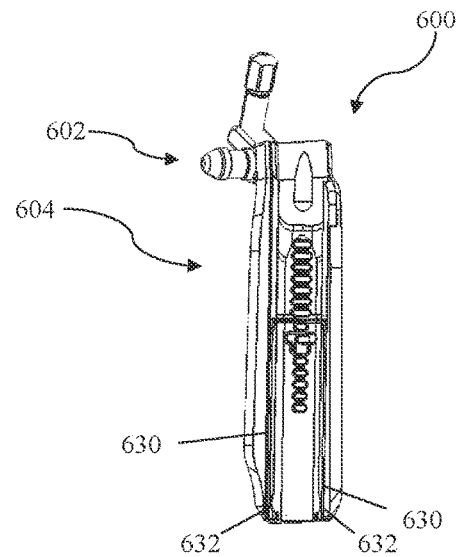
FIG. 87 is a front view of an alternate retractor blade for use with the surgical fixation system of FIG. 1, according to one example embodiment.

FIG. 87 illustrates an alternate retractor blade 600 that may be used with the retractor assembly 10 to facilitate multilevel procedures. The retractor blade 600 is similar to blade 14, 16 described above and includes an attachment portion 602 and a blade portion 604. The attachment portion 602 is generally identical to the attachment portion 220 of retractor blade 14, 16, such that repeat discussion is unnecessary.

Figure 88:
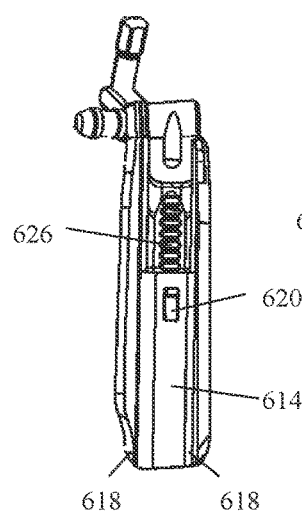
FIG. 88 is a front view of the retractor blade of FIG. 87 with a track insert removed.
Figure 89:
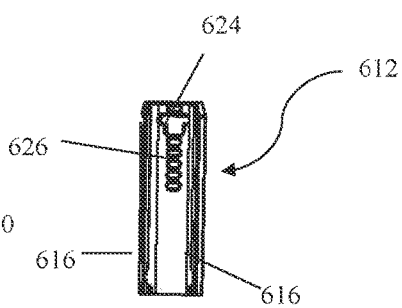
FIG. 89 is a front view of a track insert forming part of the retractor blade of FIG. 87.
Figure 90:
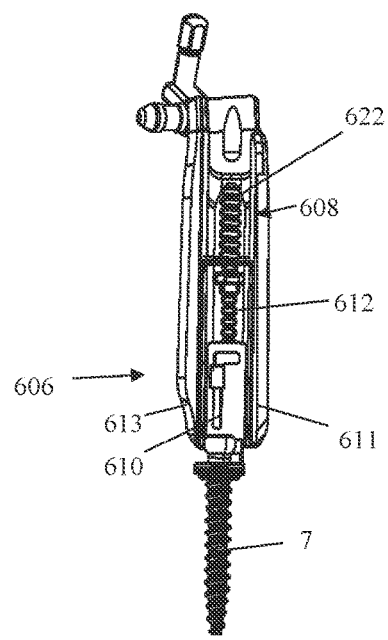
FIG. 90 is a front view of the retractor blade of FIG. 87 with the hoop shim of FIG. 31 engaged.

The blade portion 604 is also similar to the blade portion 222 of retractor blade 14, 16 in that it extends distally from the attachment portion 602 and includes an outside surface 606, an inside surface 608, a first lip 610, and a second lip 611. The first lip 610 and second lip 611 comprise edges of the blade portion 604 and each extend along the length of the blade portion from the attachment portion 602 to the distal end of the blade portion 604. The first and second lips 610, 611 are asymmetric relative to one another. For example, the first lip 610 has a concave portion 613 that allows for clearance of spinal anatomy during blade angulation. The outside surface is a smooth arcuate surface configured to interact with the patient's soft tissue near the operative corridor. The outside surface 606 extends from the attachment portion 602 at a non-orthogonal angle relative to the top surface of the attachment portion. Since much of the blade has a generally uniform thickness, the inside surface 608 extends from the attachment portion 602 at the same non-orthogonal angle relative to the top surface. Thus, the effect is that the operative corridor is immediately established having a conical shape with no further adjustment of the tissue retraction assembly 10 required. Additionally, the blade portion extends from the attachment portion 602 such that the blade face is oriented orthogonal to the attachment portion 602. Thus, when the retractor blade 600 is attached to the retractor body 10, the inside surface 608 faces the operative corridor at an angle, for example between 20 and 60 degrees). This orientation of the blade portion relative to the attachment portion helps optimize the shape of the operative corridor.

Where the retractor blade 600 differs from the retractor blade 14, 16, is in that the inside surface 608 is not formed of a single surface, but rather it includes a track insert 612. As best viewed in FIG. 88, inner surface 608 has recess 614 which slidably receives the track insert 612 from the bottom of the blade portion. Edges 616 of the track insert 612 slide into grooves 618 formed in the sides of the recess 614. A deflectable tab 620 extends into the recess 614 pointing upward. As the track insert 612 advances into the recess 614 it deflects the tab 620 allowing the insert 612 to pass. When the track insert 612 is fully inserted into the recess 614 it abuts an upper portion 622 such that the track insert 612 and upper portion form a generally flush inner face. Together, the upper portion 622 and track insert 612 also define track grooves 630 that slidably receive the shim element 302 (as well as the inserter 400, reattachment tool 500, light cable 554, tissue shim 562, and guide 650, for example). The deflectable tab 620 aligns with a horizontal aperture 624 near the top of the track insert 612 when the track insert is fully inserted and the tab 20 returns to a natural position, catching the horizontal aperture like a hook such that the track insert cannot disengage from the recess 614. The track insert includes stops 632 that prevent the hoop shim 6 from disengaging from the bottom. The upper portion 622 and the track insert 612 both include notches 626 that function like the notches 252 described above.

Figure 91:
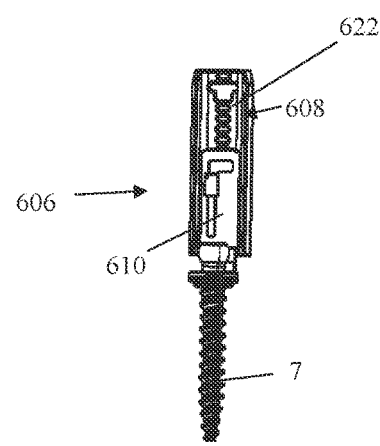
FIG. 91 is a front view of the track insert of FIG. 90 with the hoop shim engaged and the remainder of retractor blade removed.
Figure 92:
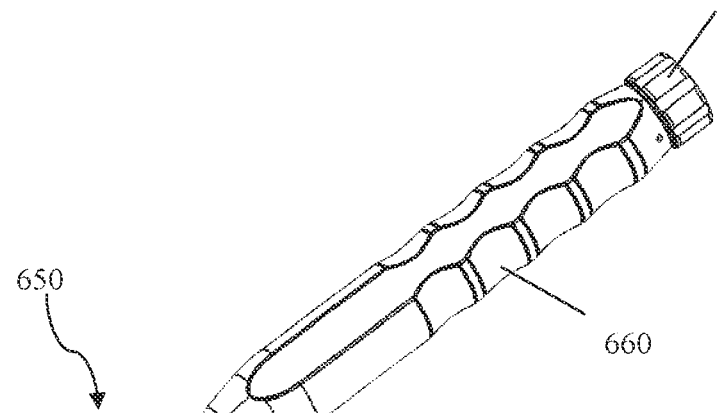
FIG. 92 is a perspective view of a guide instrument for use with the retractor blade of FIG. 87, according to one example embodiment.
Figure 93:
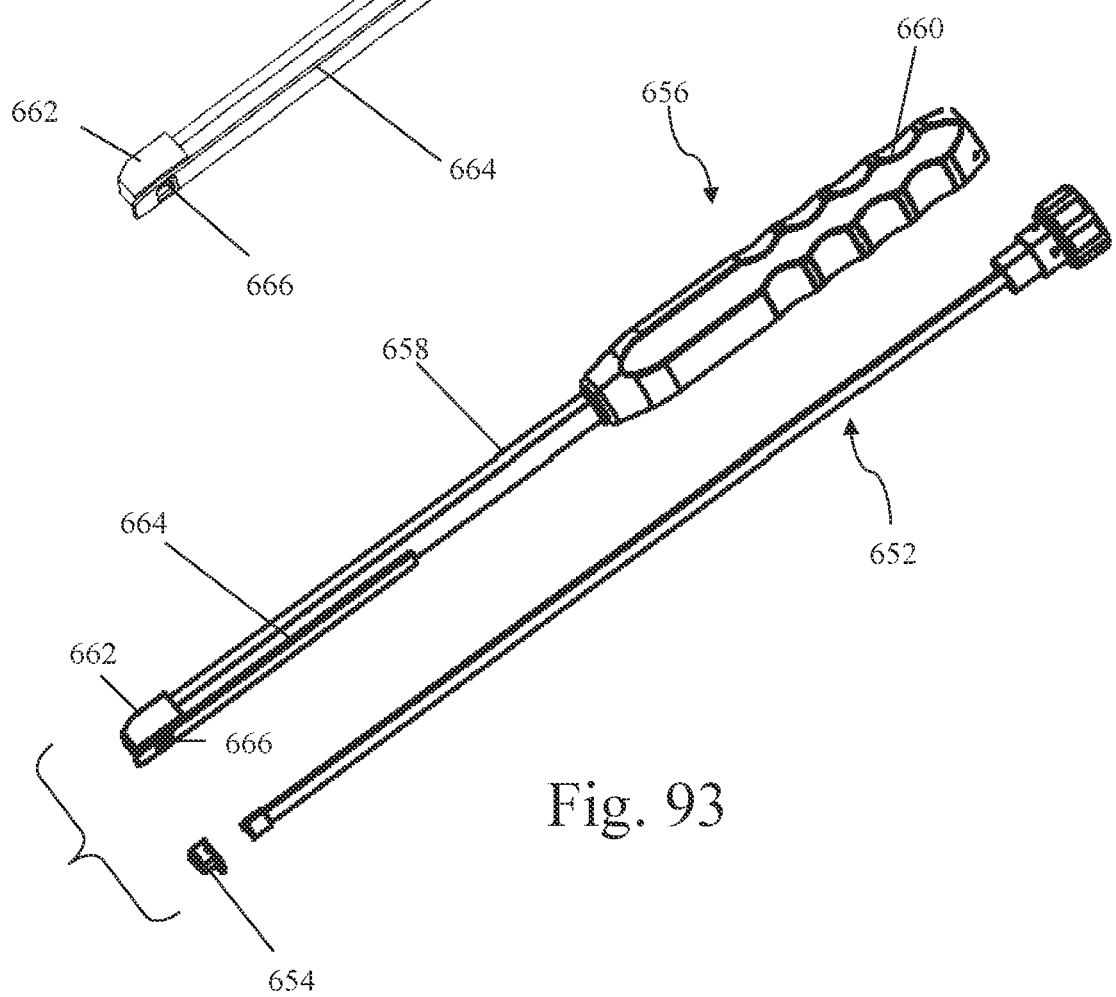
FIG. 93 is an exploded perspective view of the guide instrument of FIG. 92
Figure 94:
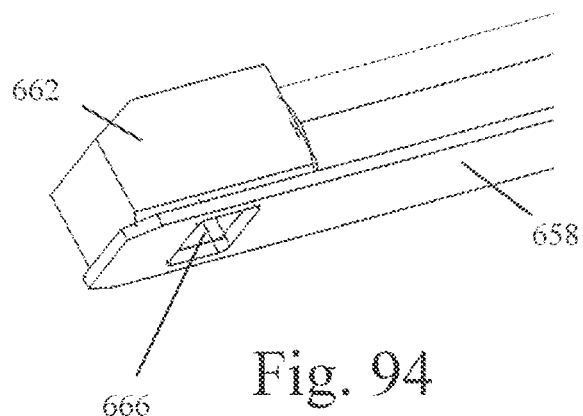
FIG. 94 is a perspective view of the distal end of the body portion of the guide instrument of FIG. 92.
Figures 95, 96:
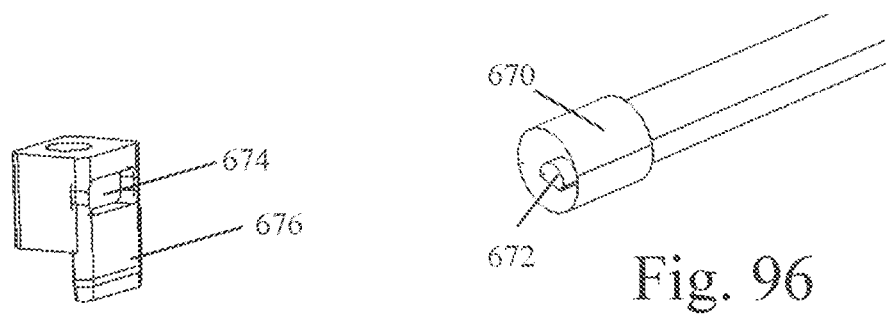
FIG. 95 is a perspective view of an actuator of the guide instrument of FIG. 92.
FIG. 96 is a perspective view of the distal end of a driver of the guide instrument of FIG. 92.
Figures 97, 98:
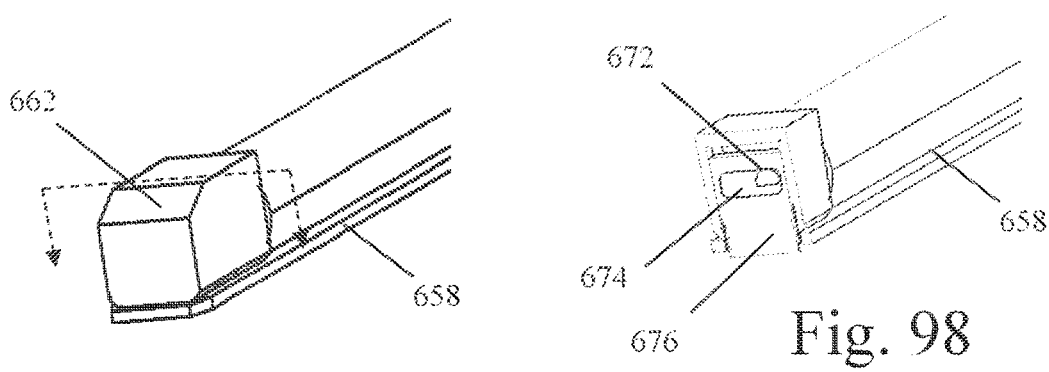
FIG. 97 is a perspective view of the housing forming part of the body portion of FIG. 94.
FIG. 98 is a cross section view of the housing of FIG. 97 showing the actuator of FIG. 95 and the driver of FIG. 98 interacting therein.
Figure 99:
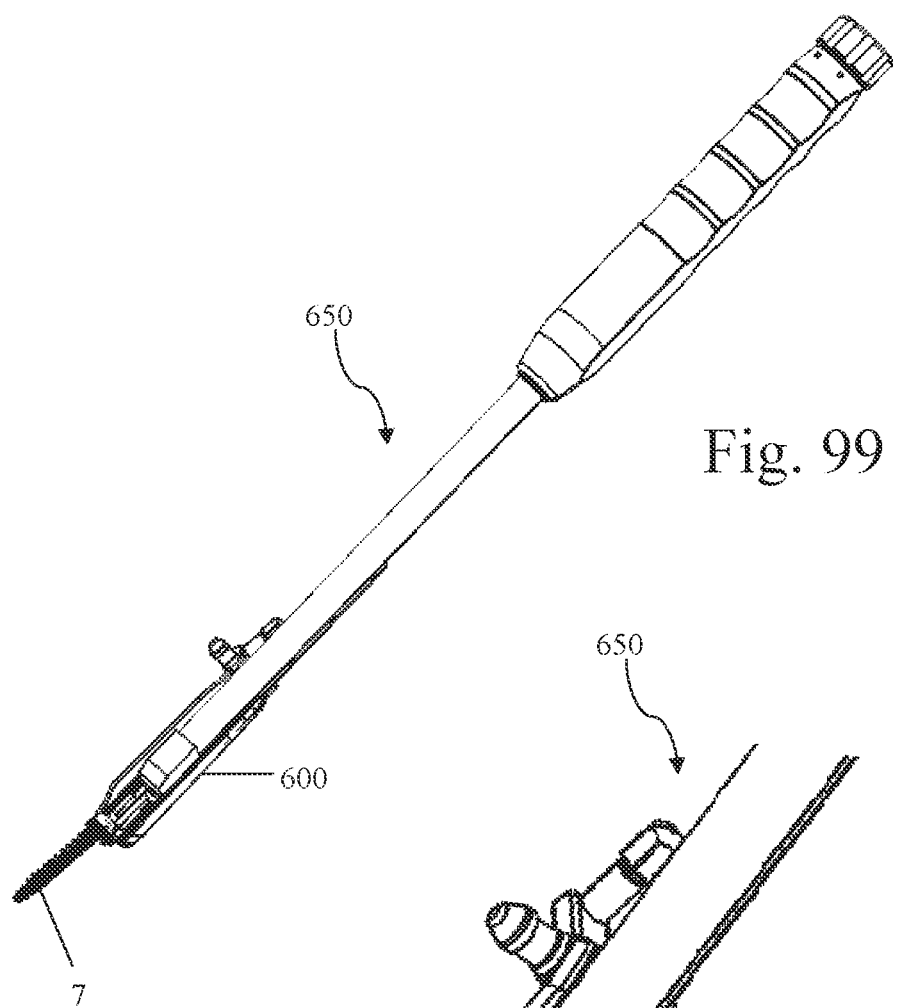
FIG. 99 is a perspective view of the guide instrument of FIG. 92 engaged to the retractor blade and track insert of FIG. 87.
Figure 100:
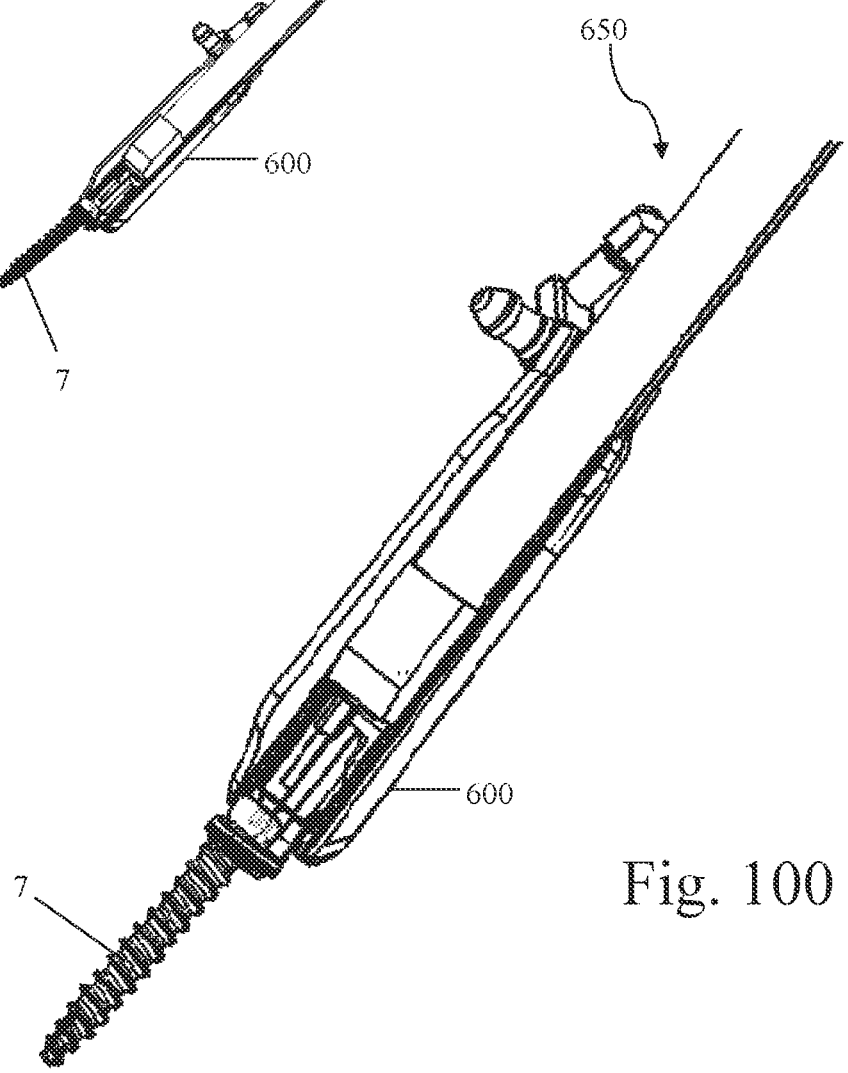
FIG. 100 is an enlarged view of the distal end of the guide instrument of FIG. 92 engaged to the retractor blade and track insert of FIG. 87.

Initially, the hoop shim 6 and bone anchor 7 may be engaged to the retractor blade 600, coupled to the inserter 400, and implanted into the appropriate pedicle as described above for blade 14, 16. To replace the blade 600 with an opposite facing blade 600'(or to simply change blades for a longer or shorter blade), rather than removing the hoop shim 6 and reattaching the hoop shim together with a new blade, as described above, the hoop shim 6 and track insert 612 remain attached to the bone anchor 7 (as in FIG. 91) and a new retractor blade 600' (having the desired new orientation or size) slides onto the track insert 612.

With reference to FIGS. 92-100, a guide instrument 650 according to an example embodiment is pictured. The Guide instrument functions to both disengage the track insert 612 from the deflectable tab 620 and to guide the new blade onto the track insert 612. The guide 650 includes a driver 652, an actuator 654, and a body 656. The body 656 has a generally tubular outer shaft 658 fitted with a handle 660 at the proximal end and a housing 662 at the distal end. The underside of the outer shaft 658 includes an engagement plate 664 that slidably engages the track grooves 630 of the blade portion 604. The housing 662 holds the actuator 655 and has an opening 666 through the engagement plate 664. The driver 652 has a knob 668 to facilitate rotation of the driver. The distal end 670 of the driver includes a projection 672. By way of example, the projection shown has a generally half circle shape. The projection 672 is offset from the center of the distal end 670 such that rotation of the driver 652 causes the height of the projection 672 to change as it travels the circumference. The projection 672 extends into housing 662 and rests in slot 674 of the actuator 654. As projection 672 travels along the circumference of the distal end 670, it drives the actuator 654 up or down. When the actuator is forced to the bottom of the housing 662, that is when the actuator is in a locked position, a horizontal extension 676 extends through the opening 666. When fully engaged with the retractor blade 600, the horizontal extension 676 aligns with the horizontal aperture 624 of the track insert. The horizontal extension 676 passes through the horizontal aperture 624, deflecting the tab 620 inward and releasing the track insert 612 from the rest of retractor blade 600. The blade 600 can then be removed by sliding the blade along the engagement plate 664. The guide 650 remains in place and the replacement retractor blade 600' slides down the engagement plate 664 onto the track insert 612. Rotating the driver to the unlocked position draws the horizontal extension 676 into the housing 662 and the deflectable tab 620 replaces the horizontal extension in the horizontal aperture.

Figure 101:
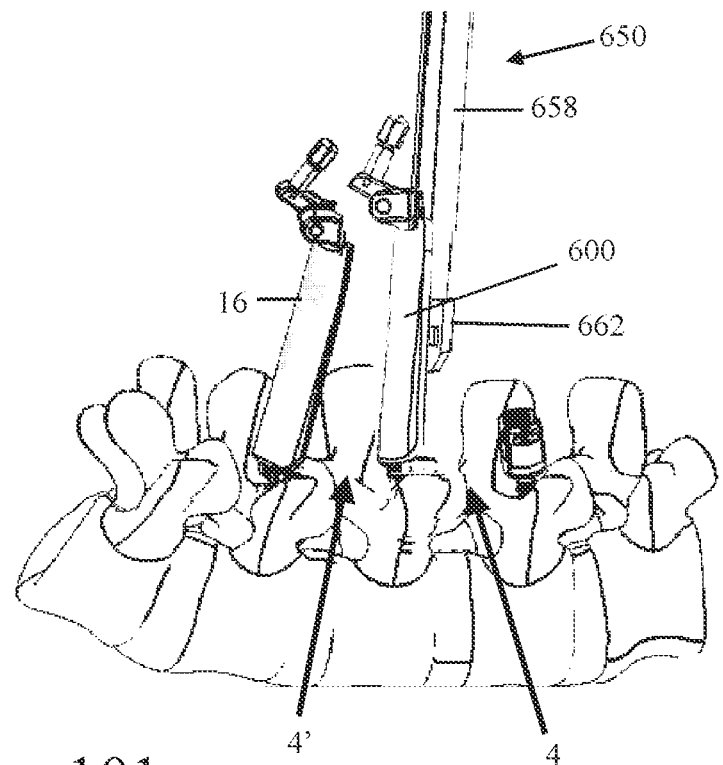
FIG. 101-108 are perspective view of the spinal fixation system of FIG. 1 including the retractor blade of FIG. 87 in use during various steps of a multi-level spinal fusion procedure.
Figure 102:
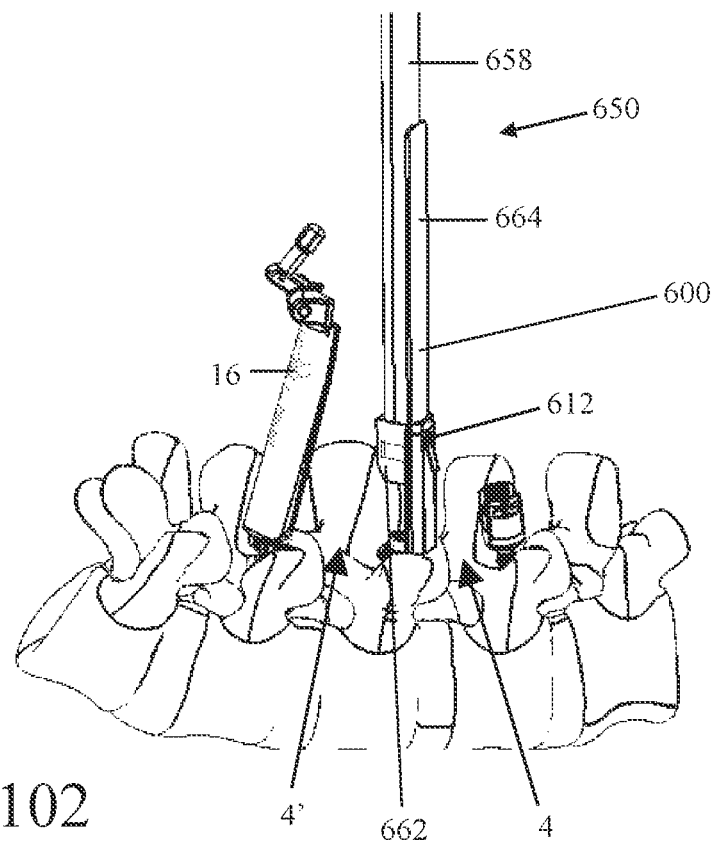
Figure 103:
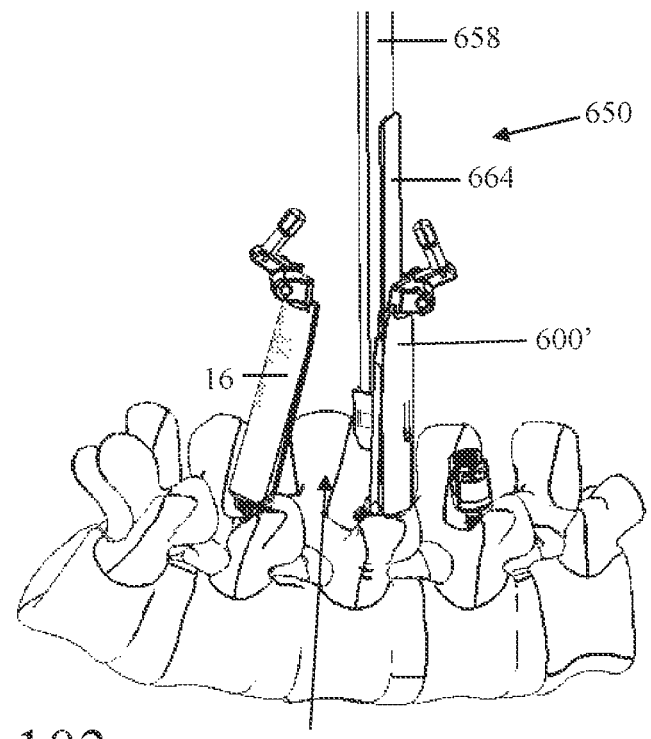

With reference now to FIGS. 101-108, the surgical retraction system 10 is demonstrated in use for performing a multi level TLIF procedure. By way of example, the multi level procedure begins the same way as the single level procedure described above (except that the anchor-shim-blade combination for the third vertebra may be placed at the same time as the others) and with reference to FIGS. 47-57. This description of the multi level procedure picks up after the user has completed work at the first level (e.g. performed a discectomy and implanted a fusion implant), but before the spinal rod is inserted connecting the anchors 7 (FIG. 51). The hoop shim 6 is removed from the outer vertebra of the completed level, a bone anchor receiver is attached to anchor 7, and the corresponding retractor blade 16 is removed. The guide instrument 650 is advanced down the track grooves of the middle blade (i.e. the retractor blade positioned over the center vertebra of the multi level segment) (FIG. 101). When fully seated, the guide 650 is actuated to engage the horizontal extension 676 into the horizontal aperture 624 to disengage the tab 620. With the tab 620 disengaged, the retractor blade 600 is removed leaving the track insert 612 and guide 650 attached to anchor 7 via the hoop shim 6 (FIG. 102).

The new retractor blade 600' is slidably engaged to the guide 650 and advanced into the operative corridor along the engagement plate 664 of the guide. When the retractor blade recess 614 of blade 600' has fully received the track insert 612, the guide 650 is actuated to release the deflectable tab 620, locking the track insert 612 to the new blade 600'. The guide 650 is then removed.

Figure 104:
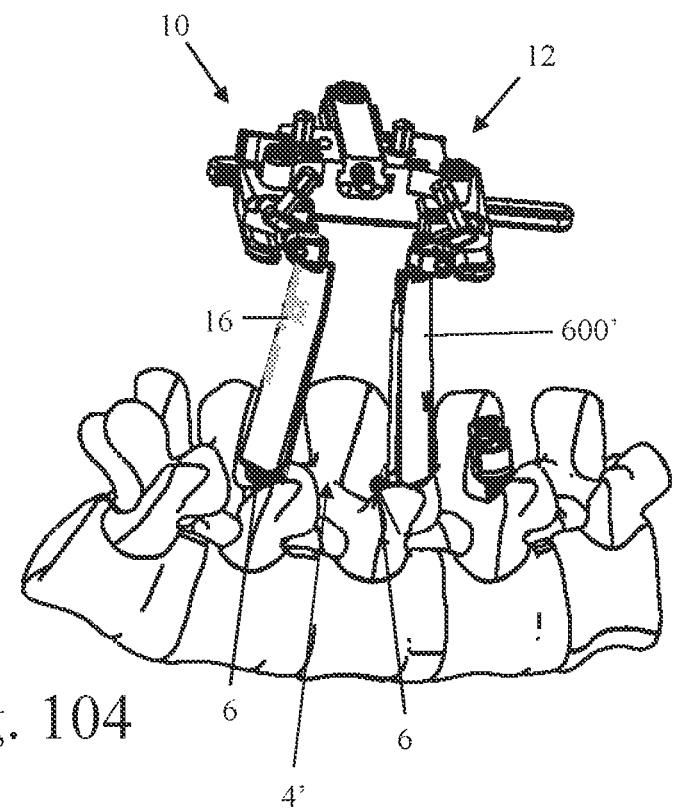
Figure 105:
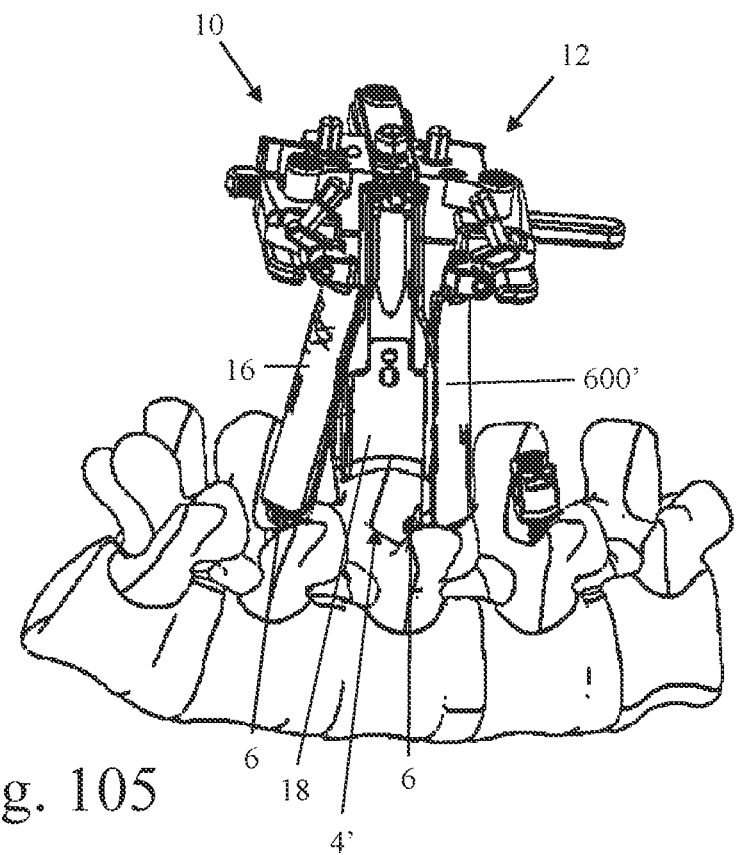
Figure 106:
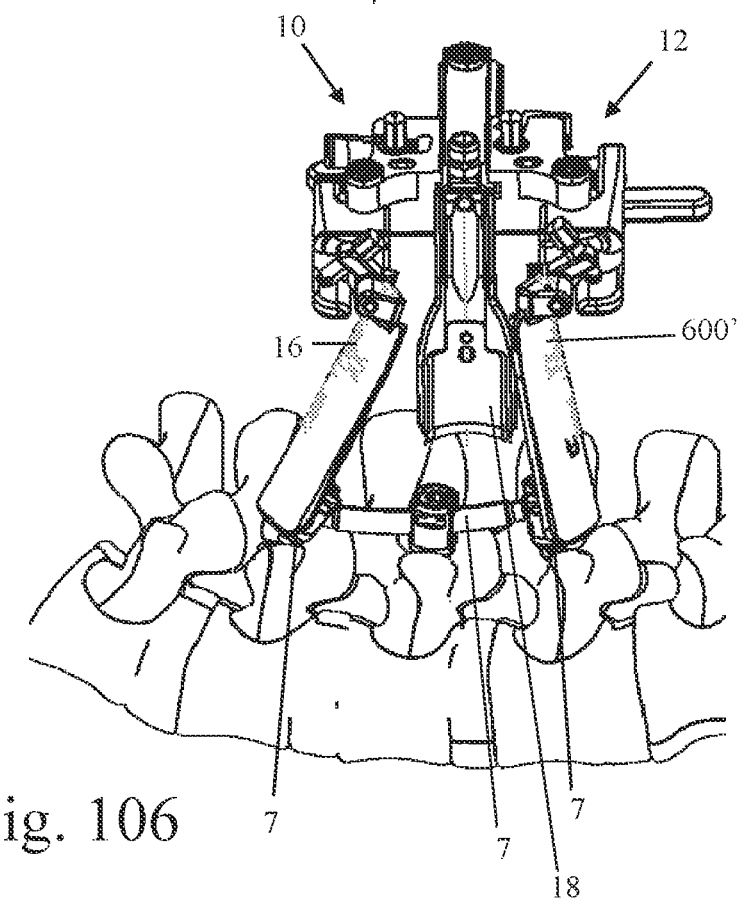
Figure 107:
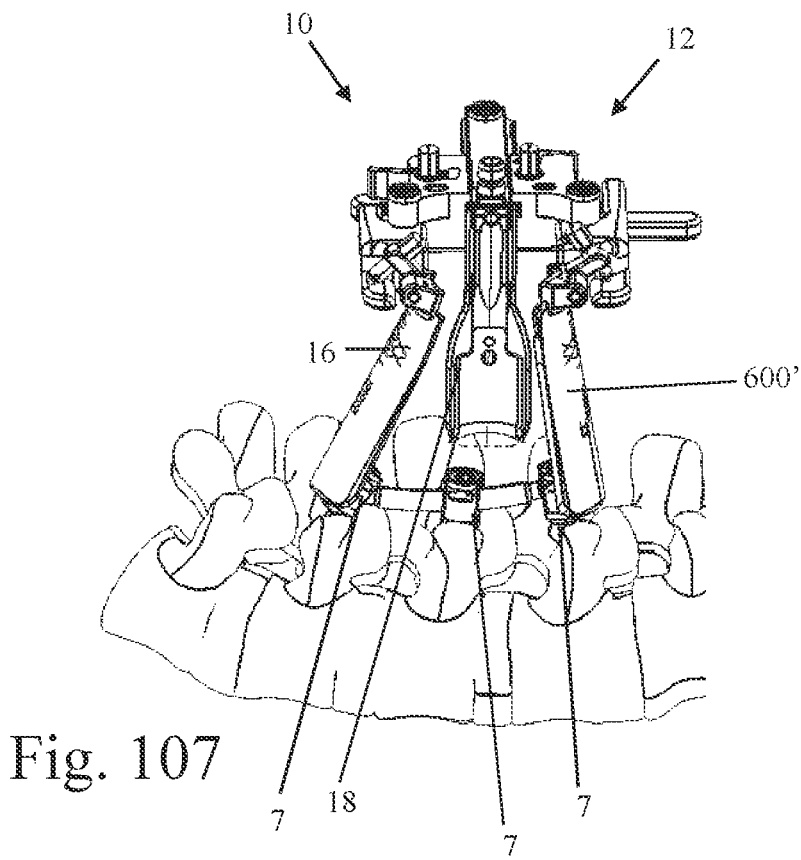
Figure 108:
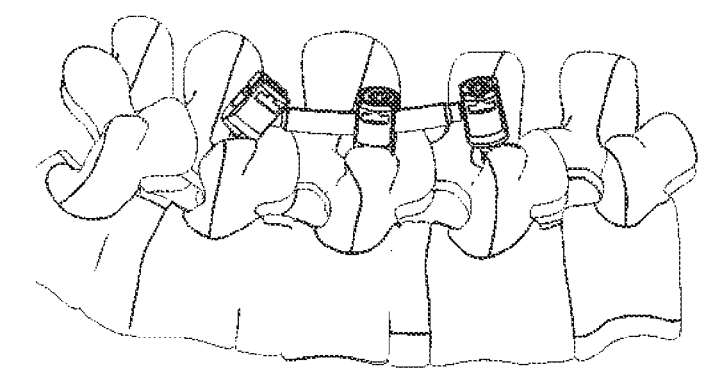

At this point, with the retractor blades 14, 600' protruding from the incision and the distal ends of the blades being securely registered to the anchor members 7 via the hoop shim assemblies 6, the retractor blades 14, 600' may be attached to the retractor body 14 (FIG. 104). The surgeon may then operate the retractor body 12 to cause the retractor blades 14, 14, 600' to move in cranial and caudal directions, respectively, at the skin level. As previously described, because the distal portions of the retractor blades 14, 600' are securely (and polyaxially) registered to the implanted anchor members 7, the distal end of the blades will not move. However, the angle of the retractor blades 14, 600' relative to the anchor members 7 may be adjusted to a desired angle and the new operative corridor will be established to the second spinal level. Once established, the retractor body 12 may be locked to an articulating arm (not shown) by either one of the attachment members 53 of the retractor body 12, or attachment members 109 of the medial rack 108. Using a suitable tool or a finger, the surgeon then releases soft tissue from the facet. A medial retractor blade 16 may then be inserted and retracted as desired (FIG. 105). As mentioned previously, the medial retractor blade may operate to clear remaining soft tissue from the facet. The medial retractor blade 16 may be angled to match the operative corridor by pivoting the blade in a plane that is transverse to the longitudinal axis of the medial rack 108. In this fashion, the entire operative corridor may be established at an angle that is suitable for superior access to the disc space.

At this point, with the new operative corridor 4' established, and has distinct landmarks (i.e. the implanted anchor members 7) delineating the cranial and caudal boundaries of the new operative window. The surgeon can now perform the necessary steps to clean out the intervertebral disc space and perform the interbody fusion procedure. As above, this may include a facetectomy in which at least a portion of the facet joint is removed, allowing access to the intervertebral disc space and a discectomy. The interbody implant is then inserted into the cleaned out disc space. By way of example only this may include, but not be limited to, inserting one or more artificial or allograft implants within the intervertebral space. According to one example, the implant may be inserted and positioned obliquely across the disc space. If necessary, the surgeon may use the tissue retraction system 10 to distract the disc space with the retractor body 12.

After placement of the interbody implant, the distraction off the screws is released, and the hoop shim assemblies 6 are removed using the hoop shim removal tool 350 as described above. The surgeon then "opens" the retractor slightly in a caudal-cranial direction using the thumbscrews 240 on the blades (opposed to the rack assembly 22) as described below to increase the space around the pedicle screws. The pedicle screw receivers or tulips are then inserted onto the pedicle screw and the retractor blade 600' can be actuated to expand out to the first anchor of the first vertebra (preferably by splaying the distal portion of the retractor blade to minimize expansion at the top of the operative corridor. A spinal fixation rod is then placed within the tulips, followed by compression (if necessary). With the procedure is completed, the retractor can be returned to a "closed" position and then removed from the patient, closing the operative corridor. The surgeon will then close the operative wound, completing the procedure.

Although described with respect to specific examples of the different embodiments, any features of the systems and methods disclosed herein by way of example only may be applied to any of the embodiments without departing from the scope of the present invention. Furthermore, procedures described for example only involving specific structure (e.g. vertebral bone) may be applied to another structure (e.g. femur) without departing from the scope of the present invention. While this invention has been described in terms of a best mode for achieving this invention's objectives, it will be appreciated by those skilled in the art that variations may be accomplished in view of these teachings without deviating from the spirit or scope of the invention.

One advantageous feature of the surgical fixation and retraction system described herein is the registration of the distal ends of the retractor blades 14, 16 to the implanted bone anchors 7. Although described herein by way example as using a hoop shim assembly 6 to accomplish this purpose, other attachment mechanisms are possible, including but not limited to sutures, cables, hooks, etc.

The example method of performing surgery described herein disclosed the use of an electrified tap, in order to enable pedicle integrity testing during pilot hole formation. However, the system described herein may be provided with additional features to enable pedicle integrity testing before, during, and after placement of the bone anchors within the pedicle. For example, using the electrified tap as described above is one way to test for pedicle integrity prior to placement of the bone anchors. However, the system may be equipped to continuously monitor for pedicle integrity during placement of the bone anchors as well. For example, the blade-anchor-shim-inserter assembly may be substantially insulated, either through an insulative coating or an external barrier (e.g. sheath, cannula, etc) such that only a portion of the bone anchor (e.g. the distal tip) is electrified to deliver stimulation to evoke an EMG response. EMG monitoring can be continuous to test for potential pedicle breach during placement of the bone anchors. Moreover, pedicle integrity can be further tested for upon final placement of the bone anchors.

Although shown and described herein in use with a specific example of a TLIF procedure on a human spine, the tissue retraction assembly herein may be used for a variety of different procedures involving any parts of the body. The surgical fixation system described herein is well suited for use in any procedure involving decompression using bone anchors. The surgical fixation system can be used for any type of bony fusion, including discectomy and fusion. Within the spine space apart from fusion, the tissue retraction system can be used to create an operative corridor to enable any type of procedure, including but not limited to vertebral augmentation and vertebroplasty.

By way of example only, the various components of the surgical fixation system described herein may be manufactured of any material suitable to achieve the goals of stability and rigidity, including the ability to use the blades to distract the bony segments. By way of example only, the retractor body and retractor blades are made of stainless steel, however any metallic substance is possible without departing from the scope of the present invention. Moreover, any part of the system described herein, including for example the retractor blades, may be composed of image-friendly material such as carbon fiber reinforced polymer (CFRP) or poly-ether-ether-ketone (PEEK) without departing from the scope of the present invention. The ability to intraoperatively switch out retractor blades may be advantageous in that one or more image-friendly retractor blades may be used to initially establish the working channel, and then be intraoperatively exchanged for a stainless steel retractor blade in the event that the surgeon wishes to use the blades to distract the disc space.

What is claimed is:

1. A method for performing a spinal fixation procedure, the method comprising:
    coupling a distal end of a first retractor blade to a first portion of a first bone anchor;
    after coupling the first retractor blade: anchoring the first bone anchor to a first region of bone;
    uncoupling the first retractor blade from the first bone anchor having a first shank disposed in the first region of bone; and
    after uncoupling the first retractor blade:
        coupling a first receiver to the first bone anchor;
        inserting a rod into the first receiver; and
        locking the rod to the first receiver.

2. The method of claim 1, further comprising:
    uncoupling a second retractor blade from a second bone anchor having a second shank disposed in a second region of bone; and
    after uncoupling the first retractor blade:
        coupling a second receiver to the second bone anchor;
        inserting the rod into the second receiver; and
        locking the rod to the second receiver.

3. The method of claim 2, further comprising:
    anchoring the first bone anchor to a first pedicle of a first vertebra; and
    anchoring the second bone anchor to a second pedicle of a second vertebra.

4. The method of claim 1, wherein the first region of bone is a first pedicle of a first vertebra.

5. A method for performing a spinal fixation procedure on a spinal segment of a human spine, the spinal segment including at least a first vertebra and a second vertebra separated from the first vertebra by an intervertebral disc space, comprising:
    coupling a distal end of a first retractor blade to a first portion of a first bone anchor;
    coupling a distal end of a second retractor blade to a first portion of a second bone anchor;
    after coupling the distal end of the first retractor blade to the first portion of the first bone anchor, anchoring the first bone anchor to a pedicle of the first vertebra;
    after coupling the distal end of the second retractor blade to the first portion of the second bone anchor, anchoring the second bone anchor to a pedicle of the second vertebra;
    create an operative corridor to a spinal segment, the operative corridor defined, in part, by the first retractor blade and the second retractor blade;
    uncoupling the first retractor blade from the first portion of the first bone anchor and coupling a first receiver to the first portion of the first bone anchor;

uncoupling the second retractor blade from the first portion of the second bone anchor and coupling a second receiver to the first portion of the second bone anchor;
inserting a rod into the first and second receivers;
locking the rod to the first and second receivers; and
removing the first and second retractor blades from the operative corridor.

6. The method of claim 5, further comprising;
coupling a proximal end of the first retractor blade to a first arm of a retractor body; and
coupling a proximal end of the second retractor blade to a second arm of the retractor body.

7. The method of claim 5, further comprising:
advancing a third retractor blade through the operative corridor to the spinal segment;
coupling the third retractor blade to a translating arm of the retractor body or of a supplemental retractor body; and
moving the third retractor blade away from the first and second retractor blades in a second direction different from the first direction.

8. The method of claim 5, wherein the distal end of the first retractor blade is coupled to a first portion of the first bone anchor via a hoop shim slidably engaged with the first retractor blade.

9. The method of claim 5,
wherein the first retractor blade is coupled to the first portion of the first bone anchor in a polyaxial engagement; and
wherein the second retractor blade is coupled to the first portion of the second bone anchor in a polyaxial engagement.

10. The method of claim 5, further comprising adjusting an angle of the operative corridor relative to the spinal segment.

11. The method of claim 10, wherein the adjusted angle of the operative corridor is more parallel to the intervertebral disc space than the angle was prior to the adjusting.

12. The method of claim 5, wherein the distal end of the second retractor blade is coupled to a first portion of the second bone anchor via a hoop shim slidably engaged with the second retractor blade.

13. A method comprising:
performing a transforaminal lumbar interbody fusion, wherein the performing includes:
coupling a distal end of a first retractor blade to a first portion of a first bone anchor;
after coupling the first retractor blade: anchoring the first bone anchor to a first pedicle of a first vertebra;
uncoupling the first retractor blade from the first bone anchor having a first shank disposed in the first pedicle of the first vertebra; and
after uncoupling the first retractor blade:
coupling a first receiver to the first bone anchor;
inserting a rod into the first receiver; and
locking the rod to the first receiver.

14. The method of claim 13, further comprising:
uncoupling a second retractor blade from a second bone anchor having a second shank disposed in a second region of bone; and
after uncoupling the first retractor blade:
coupling a second receiver to the second bone anchor;
inserting the rod into the second receiver; and
locking the rod to the second receiver.

15. The method of claim 14, further comprising:
anchoring the second bone anchor to a second pedicle of a second vertebra.

16. The method of claim 13, further comprising:
prior to uncoupling the first retractor blade, through an operative corridor defined at least in part by the first retractor blade:
performing a discectomy at an intervertebral space; and
after performing the discectomy, inserting an implant into the intervertebral space.

17. The method of claim 16, further comprising:
manipulating the first retractor blade to distract the intervertebral space prior to performing the discectomy.

\* \* \* \* \*